US009945878B1

(12) United States Patent
Gordon et al.

(10) Patent No.: US 9,945,878 B1
(45) Date of Patent: *Apr. 17, 2018

(54) COMPOSITIONS AND SOLUTIONS FOR TARGET SUBSTANCE DETECTION AND MEASUREMENT

(71) Applicant: Hound Labs, Inc., Oakland, CA (US)

(72) Inventors: Michael J. Gordon, Goleta, CA (US); Louis Chin Jones, Santa Barbara, CA (US)

(73) Assignee: HOUND LABS, INC., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,518

(22) Filed: Jul. 14, 2017

Related U.S. Application Data

(63) Continuation of application No. 14/997,405, filed on Jan. 15, 2016, now Pat. No. 9,726,684.

(60) Provisional application No. 62/277,854, filed on Jan. 12, 2016, provisional application No. 62/107,331, filed on Jan. 23, 2015, provisional application No. 62/104,813, filed on Jan. 18, 2015.

(51) Int. Cl.
| | |
|---|---|
| *G01N 33/94* | (2006.01) |
| *G01N 21/64* | (2006.01) |
| *G01N 33/58* | (2006.01) |
| *A61B 5/087* | (2006.01) |
| *A61B 5/08* | (2006.01) |
| *A61B 5/097* | (2006.01) |

(52) U.S. Cl.
CPC ........... *G01N 33/948* (2013.01); *A61B 5/082* (2013.01); *A61B 5/087* (2013.01); *A61B 5/097* (2013.01); *G01N 21/6428* (2013.01); *G01N 33/582* (2013.01); *G01N 2021/6439* (2013.01)

(58) Field of Classification Search
CPC .................................................. G01N 33/948
See application file for complete search history.

(56) References Cited

U.S. PATENT DOCUMENTS

| | | | |
|---|---|---|---|
| 3,086,833 | A | 4/1963 | Streck |
| 3,676,072 | A | 7/1972 | Krivis |
| 4,288,344 | A | 9/1981 | Reiss |
| 4,771,005 | A | 9/1988 | Spiro |
| 5,922,610 | A | 7/1999 | Alving et al. |
| 6,605,444 | B1 | 8/2003 | Klein et al. |
| 8,707,758 | B2 | 4/2014 | Keays |
| 9,709,581 | B1 | 7/2017 | Gordon et al. |
| 9,709,582 | B1 | 7/2017 | Gordon et al. |
| 9,726,684 | B1 * | 8/2017 | Gordon ................ G01N 33/948 |
| 2002/0177232 | A1 | 11/2002 | Melker et al. |
| 2003/0153844 | A1 | 8/2003 | Smith |
| 2004/0043479 | A1 | 3/2004 | Briscoe et al. |
| 2005/0105077 | A1 | 5/2005 | Padmanabhan et al. |
| 2005/0137491 | A1 | 6/2005 | Paz et al. |
| 2007/0077660 | A1 | 4/2007 | Glas |
| 2008/0004542 | A1 | 1/2008 | Allen et al. |
| 2011/0086364 | A1 | 4/2011 | Takkinen et al. |
| 2012/0302907 | A1 | 11/2012 | Palmskog et al. |
| 2013/0006068 | A1 | 1/2013 | Gemer et al. |
| 2013/0021153 | A1 | 1/2013 | Keays |
| 2014/0288454 | A1 | 9/2014 | Paz et al. |
| 2015/0305651 | A1 | 10/2015 | Attariwala et al. |

FOREIGN PATENT DOCUMENTS

| | | |
|---|---|---|
| EP | 132313 | 9/1991 |
| EP | 2781917 | 9/2014 |
| WO | 2006/083269 | 8/2006 |

OTHER PUBLICATIONS

"Information for health care professionals: cannabis (marihuana, marijuana) and the cannabinoids," Health Canada, Feb. 2013.
"Marihuana '84," Proceedings of the Oxford Symposium on Cannabis, D.J. Harvy, editor, IRL Press, Oxford 1984.
"The Chemistry of Phenols," Zvi Rappoport, editor, .COPYRGT. 2003 John Wiley & Sons, Ltd. ISBN: 0-471-49737-1.
Adams, I.B. et al., "Cannabis: pharmacology and toxicology in animals and humans," Addiction, Nov. 1996;91 (11):1585-614, PubMed abstract 8972919.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988;14(4):217-40, PubMed abstract 3292101.

(Continued)

*Primary Examiner* — Joseph R Kosack
(74) *Attorney, Agent, or Firm* — Weaver Austin Villeneuve & Sampson, LLC.

(57) ABSTRACT

Various embodiments for a hand-held device to determine a level of one or more cannabinoid compounds in exhaled human breath are provided; some embodiments may also determine a level of alcohol in the exhaled breath. The device may perform any of the following steps: capture, concentrate, separate, identify, and quantify the level of cannabinoids in the exhaled human breath. The device may use solvent extraction and liquid chromatography to concentrate and separate cannabinoids from breath contaminants, followed by selective chemical modification of the cannabinoids with a fluorescent indicator for quantification. The measurement methodology may also include real time calibration of the device and detection protocol using known cannabinoid standards, which are simultaneously analyzed along with an unknown, to quantify the level of cannabinoids captured from the breath sample. The capture and separation components, along with cannabinoid analysis standards, may be configured as part of a single-use, field-replaceable testing cartridge.

20 Claims, 46 Drawing Sheets

(56) References Cited

OTHER PUBLICATIONS

Azorlosa, J.L. et al., "Marijuana smoking: effect of varying delta 9-tetrahydrocannabinol content and number of puffs," J. Pharmacol. Exper. Ther 1992;261:114, abstract.

Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.

Baker, D. et al., "Cannabinoids control spasticity and tremor in a multiple sclerosis model," Nature, Mar. 2, 2000;404(6773):84-7, abstract.

Balabanova, S. et al., "Detection of drugs in sweat," Belt Gerichtl Med. 1990;48:45-9, abstract.

Bashir W. et al, Spectrophotometric Determination of Acetone in Acetic Acid, Microchemical Journal, 1983, 28, pp. 77-81.

Beck, Olof et al., "Detection of Delta9-tetrahydrocannabinol in exhaled breath collected from cannabis users," Journal of Analytical Toxicology, vol. 35, Oct. 2011.

Benowitz, Neal L. et al., "Metabolic and psychophysiologic studies of cannabidiol-hexobarbital interaction," Clinical Pharmacology and Therapeutics (1980) 28, 115-120, abstract.

Blanc, Jennifer A. et al., "Adsorption losses from urine-based cannabinoid calibrators during routine use," Clin. Chem. 39/8, 1705-1712 (1993).

Bloom, A.S., Effect of delta9-tetrahydrocannabinol on the synthesis of dopamine and norepinephrine in mouse brain synaptosomes, J Pharmocol Exp Ther. Apr. 1982;221(1):97-103.

Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.

Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.

Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.

Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.

Burstein, S. et al., "Isolation and characterization of two major urinary metabolites of 1-tetrahydrocannabinol," Science, Apr. 28, 1972;176(4033):422-3, PubMed abstract 5026162.

Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.

Challapalli, P.V. et al., "In vitro experiment optimization for measuring tetrahydrocannabinol skin permeation," Int J Pharm. Jul. 25, 2002;241(2):329-39, PubMed abstract 12100860.

Chaturvedi, Arvind K., "Postmortem aviation forensic toxicology: an overview," Journal of Analytical Toxicology, vol. 34, May 2010.

Chiang, C. Nora et al., "Prenatal drug exposure: kinetics and dynamics," NIDA Research Monograph 60, 1985.

Christophersen, Asbjorg Solberg et al., "Tetrahydrocannabinol stability in whole blood: plastic versus glass containers," Journal of Analytical Toxicology, vol. 10, Jul./Aug. 1986.

Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.

Cone, Edward J. et al., "In vivo adulteration: excess fluid ingestion causes false-negative marijuana and cocaine urine test results," Journal of Analytical Toxicology, vol. 22, Oct. 1998.

Cone, Edward J. et al., "Marijuana-laced brownies: behavioral effects, physiologic effects, and urinalysis in humans following ingestion," Journal of Analytical Toxicology, vol. 12, Jul./Aug. 1988.

Cone, Edward J. et al., "Passive inhalation of marijuana smoke: urinalysis and room air levels of delta-9-tetrahydrocannabinol," Juornal of Analytical Toxicology, vol. 11, May/Jun. 1987.

Crouch, D.J., "Oral fluid collection: the neglected variable in oral fluid testing," Forensic Sci Int. Jun. 10, 2005;150(2-3):165-73, PubMed abstract 15899565.

Crouch, Dennis J. et al., "An evaluation of selected oral fluid point-of-collection drug-testing devices," Journal of Analytical Toxicology, vol. 29, May/Jun. 2005.

Day, David et al., "Detection of THCA in oral fluid by GC-MS-MS," Journal of Analytical Toxicology, vol. 30, Nov./Dec. 2006.

D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.

Ellis, G.M. Jr. et al., "Excretion patterns of cannabiniod metabolites after last use in a group of chronic users," Clin Pharmacol Ther. Nov. 1985;38(5):572-8, PubMed abstract 3902318.

Ellis, George M. Jr. et al. "Excretion patterns of cannabinoid metabolites after last use," 420 Magazine, Oct. 4, 2011, downloaded from https://www.420magazine.com/forums/drug-testing-urine/153724.

ElSohly, M. et al., "Potency trends of Delta9-THC and other cannabinoids in confiscated marijuana from 1980-1997," Journal of Forensic Sciences, vol. 45, No. 1, 2000, pp. 24-30.

Feng, Shixia et al., "Simultaneous analysis of Delta9-THC and its major metabolites in urine, plasma, and meconium by Gc—Ms using an immunoaffinity extraction procedure," Journal of Analytical Toxicology, vol. 24, Sep. 2000.

Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.

Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.

Fraser, A.D. et al., "Urinary excretion profiles of 11-nor-9-carboxy-Delta9-tetrahydrocannabinol. StudyIII. A Delta9-THC-COOH to creatinine ratio study," Forensic Sci Int. Nov. 26, 2003;137(2-3):196-202, PpubMed abstract 14609657.

Garrett, E.R. et al., "Pharmacokinetics of delta9-tetrahydrocannabinol in dogs," J Pharm Sci. Mar. 1977;66(3):395-407, PubMed abstract 845807.

Garrett, Edward R. et al., "Physicochemical properties, solubility, and protein binding of Delta9-tetrahydrocannabinol," J Pharm Sci. Jul. 1974;63(7):1056-64, abstract.

Gjerde, H. et al., "Incidence of alcohol and drugs in fatally injured car drivers in Norway," Accid Anal Prey. Aug. 1993;25(4):479-83, PubMed abstract 8357462.

Gjerde, Hallvard et al., "Comparison of drug concentrations in blood and oral fluid collected with the Intercept.RTM. sampling device," Journal of Analytical Toxicology, vol. 34, May 2010.

Goodwin, R.S. et al., "Delta(9)-tetrahydrocannabinol, 11-hydroxy-delta(9)tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.

Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Matabilism and Disposition, vol. 25, No. 12, (1997).

Gross, Stanley J. e al., "Detection of recent cannabis use by saliva Delta9-THC radioimmunoassay," Journal of Analytical Toxicology, vol. 9, Jan./Feb. 1985.

Grotenhermen, F., "Pharmacokinetics and pharmacodynamics of cannabinids," Clin Pharmacokinet. 2003;42(4):327-60, PubMed abstract 12648025.

Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with

(56) References Cited

OTHER PUBLICATIONS positive chemical ionization," J. Chromatogr B Analyt Technol Biomed Life Sci, Dec. 5, 2003;798(1):145-54, PubMed abstract 14630369.

Gustafson, Richard A. et al., "Urinary cannabinoid detection times after controlled oral administration of Delta9-tetrahydrocannabinol to humans," Clinical Chemistry 49:7, 1114-1124 (2003).

Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.

Guy, G.W. et al., "A phas I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.

Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.

Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.

Hampson, A.J. et al., "Cannabidiol and (−)delta9-tetrahydrocannabinol are neuroprotective antioxidants," Proc Natl Acad Sci U.S.A. Jul. 7, 1998; 95(14):8268-8273.

Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.

Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.

Harvey, D.J. et al., "Metabolites of cannabidiol identified in human urine," Xenobiotic, Mar. 1990;20(3):303-20, PubMed abstract 2336840.

Hawks, Richard L., "The Analysis of Cannabinoids in Biological Fluids," NIDA Research Monograph 42, 1982.

Hazekamp, Arno et al., "Cannabis; extracting the medicine," thesis/dissertation 2007.

Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.

Himes, Sarah K. et al., "Cannabinoids in exhaled breath following controlled administration of smoked cannabis," Clinical chemistry 59:12 1780-1789 (2013).

Huang, Wei et al., "simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.

Huestis, M.A. et al., "Characterization of the absorption phase of marijuana smoking," Clin Pharmacol Ther. Jul. 1992;52(1):31-41, PubMed abstract 1320536.

Huestis, Marilyn A. et al., "Alternative testing matrices," chapter 11 of the Drug Abuse Handbook, 1998 CRC Press LLC, ISBN 0-8493-2637-0.

Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.

Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.

Huestis, Marilyn A. et al., "Cannabinoid concentrations in hair from documented cannabis users," Forensic Sci Int. Jul. 4, 2007; 169(2-3): 129-136.

Huestis, Marilyn A. et al., "Detection times of marijuana metabolites in urine by immunoassay and GC-MS," Journal of Analytical Toxicology, vol. 19, Oct. 1995.

Huestis, Marilyn A. et al., "Differentiating new marijuana use from residual drug excretion in occasional marijuana users," Journal of Analytical Toxicology, vol. 22, Oct. 1998.

Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).

Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.

Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.

Huestis, Marilyn A., "Human cannabinoid pharmacokinetics," Chem Biodivers. Aug. 2007; 4(8): 1770-1804.

Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.

Hunt, C.A. et al., "Tolerance and disposition of tetrahydrocannabinol in man," J Pharmacol Exp Ther. Oct. 1980;215(1):35-44, PubMed abstract 6256518.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johansson, Eva et al., "Urinary excretion half-life of deltal-tetrahydrocannabinol-7-oic acid in heavy marijuana users after smoking," Journal of Analytical Toxicology, vol. 13, Jul./Aug. 1989.

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. I. Analysis of delta9-tetrahydrocannabinol and six metabiloties in plasma and urine using GC-MS," Journal of Analytical Toxicology, vol. 19, Sep. 1995.

(56) References Cited

OTHER PUBLICATIONS

Kemp, Philip M. et al., "Cannabinoids in Humans. II. The influence of three methods of hydrolysis on the concentration of THC and two matabilites in urine," Journal of Analytical Toxicology, vol. 19, Sep. 1995.

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program," Clinical Chemistry 43:5, 736-739 (1997).

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaird drivers and evaluation of the on-site Drager Drug Test," Forensic Sci Int. Sep. 12, 2006;161(23):175-9, PubMed abstract 16842950.

Law, B. et al., "Forensic aspects of the metabilism and excretion of cannabinoids following oral ingestion of cannabis resin," J Pharm Pharmacol. May 1984;36(5):289-94, PubMed abstract 6145762.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed abstract 5479011.

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.

Manno, Joseph E. et al., "Temporal indication of marijuana use can be estimated from plasma and urine concentraitons of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.

Manolis, Antony et al., "The detection of delta9-tetrahydrocannabinol in the breath of human subjects," Clinical Biochem. 16,229 (1983).

Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.

Mason, A.P. et al., "Cannabis: pharmacology and interpretation of effects," J Forensic Sci. Jul. 1985;30(3):615-31, PubMed abstract 2993473.

Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.

Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.

Mattes, R.D. et al., "Bypassing the first-pass effect for the therapeutic use of cannabinoids," Pharmacol Biochem Behav. Mar. 1993;44(3):745-7, PubMed abstract 8383856.

Mattes, R.D. et al., "Cannabinoids and appetite stimulation," Pharmacol Biochem Behav. Sep. 1994;49(1):187-95, PubMed abstract 7816872.

McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.

Mechoulam, Raphael et al., "Cannabidiol: an overview of some chemical and pharmacological aspects. Part I: chemical aspects," Chemistry and Physics of Lipids 121 (2002) 35-43.

Mechoulam, Raphael, "Plant cannabinoids: a neglected pharmacological treasure trove," Br J Pharmacol. Dec. 2005; 146(7): 913-915.

Meier, H. et al., "Cannabis poisoning after eating salad," Schweiz Med Wochenschr. Feb. 8, 1997;127(6):214-8, PubMed abstract 9157527.

Menkes, D.B. et al., "Salivary THC following cannabis smoking correlates with subjective intoxication and heart rate," Psychopharmacology (Berl). 1991;103(2):277-9, PubMed abstract 1851311.

Mijuriya, Tod H., "Cannabis as a substitute for alcohol: a harm-reduction approach," Journal of Cannabis Therapeutics, vol. 4(1) 2004.

Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.

Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.

Moldoveanu, Serban C. et al., "Differences in the chemical composition of the particulate phase of inhaled and exhaled cigarette mainstream smoke," Contributions to Tobacco Research 22(4), 290 (2007).

Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.

Moore, Christine et al., "Application of two-dimensional gals chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.

Moore, Christine et al., "Detection of the marijuana metabilite 11-nor-delta9-tetrahydrocannabino1-9-carboxylic acid in oral fluid specimens and its contribution to positive results in screening assays," Journal of Analytical Toxicology, vol. 30, Sep. 2006.

Moore, Christine et al., "The determination of 11-nor-delta9-tetrahydrocannabino1-9-carboxylic acid (THC-COOH) in hair using negative ion gas chromatography-mass spectrometry and high-volume injection," Journal of Analytical Toxicology, vol. 25, Oct. 2001.

(56) References Cited

OTHER PUBLICATIONS

Morland, J. et al., "Cannabinoids in blood and urine after passive inhalation of cannabis smoke," J Forensic Sci. Oct. 1985;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana," Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled deltal-tetrahydrocnnabinol in heavy and light cannabis users," Biological Mass Spectrometry, vol. 9, Issue 1, pp. 6-10, Jan. 1982, abstract.
Owens, S. Michael et al., I Radioimmunoassay of delta-9-tetrahydrocannabinol in blood and plasma with a solid-phase second-antibody separation method, Clin. Chem. 27/4, 619-624 (1981).
Peel, H.W. et al., "Detection of drugs in saliva of impaired drivers," J Forensic Sci. Jan. 1984;29(1):185-9, PubMed abstract 6366113.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-0H-9-tetrahydrocannabinol," Science. Aug. 18, 1972;177(4049):633-5, PubMed abstract 4558903.
Perez-Reyes, M. et al., "The clinical pharmacology and dynamics of marihuana cigarette smoking," J Clin Pharmacol. Aug.-Sep. 1981;21(8-9 Suppl):2015-2075, PubMed abstract 6271825.
Perez-Reyes, Mario, "Marijuana smoking: facotrs that influence the bioavailability of tetrahydrocannabinol," NIDA Monograph 1990;99:42.
Piao, Wen et al., "Development of azo-based fluorescent probes to detect different levels of hypoxia," Angew. Chem. Int. Ed. 2013, 52, 13028-13032.
Quintela, Oscar et al., "Recovery of drugs of abuse from the immunalysis quantisal.TM. oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11):1489-91, PubMed abstract 18965558.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11):1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).
Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).
Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.
Soares, J.R. et al., "Significant developments in radioimmune methods applied to delta9-THC and its 9-substituted metabolites," Analysis of Cannabinoids Research Monograph 42, NIDA 1982.
Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.
Strano-Rossi, Sabina et al., "Analysis of stimulants in oral fluid and urine by gas chromatography-mass spectrometry II: Pseudophedrine," Journal of Analytical Toxicology, vol. 34, May 2010.
Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.
Teshima N. et al, Determination of acetone in breath, Analytica Chimica Acta, 2005, 535, pp. 189-199.
Toennes, Stefan W. et al., "Pharmacokinetic properties of delta9-tetrahydrocannabinol in oral fluid of occasional and chronic users," Journal of Analytical Toxicology, vol. 34, May 2010.
Turner, Carton E. et al., "Constituents of cannabis sativa 1. XVII. A review of the natural constituents," J. Nat. Prod. 1980;43:169.
Valiveti, S. et al., "In vitro/in vivo correlation studies for transdermal delta 8-THC development," J Pharm Sci. May 2004;93(5):1154-64, PubMed abstract 15067692.
Van der Kooy, F. et al., "Cannabis smoke condensate I: The effect of different preparation methods on tetrahydrocannabinol levels," Inhalation Toxicology, 20:801-804, 2008.
Vinciguerra, V. et al., "Inhalation marijuana as an antiemetic for cancer chemotherapy," NY State J Med. Oct. 1988;88(10):525-7.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.
Wall, M.E. et al., "The metabolism of delta 9-tetrahydrocannabinol and related cannabinoids in man," J Clin Pharmacol. Aug.-Sep. 1981;21 (8-9 Suppl):1785189S, PubMed abstract 6271823.
Walsh, J. Michael et al., "An evaluation of rapid point-of-collection oral fluid drug-testing devices," Journal of Analytical Toxicology, vol. 27, Oct. 2003.
Watanabe, K. et al., "Brain microsomal oxidation of delta 8- and delta 9-tetrahydrocannabinol," Biochem Biophys Res Commun. Nov. 30, 1988;157(1):7580, PubMed abstract 2848522.
Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.

(56) References Cited

OTHER PUBLICATIONS

Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.

Wingert, William E., "Lowering cutoffs for initial and confirmation testing for cocaine and marijuana: large-scale study of effects on the rates of drug-positive results," Clinical Chemistry 43:1 100-103 (1997).

Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.

Zias, Joe et al., "Early medical use of cannabis," Nature; May 20, 1993; 363,6426; Research Library Core p. 215.

Zuardi, A.W. et al., "Action of cannabidiol on the anxiety and other effects produced by delta 9-THC in normal subjects," Psychopharmacology (Berl). 1982;76(3):245-50, PubMed abstract 6285406.

U.S. Appl. No. 14/997,405, Office Action dated Jan. 9, 2017.
U.S. Appl. No. 14/997,405, Notice of Allowance dated May 10, 2017.
U.S. Appl. No. 14/997,405, Corrected Notice of Allowability dated Jun. 15, 2017.
U.S. Appl. No. 15/143,379, Office Action dated Oct. 25, 2016.
U.S. Appl. No. 15/143,379, Notice of Allowance dated Mar. 21, 2017.
U.S. Appl. No. 15/143,328, Office Action dated Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowability dated Jun. 14, 2017.
U.S. Appl. No. 15/143,379, Notice of Allowability dated Jun. 13, 2017.
U.S. Appl. No. 14/641,412, filed Mar. 8, 2015, Michael Scott Lynn et al.
U.S. Appl. No. 15/217,151, filed Jul. 22, 2016, Michael Scott Lynn et al.
U.S. Appl. No. 15/217,264, filed Jul. 22, 2016, Michael Scott Lynn et al.
U.S. Appl. No. 15/650,537, filed Jul. 14, 2017, Michael J. Gordon et al.
U.S. Appl. No. 14/641,412, Office Action dated May 19, 2016.
U.S. Appl. No. 14/641,412, Office Action dated Dec. 5, 2016.
U.S. Appl. No. 14/641,412, Office Action dated Jun. 26, 2017.
U.S. Appl. No. 15/217,151, Office Action dated Jan. 9, 2017.
U.S. Appl. No. 15/217,151, Office Action dated May 16, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Notice of Allowance dated Nov. 16, 2017.

* cited by examiner (or)

COMPOSITIONS AND SOLUTIONS FOR TARGET SUBSTANCE DETECTION AND MEASUREMENT

CROSS REFERENCE TO RELATED APPLICATIONS

This application is a continuation of U.S. patent application Ser. No. 14/997,405, filed Jan. 15, 2016, now allowed, titled "METHOD, DEVICE AND SYSTEM FOR TARGET SUBSTANCE DETECTION", which claims priority benefit under 35 U.S.C. § 119(e) to U.S. Provisional Application No. 62/104,813, filed Jan. 18, 2015, and to U.S. Provisional Patent Application No. 62/107,331, filed Jan. 23, 2015, both of which are titled "METHOD, DEVICE AND SYSTEM FOR TARGET SUBSTANCE DETECTION," as well as to U.S. Provisional Application No. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH," all of which are hereby incorporated by reference herein in their entireties.

FIELD OF THE INVENTION

The present disclosure relates generally to analytical measurement devices, and more specifically to devices capable of measuring substances in exhaled human breath.

BACKGROUND

With legalization of marijuana expanding and the risk of marijuana-associated impaired driving increasing, a handheld device—much like a breathalyzer for alcohol—is urgently needed to rapidly quantify levels of cannabinoid compounds, such as tetrahydrocannabinol (THC) of suspected users at the roadside. Published data [1-3], all of which are hereby incorporated by reference in their entireties with respect to the use of THC in breath as a superior indicator of recent marijuana usage as compared with traces of THC in blood or urine, suggest that THC in breath is a better indicator of recent marijuana use and impairment compared to THC in blood or urine due to their long clearance times [4-7], all of which are also hereby incorporated by reference in their entireties with respect to the use of THC in breath as a superior indicator of recent marijuana usage as compared with traces of THC in blood or urine. Testing for THC in breath at the roadside would be convenient, non-invasive, and leverages the wide acceptance of administering a breath test at the roadside, as is commonly employed for alcohol.

SUMMARY

Quantitative detection of THC in human breath is challenging and not previously possible with a handheld device due to the extremely low concentration and the presence of many common, similarly structured contaminants or chemical interferences.

As disclosed herein, complex breath constituents from one or more (e.g., 1-3) exhalations may be contacted with and collected in a small volume of solvent, which subsequently may be fractionated (separated) into molecular components (target and non-target molecular species) that are reacted with an indicator and quantified optically.

Non-target molecular species (e.g., smoke constituents, simple alcohols, phenol, and ketones, etc.) may be separated from a cannabinoid assay using lipophilic absorption media, a solvent extraction process, and liquid chromatography. Although little is known, or has been published, about the organic compounds present in exhaled *cannabis* smoke, it is likely that many of these compounds are similar to those found in exhaled tobacco smoke. The compounds that are likely to be common to both *cannabis* and tobacco smoke are generally related to combustion of organic vegetable matter, such as C1-C8 linear, branched, and aromatic hydrocarbons, alcohols, diols, aldehydes, ketones, fatty acids, furans, indoles, and phenols [19], which is hereby incorporated by reference in its entirety with respect to at least the compounds that are likely to be common to both *cannabis* and tobacco smoke. Tobacco-specific compounds are most likely to include menthol, eugenol, nicotine, cholesterols, vitamin E, and long chain fatty acids; it is unknown at the present time if these compounds also exist in *cannabis* smoke because no published data exists.

However, some compounds, such as phenols and other aromatic alcohols, whether or not they exist in *cannabis* smoke, can interfere with detection and quantification of THC. Notwithstanding, the solvent extraction and liquid chromatography (LC) procedure presented herein was designed to specifically remove these known interferents (phenols and aromatic alcohols, which react with certain indicators) as well as unreacted indicator.

In various embodiments, a fluorescent indicator may be used to selectively react with and bind to THC and other cannabinoids, for example at the para position of the aromatic alcohol region of THC and other cannabinoids, to form a fluorescent adduct. A fluorescence intensity and spectral shift of the fluorescent adduct may be used for quantification of a sample having an unknown concentration through comparison with THC standards measured alongside the unknown.

Calibration may include measuring an optical fluorescence signal from, for example, 3 known THC standards and creating a plot of optical signal, represented as, for example, total photons, photons/sec, or electrical current from photons hitting the detector, versus THC level, expressed in picograms (pg). A smooth curve may be fit to the calibration data using least-squares regression to provide a calibration equation from which to quantify the unknown. The functional form of the calibration equation (e.g., linear, quadratic, cubic, exponential, or sigmoidal), along with the fit parameters, may be chosen based on the equation giving the highest statistical correlation coefficient, $r^2$. This calculation and determination may be accomplished by a system microcontroller. After a suitable or optimal calibration curve has been determined from the aforementioned fitting procedure, the optical signal from the unknown may be plugged into the calibration equation to determine the pg of THC in the unknown.

In various embodiments, alcohol may be detected simultaneously using, for example, colorimetry and absorbance, or via fluorescence assay similar to the methodology for THC.

BRIEF DESCRIPTION OF THE DRAWINGS

The included drawings are for illustrative purposes and serve only to provide examples of possible structures for the concepts disclosed herein. These drawings in no way limit any changes in form and detail that may be made by one skilled in the art without departing from the spirit and scope of the disclosed embodiments.

DETAILED DESCRIPTION

I. Overview of the Device and Measurement Methodology

Various embodiments described herein provide a handheld device to capture, concentrate, separate, identify, and quantify the level of cannabinoids and in certain embodiments, alcohol (e.g., distilled spirits, ethanol), in exhaled human breath. The device may utilize a fluorescent tag method to identify the cannabinoids.

Figure 1:
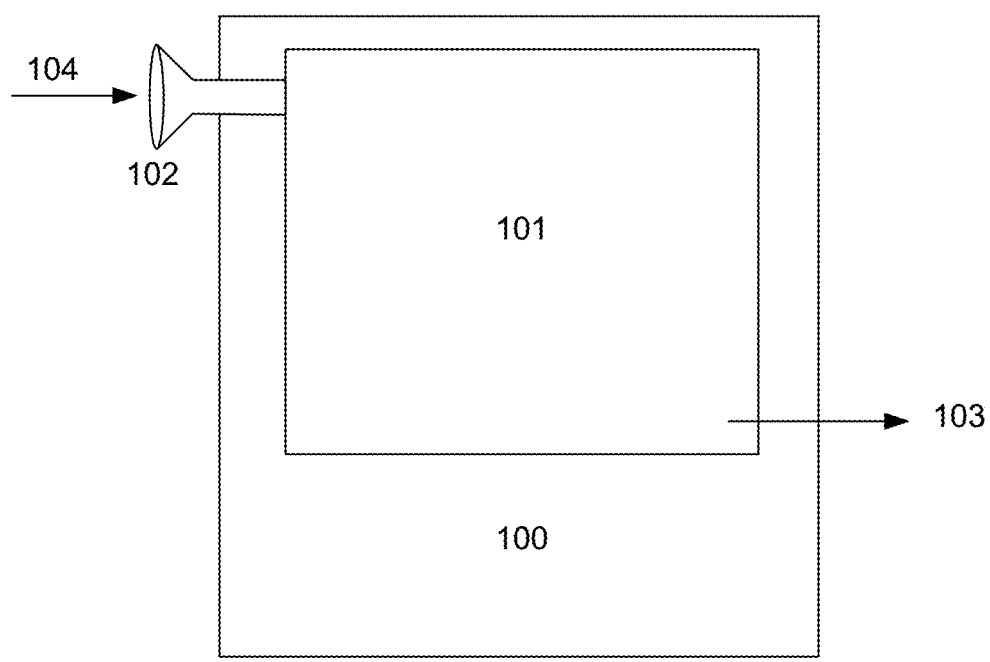
FIG. 1 is a schematic diagram of a breath analysis device.

In various embodiments, the hand-held device may include an analysis unit 100 and a drug testing cartridge 101, as shown schematically in FIG. 1. A test sample may be obtained by having a test subject breathe into a mouthpiece 102; the breath flow 104 may flow through the analysis unit 100 and/or testing cartridge 101 and be vented through vent 103 after analysis or during breath collection. The testing cartridge 101 may be a single-use cartridge. The various steps associated with breath analysis, namely capture, concentration, separation, identification, and quantification, may be arranged to occur in the analysis unit 100 and/or the testing cartridge 101, with the various steps being distributed within or between, or be combined to occur sequentially in or between, the analysis unit 100 and testing cartridge 101. It is to be understood that in some implementations, the detection capabilities discussed herein may be implemented in an alcohol-only detection unit or in a THC-only detection unit instead of a combined unit. A combined unit may, however, provide enhanced functionality.

In the combined THC-alcohol device, breath flow may be arranged (sampled) using one of several different embodiments (see FIGS. 2, 3, 4, 5, and 6), depending on whether the alcohol test occurs before, after, or in conjunction with (simultaneously) the THC breath collection step. FIG. 7 makes clear that the alcohol detection may occur either before or after breath constituent separation.

A. Analysis of Alcohol First

Figure 2:
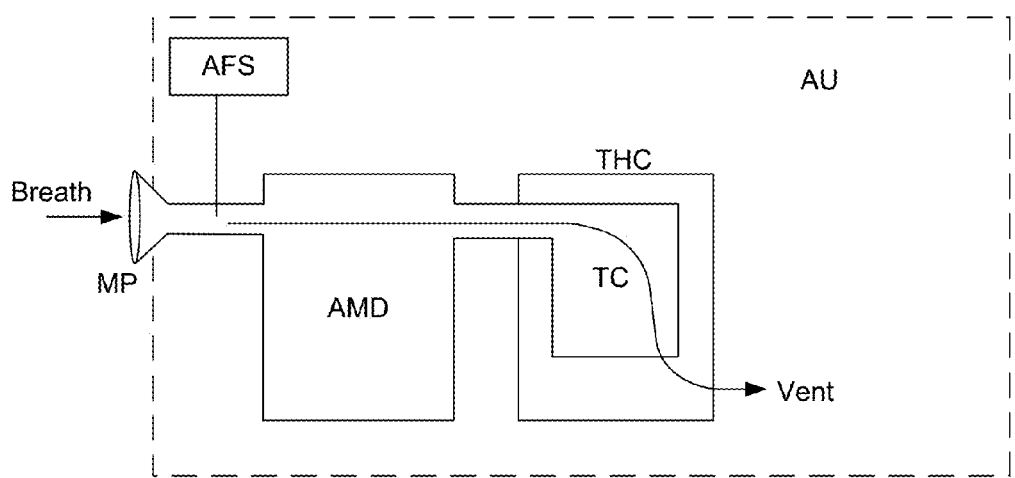
FIG. 2 is a schematic diagram of a combined THC-alcohol breath analysis device.

In one alcohol-first analysis embodiment, as shown in FIG. 2, an analysis unit 200 may have an alcohol measurement device 216 and a THC measuring portion 227 with a testing cartridge 201 connected in series. A subject may breathe a breath sample into a mouthpiece 202; the breath flow 204 may be measured by an air flow sensor 205 before passing through the alcohol measuring device 216 and the THC measuring portion 227 before leaving the analysis unit 200 through a vent 203.

Figure 3:
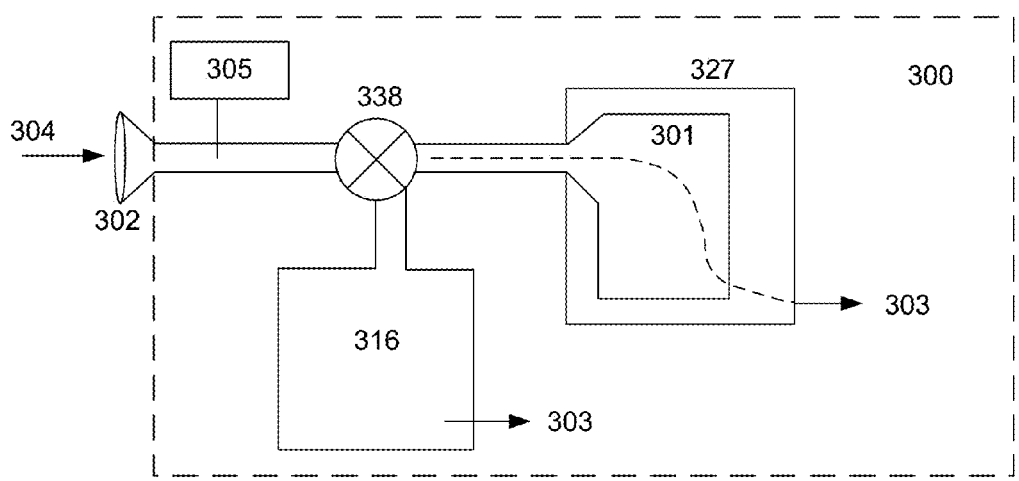
FIG. 3 is a schematic diagram of a combined THC-alcohol breath analysis device.

In another embodiment of the analysis unit, as shown schematically in FIG. 3, breath flow 304 supplied to an analysis unit 300 via a mouthpiece 302 may be completely or partially diverted to an alcohol measuring device 316 using a diverter or metering valve 338 until a sufficient exhaled breath volume needed for alcohol quantification has been reached (for example, 0.5 to 1.1 L, representing the average adult tidal lung volume and expiratory reserve lung volume [20], which is hereby incorporated by reference in its entirety, at least with respect to average lung volumes) from one breath, respectively). The flow diverter valve 338 may then change positions (in response to a command from a system microcontroller) and send the breath flow 304 to a testing cartridge 301 breath collector for THC measurement in a THC measurement portion 327. In the diverter or metering valve configuration, flow control (valve actuation) may be initiated by the system controller in response to a breath flow totalizing sensor (e.g., the cumulative integrated signal from an air flow sensor 305) in the flow path to the alcohol measuring device 316 or in the analysis unit 300. Excess or leftover breath flow that is provided to either the alcohol measuring device 316 or to the THC-measuring portion 327 may be vented via either of vents 303.

For both alcohol and THC quantification, two or three deep breaths may be required, which may range from 1.0-3.3 L, given the limits of tidal and expiratory reserve lung volumes for the average adult. In various embodiments, reaching the desired sampling volume may be indicated to the user using, for example, a display readout, LED, buzzer, or the like.

The totalizing sensor may be an air flow sensor 305 that reads the instantaneous air flow (in units such as L/sec, L/min, cm$^3$/sec, etc.) going through a tube. The air flow sensor 305 may incorporate a hot wire or resistor with a resistance that changes depending on the level of convective cooling due to air flow past the hot wire or resistor (i.e., more air flow=more cooling=more voltage change). The sensor may generate a voltage that is proportional to the air flow at any instant in time. By recording the air flow sensor 305 output over time and integrate it (add it up in time at regular intervals), the total air flow past the air flow sensor 305 may be determined. Thus, the total volume of exhaled breath may be measured.

B. Analysis of THC First

Figure 4:
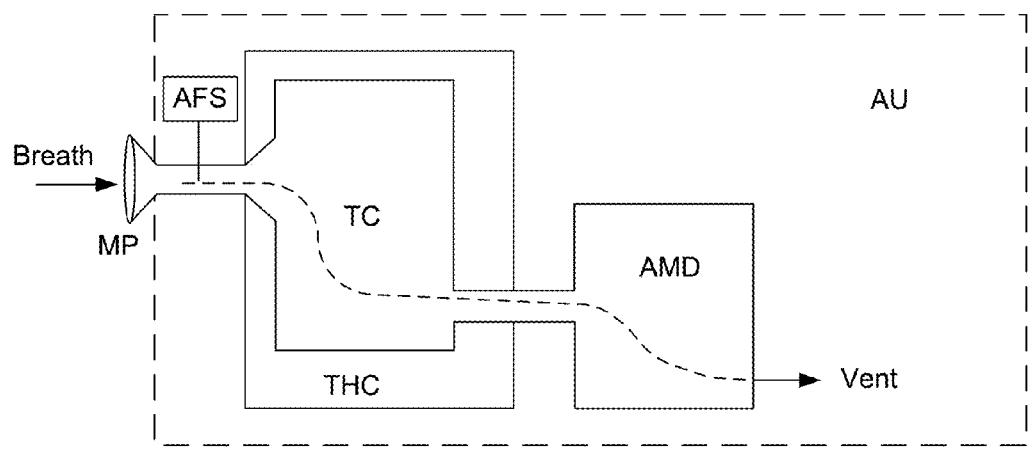
FIG. 4 is a schematic diagram of a combined THC-alcohol breath analysis device.

In one THC-first analysis embodiment, as shown in FIG. 4, an analysis unit 400 may have a THC measuring portion 427 with a testing cartridge 401 connected in series with an alcohol measurement device 416. A subject may breathe a breath sample into a mouthpiece 402; the breath flow 404 may be measured by an air flow sensor 405 before passing through the THC measuring portion 427 and the alcohol measuring device 416 before leaving the analysis unit 400 through a vent 403.

Figure 5:
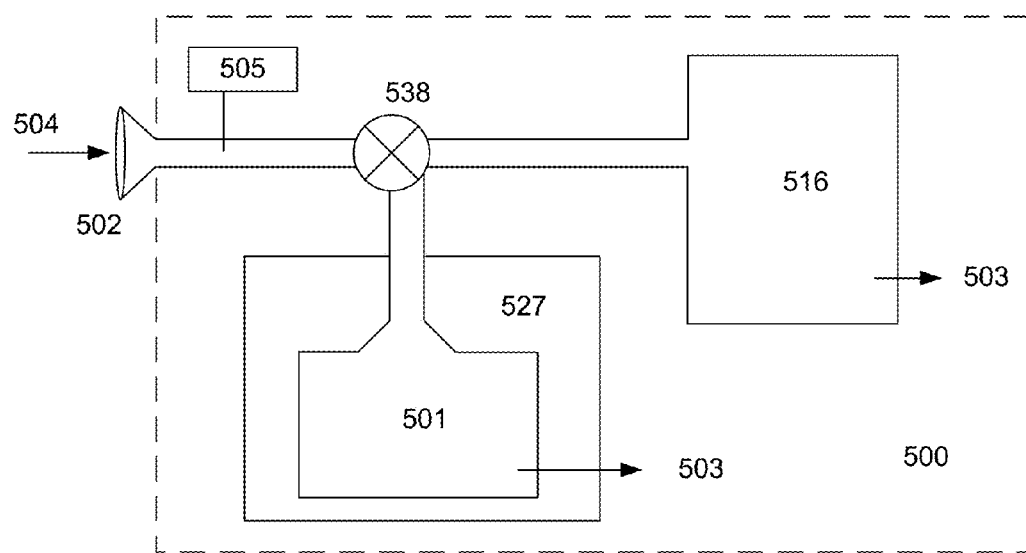
FIG. 5 is a schematic diagram of a combined THC-alcohol breath analysis device.

In another THC-first embodiment, as illustrated schematically in FIG. 5, breath flow 504 from a mouthpiece 502 may be sent to a test cartridge 501 of a THC measuring portion 527 of an analysis unit 500 first. After the THC qualification breath volume has been reached (e.g., 1.0 to 3.3 L), as measured by an air flow sensor 505, a diverter or metering valve 538 may change position and send the breath flow 504 to an alcohol measuring device 516 for analysis. The excess or analyzed breath flow 504 may exit the analysis unit 500 via one or more vents 503.

C. Simultaneous Analysis of THC and Alcohol

Figure 6:
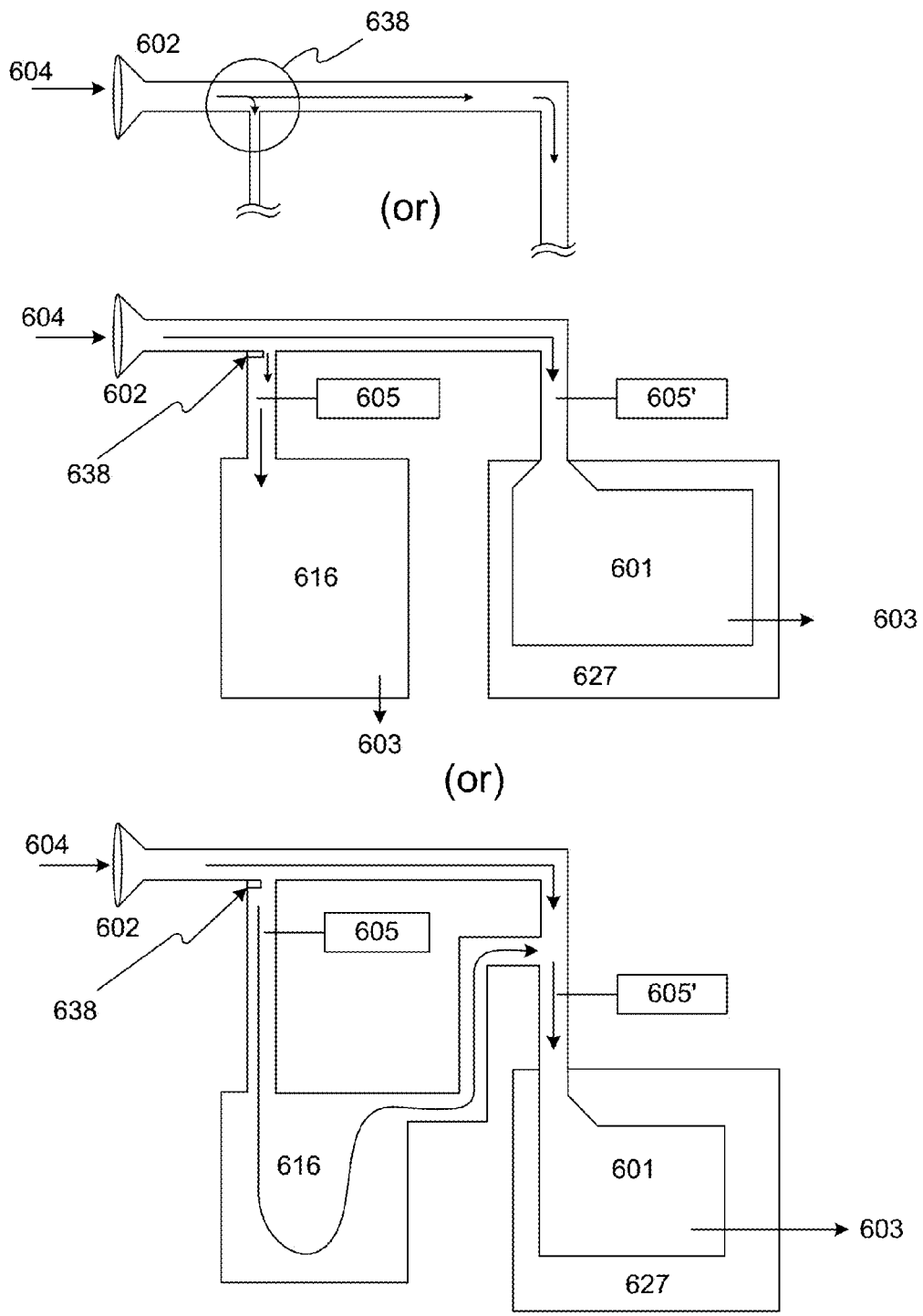
FIG. 6 is a schematic diagram of a combined THC-alcohol breath analysis device.
Figure 7:
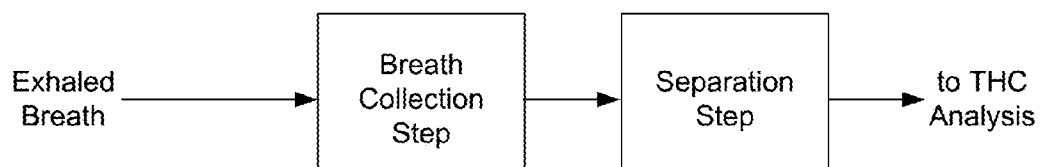
FIG. 7 is a flow chart of an alcohol detection protocol.
Figure 7:
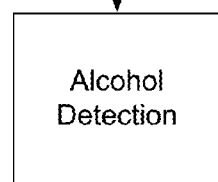
Figure 7:
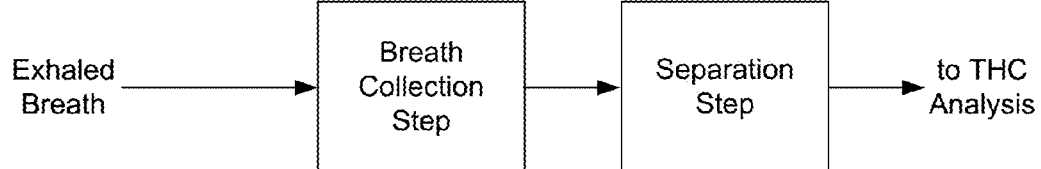
Figure 7:
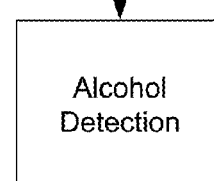

In this embodiment, as illustrated schematically in FIG. 6, an analysis unit may include a sampling orifice or flow bifurcation 638 after a mouthpiece 602 that may divert a portion of overall breath flow 604 to an alcohol measuring device while allowing the remainder of the breath flow 604 to pass to a THC measurement portion. For example, as shown in the middle embodiment of FIG. 6, the mouthpiece 602 may allow breath flow 604 to flow down a tube or passage until it reaches a flow bifurcation 638, which may have a flow constriction that regulates the percentage of the breath flow 604 that flows to the alcohol measuring device 616 while allowing the remaining portion of the overall breath flow 604 to flow into a THC measurement portion 627, which may include a testing cartridge 601. Air flow sensors 605 and 605' may be used to measure the volumetric quantities of the breath flow 604 that are delivered to the alcohol measurement device 616 and the THC measurement portion 627; such measurements may then be used to trigger various operations of the device, e.g., warning the user that sufficient breath sample has been collected. Breath flow 604 entering the alcohol device may be measured for alcohol level; breath leaving the alcohol measurement device may be vented to atmosphere via vents 603 and 603'. The bottom embodiment of FIG. 6 is very similar to the middle embodiment, except that the breath flow 604 that is diverted to the alcohol measurement device 616 may be recombined (after alcohol analysis) with the breath flow 604 sent to the testing cartridge 601 breath collector of the THC measuring portion 627. The recombined breath flow 604 that flows through the THC measuring portion 627 may then be exhausted through vent 603, depending on the embodiment. As mentioned earlier, breath flow totalizing air flow sensors 605 and 605' may be provided for both the diverted alcohol-testing breath flow 604 stream and the breath flow 604 stream going to the testing cartridge 601 breath collector. In the latter recombined configuration, the quantification volume needed for THC testing may be reached in fewer breaths, allowing the simultaneous alcohol-THC test to be conducted more quickly and with fewer required breaths from the test subject.

In various embodiments, as described elsewhere herein, the breath flow may not be bifurcated or split.

D. Summary of Operation

The test subject may exhale several deep breaths into a hand-held breath collection device where breath constituents (excluding non-condensables such as $N_2$, $O_2$, and $CO_2$) may be captured and sequestered. In various embodiments discussed below, breath constituents may be captured and sequestered via adsorption on C18 media, condensation on cold surfaces, and/or dissolution in capture solvent. A variety of embodiments are envisioned for concentration, separation, detection, and quantification of THC, as detailed further below.

Non-condensables are primarily $N_2$, $O_2$, and $CO_2$, which represent almost all of exhaled breath. Water is also exhaled, but will be captured. The catch solvent, if used, is intended to collect most constituents in the exhaled breath except $N_2$, $O_2$, and $CO_2$; both target and non-target species may be captured in the solvent. Other forms of breath constituent capture and sequestration, if used, may be used to similar effect.

In various embodiments, the captured breath constituents, after an elution and concentration step, may be delivered onto a thin layer chromatography (TLC) plate for separation. An appropriate solvent mixture may be applied to a segmented TLC plate (e.g., a TLC "lane" or chromatography region) to spatially separate breath condensate (henceforth referred to as the unknown) into individual components using differential adsorption on the TLC stationary phase. Additional TLC calibration lanes, pre-dosed with known concentrations of THC (or other compound of interest), may be launched simultaneously, via application of the solvent to all of the TLC lanes simultaneously, with the application of the solvent to the unknown TLC lane and serve as references for THC quantification. After a pre-determined separation time (up to several minutes, typically), a fluorescent indicator may be applied to all the TLC lanes at the THC elution location. The indicator may react with any THC present in the elution location to form an adduct which may quench, enhance, or spectrally shift the fluorescence signal.

Figure 25:
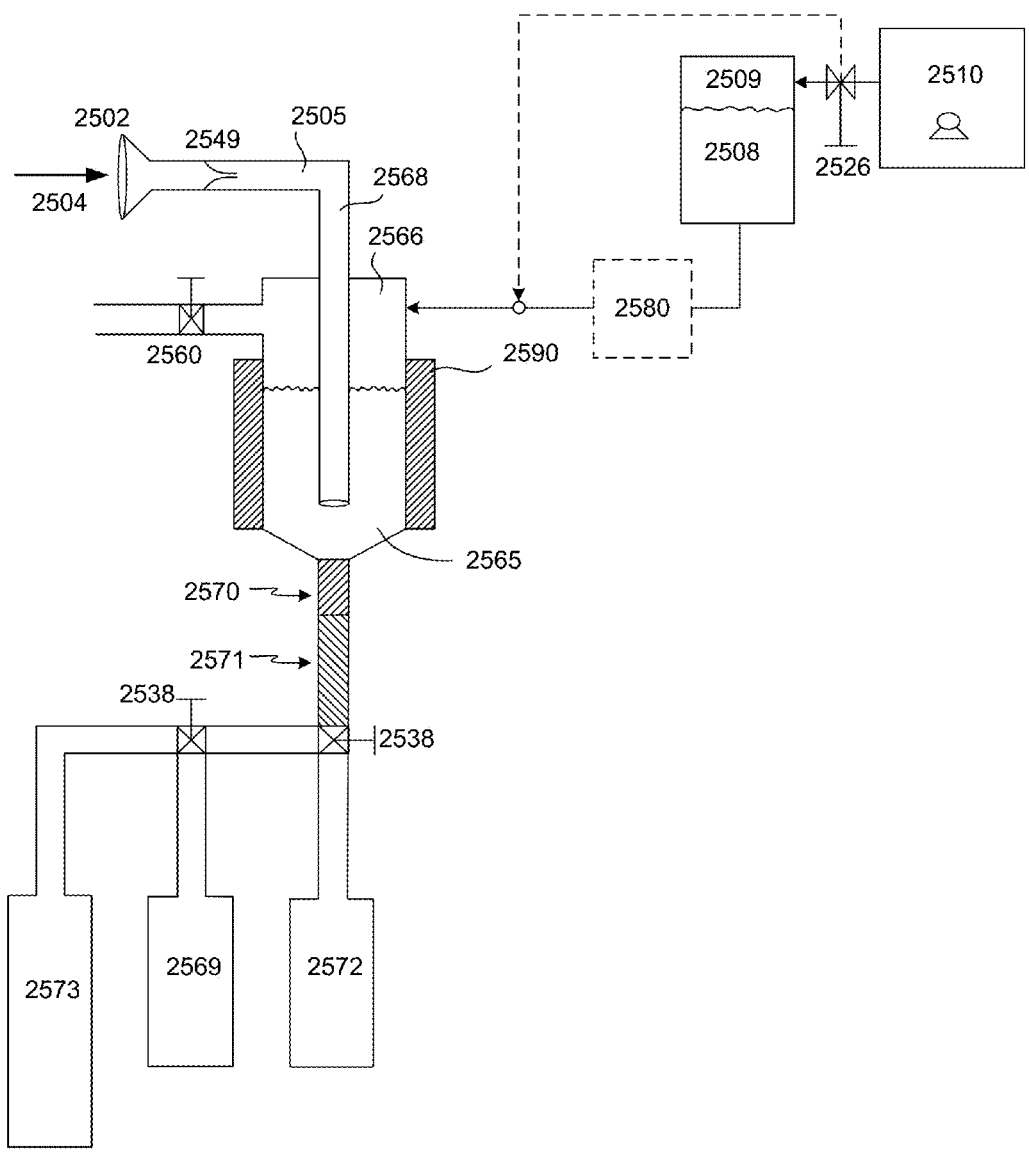
FIG. 25 is a schematic diagram of liquid-based breath capture device.
Figure 26:
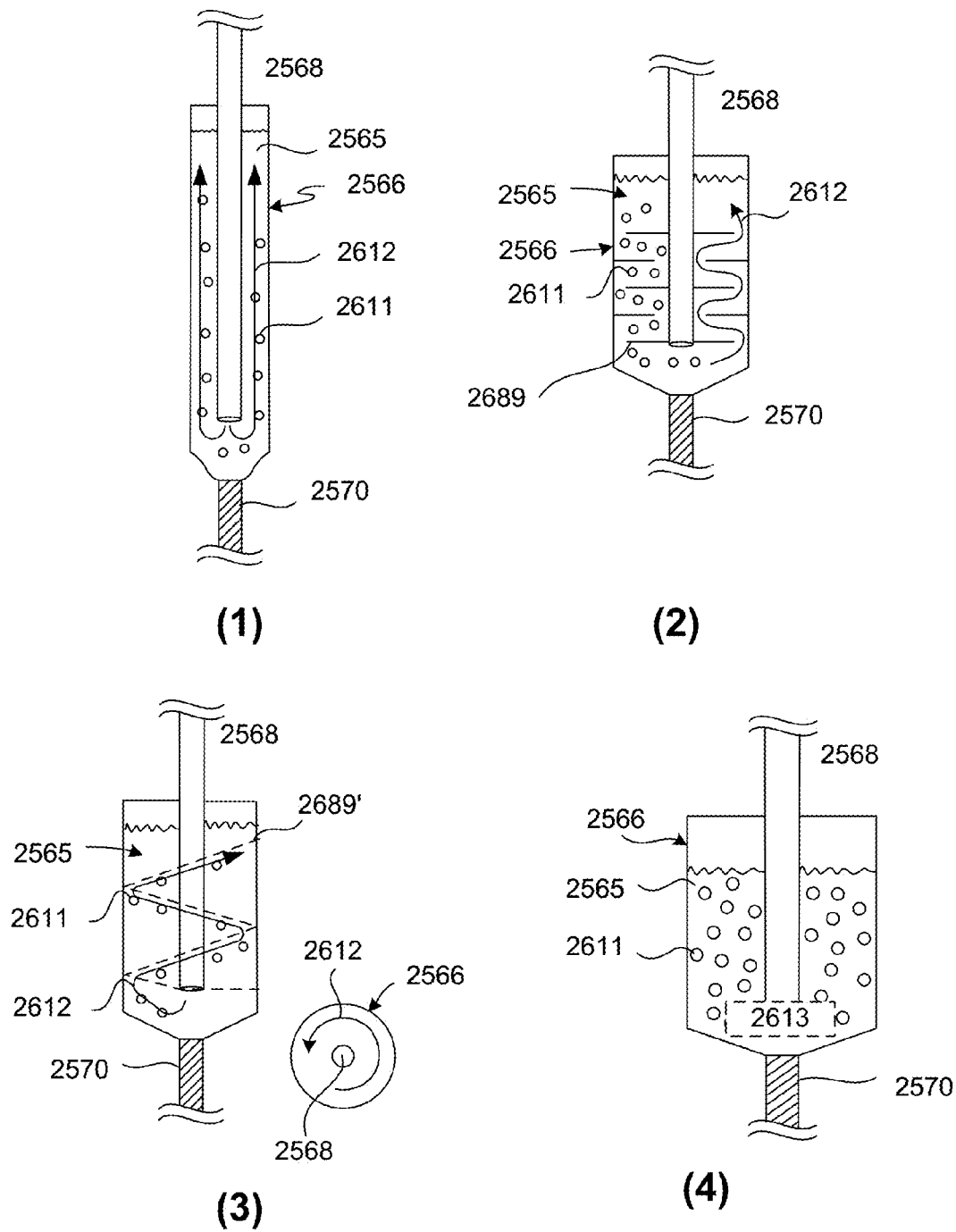
FIG. 26 illustrates various embodiments of a catch solvent reservoir/transfer tube using (1) a long annulus, (2) baffles, (3) cork-screw baffles, and (4) an air diffuser.

In various embodiments, as illustrated in FIGS. 25 and 26 (discussed later), breath constituents may be captured in liquid medium, transferred to lipophilic catch media, and separated via liquid chromatography (LC) using various solvents. A fluorescent indicator or indicators may then be applied to the cannabinoid effluents (see FIG. 39, discussed later, for details) from the LC step, followed by quantification.

The THC adduct may be optically excited (i.e., optically pumped) by exposing the THC adduct solution to light from a diode or diode-pumped solid-state (DPSS) laser or filtered lamp light (e.g., W filament; arc or hollow cathode Hg, Xe, Ar, or $D_2$). Fluorescence, or lack thereof, from the THC adduct and/or unreacted indicator from the unknown and calibration samples may be measured using a photomultiplier tube (e.g., a vacuum device with a photosensitive (photocathode) material which converts photons to electrons), avalanche or other photodiode, or CMOS-based CCD array detector with optical filter(s) that reject (i) pump light (e.g., a filter with optical absorbance >2.0-3.0 at the aforementioned excitation (pump) laser wavelength ±10 nm) and (ii) unwanted emissions from contaminants (e.g., a filter with absorbance >2.0 at the wavelength of contaminant emission(s) ±10 nm); both (i) and (ii) can be accomplished with a single high-wavelength pass filter with cut-off wavelength (e.g., wavelength below which the optical absorbance >2.0-3.0) slightly above (+2-20 nm) the excitation laser and contaminant emission wavelengths. Other light-detection technologies may be used as well in place of, or in addition to, the above-listed technologies. Fluorescence signals from the unknown and calibration samples may then be compared to quantitatively determine the THC level in the unknown. The calibration standards will ensure on-the-fly test validation and accurate determination of THC levels in breath samples.

While certain embodiments may use fluorescence to quantify an amount of a compound in a sample, other embodiments may use other luminescent emissions such as, but not limited to, chemiluminscence, bioluminescence, electroluminescence, electrochemiluminescence, crystalloluminescence, cathodoluminescence, mechanoluminescence, triboluminescence, fractoluminescence, piezoluminescence, sonoluminescence, photoluminescence, phosphorescence, radioluminescence, thermoluminescence, and cryoluminescence. In general, any electromagnetic radiation may be used to stimulate the sample, and any resulting change, emission, discharge or the like in emitted radiation may be measured to quantify an amount of the compound of interest.

The capture, separation, and quantification module (henceforth referred to as the testing cartridge) may be single use and replaced after every field test.

Various embodiments of the testing cartridge may be individually bagged and sealed prior to use, and may have a unique bar code identifier and manufacture date, lot number, etc. for evidentiary purposes.

The hand-held analysis unit may automatically recognize the testing cartridge barcode and store the barcode when the testing cartridge is inserted. As such, every THC or combined THC-alcohol test, its results and unit calibration, time/date, etc. may be electronically recorded into memory and associated with a single testing cartridge that is traceable via barcode.

Figure 8:
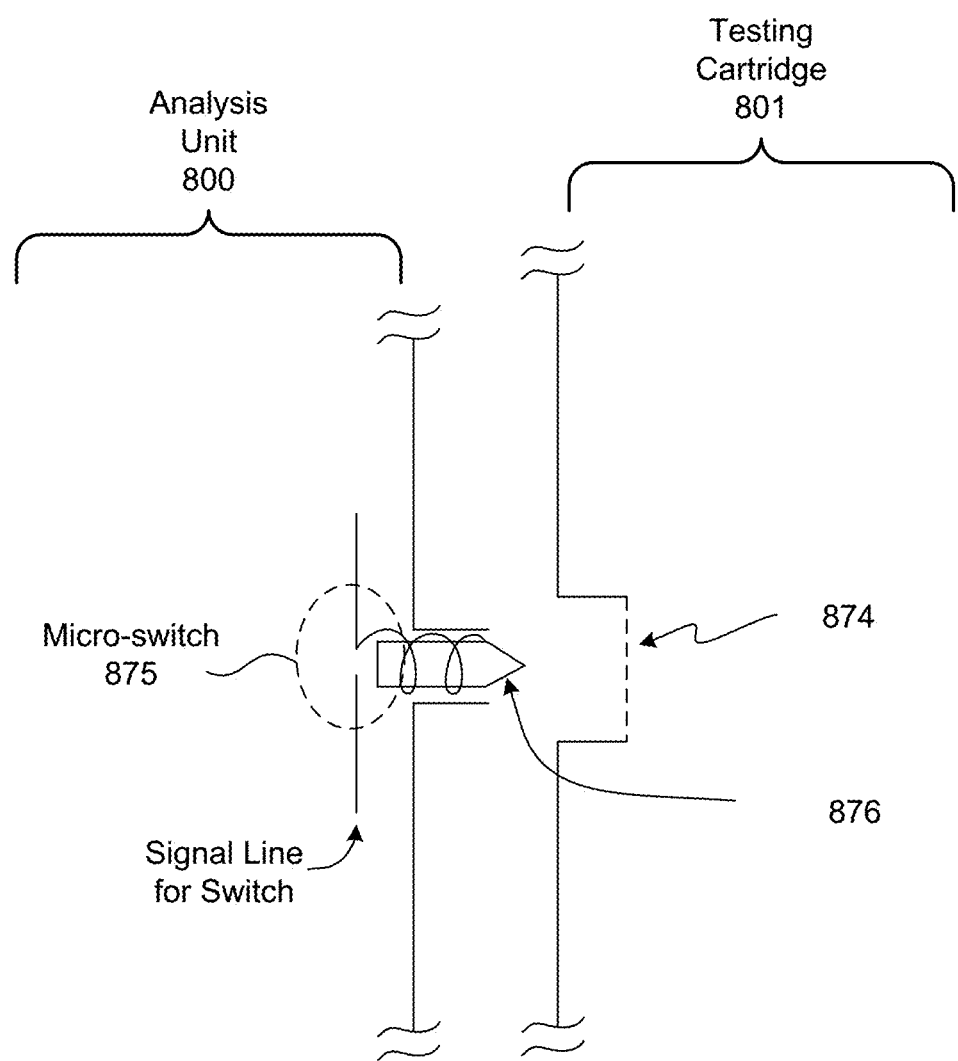
FIG. 8 is a schematic diagram of a device for marking when a cartridge has been used.

When various embodiments of the testing cartridge are inserted into the analysis unit, the testing cartridge may be irreversibly "marked" as having been used to prevent testing cartridges from being used more than one time or improperly inserted into the analysis unit, which could give erroneous results. One example of such a marking system is schematically illustrated in FIG. 8. As shown in FIG. 8, an analysis unit 800 may have a spring-loaded plunger 876 connected to a microswitch 875; the spring-loaded plunger may have a pointed tip that may pierce a recessed plastic membrane 874 in a testing cartridge 801 when the testing cartridge 801 is inserted into the analysis unit 800. The microswitch 875 may be momentarily activated upon inserting the testing cartridge 801, signifying to the analysis unit microcontroller that the testing cartridge 801 is new (unused) and that a breath test can be started. At this point, the plastic membrane 874 on the testing cartridge 801 has been broken by the microswitch plunger 876, irreversibly marking the testing cartridge 874 as having been inserted into the analysis unit 800. If a used testing cartridge 801, which has already had the plastic membrane 874 broken due to prior use or improper insertion, is inserted into the analysis unit 800, the microswitch 875 will not be activated, signaling to the analysis unit microcontroller that the testing cartridge 801 is used, faulty, or improperly inserted. If the microcontroller receives indication that the testing cartridge 801 is used, faulty, or improperly inserted, e.g., as indicated by no momentary activation of the microswitch 875, the analysis unit 800 may be electronically put into lock-out or disabled mode with an accompanying alarm (light, audible warning or tone, etc.) where testing is disabled until a new testing cartridge 801 is properly inserted. Other methods and devices to mark or identify a used testing cartridge 801 as known in the art are considered within the scope of this disclosure.

II. Alcohol Measuring Device and Methodology

Alcohol, henceforth interchangeably referred to as ethanol, in exhaled human breath may be quantified using a colorimetric method that leverages the optical detection system discussed for THC analysis discussed below. Ethanol analysis may be conducted on a portion of breath condensate or a portion of the catch solvent eluted from the catch solvent reservoir. In either of these configurations, ethanol analysis may be conducted on a liquid phase.

In various embodiments, ethanol quantification may occur by coupling ethanol with diazotized p-aminobenzoic acid indicator in alkaline media, to give a colored adduct (diazo ether) with absorbance maximum at 400-440 nm, as detailed in [8], which is hereby incorporated by reference in its entirety and at least with respect to ethanol quantification, and as presented in the following chemical reaction:

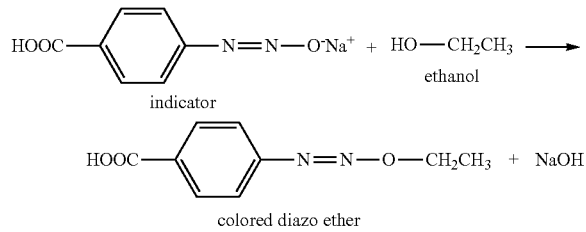

In various embodiments, an additional blue-emitting LED may serve as the light source for absorbance measurements, using an optical detection system similar to that discussed below for THC analysis. In this case, light from the LED may pass through the reaction and optical detection cell (see FIG. 25, for example, for further discussion of such an embodiment), denoted as the alcohol detection cell (ADC), be collected by the fiber coupler (e.g., light emitted by the solution may be collected with a lens and focused into an optical fiber), and be transferred to the optical detector using the optical fiber. The absorbance change in the 400-440 nm spectral range due to the presence of the colored diazo ether in the optical detection cell will be used to quantify the level of the colored benzoic acid-ethanol diazo ether using Beer's law, as presented in Equation 1.

$$A = -\log_{10}\left(\frac{I}{I_0}\right) = \varepsilon L c \qquad \text{Equation 1}$$

where:

A=absorbance of the optical detection cell with colored benzoic acid-ethanol diazo ether; also may be referred to as $A_S$ for ethanol standard absorbance and $A_U$ for unknown ethanol absorbance, I=intensity of laser light passing through the optical detection cell with colored benzoic acid-ethanol diazo ether, $I_0$=intensity of laser light leaving the laser, ∈=molar absorptivity of the colored benzoic acid-ethanol diazo ether, L=optical path length through the optical detection cell, and c=concentration of ethanol.

The measurement procedure may follow the following steps:

(1) $I_0$ is measured with no solution in the optical detection cell.

(2) I is measured after the solution with colored benzoic acid-ethanol diazo ether is put into the optical detection cell.

(3) The absorbance A is measured.

(4) Since ∈ and L are known, the concentration of ethanol, c, is determined from Equation 1.

(5) Once the concentration of ethanol in the optical cell is known, the concentration of ethanol in breath can be determined because the volume of exhaled breath collected is known (e.g., the volume was measured by the air flow sensor).

(6) Once the ethanol concentration in breath is known, a standard dilution factor of 2100:1 is used to convert the ethanol concentration in breath to blood alcohol content (BAC).

In various embodiments, ethanol quantification may occur by reacting ethanol with fast blue B (FBB) or its derivatives using a diazo coupling reaction, shown below, to form a highly colored product that can easily be detected using an optical absorbance measurement. FBB, dissolved in water, may be applied to the breath condensate or catch solvent that is separated out for the alcohol test. FBB may react with ethanol as shown below to make one or both of the products listed on the right, both of which are highly colored. The absorbance of the red azo-ether product solutions may then be measured and quantified with Beer's Law as described above with Equation 1.

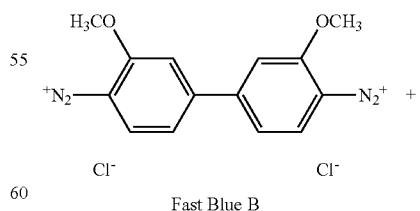

Fast Blue B

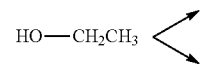

-continued

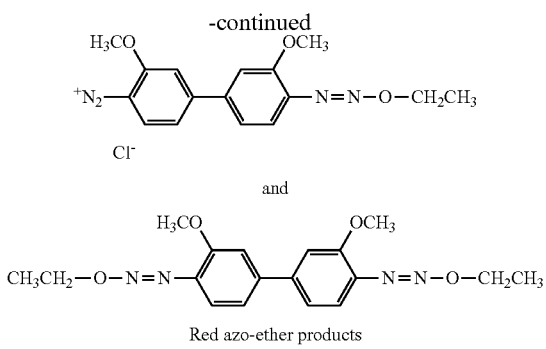

and

Red azo-ether products

Laser light used for THC detection may serve as the light source for absorbance measurements, using the same optical detection system discussed below for THC determination. In this case, light from the laser may pass through the alcohol reaction and optical detection cell, be collected by the fiber coupler, and be transferred to the optical detector. The absorbance increase or decrease due to reaction of ethanol with the indicator may be used to quantify the level of the colored fast blue B-ethanol diazo ether using Beer's law.

The colorimetric indicator (fluorescent indicator) may be of multiple types, including any of the dye families or chemical derivatives involving xanthenes (including rhodamines), cyanines, naphthalenes, coumarins, anthracenes, pyrenes, oxazines, acridines, arylmethines, or tetrapyrroles. Given the backdrop of using the reaction of a diazo functionalized indicator with ethanol to create a colored or fluorescing product, any fluorophore or dye molecule in the chemical families mentioned above could theoretically be used.

In another embodiment, ethanol quantification may occur by coupling ethanol with a diazotized fluorescent indicator (F), as shown below, and be measured by fluorescence assay as discussed below for determination of THC:

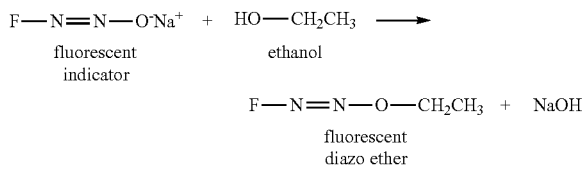

The diazotized fluorescent indicator, dissolved in water, may be applied to the breath condensate or catch solvent that is separated out for the alcohol test. The indicator reacts with ethanol as shown above to make a fluorescent diazo ether. The solution may be excited by the laser, fluorescence intensity is measured, and then compared against calibration samples The aforementioned ethanol tagging embodiment may involve indicator(s) in any one or a combination of the following solvents: pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethyl-phosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, or tetrachloroethylene.

Figure 9:
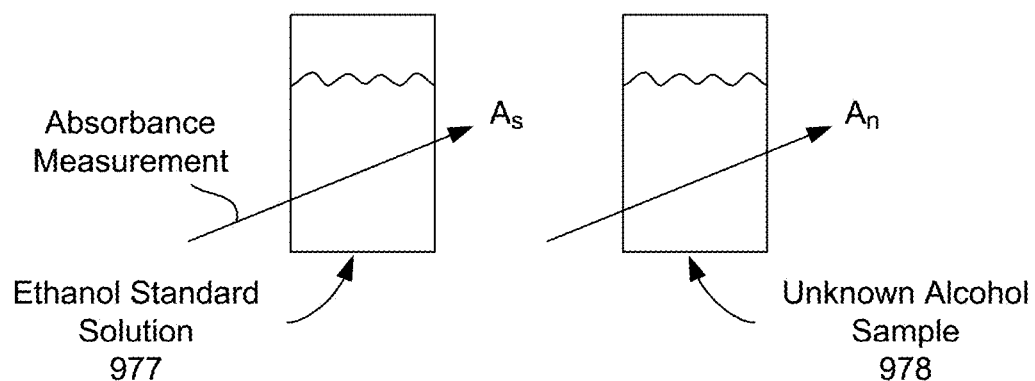
FIG. 9 is a schematic diagram of a method for measuring an absorbance of a standardized solution and an unknown sample.

In all absorbance-based alcohol detection embodiments, as schematically illustrated in FIG. 9, an absorbance "standard" cell 977 containing a known amount of ethanol (e.g., 25-50 µg, equivalent to blood alcohol levels (BAC) of 0.05-0.1%, dissolved in water; total solution volume 1-2 mL), which receives the alcohol indicator, may be present in the testing cartridge alongside an alcohol detection cell for the unknown 978. The absorbance, i.e., $\log(I/I_0)$—outlined in Equation 1, of the alcohol standard and unknown sample may be measured using the methodology described previously. Given that $A_S$, L, and c are known for the alcohol standard, the molar absorptivity, $\in$, of the indicator can be determined using Equation 1. Using this experimentally-determined value of $\in$, the measured absorbance of the unknown $A_U$, and Equation 1, the concentration of alcohol in the unknown can be determined. With this procedure, any chemical or environmental change affecting alcohol indicator sensitivity (e.g., which would affect the molar absorptivity of the indicator or the indicator reactivity with alcohol) will be removed from the measurement, because s is determined at the point of testing.

III. Breath Collection and Concentration

Figure 10:
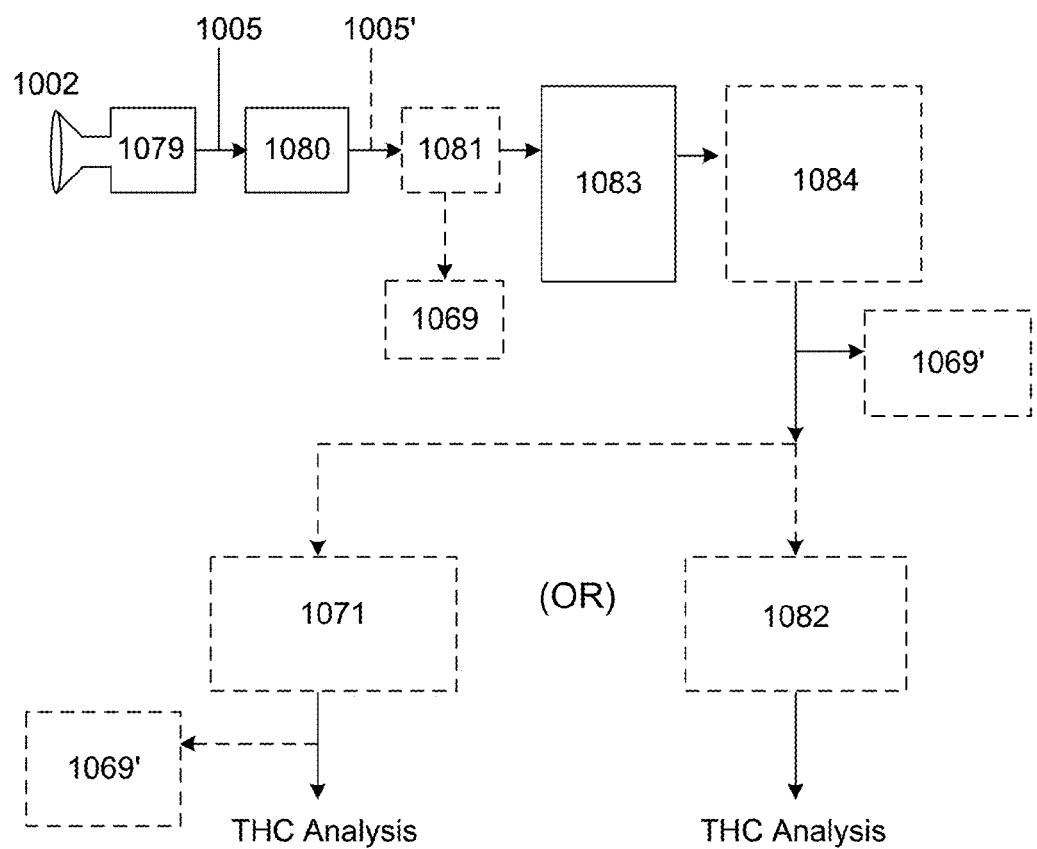
FIG. 10 is a schematic diagram of a testing cartridge.

The following discussion references FIG. 10. A test subject may exhale several deep breaths into a testing cartridge or analysis unit which may include a mouthpiece 1002, a saliva knockout 1079, a check valve 1080, a flow diverter 1081 (in some embodiments), a breath collector 1083 (which may include a filter, catch media, a pre-evacuated volume, electrically-biased metal plate or mesh electrode, or liquid-based breath collection in different embodiments), a breath concentrator 1084 (in some embodiments), and a TLC separator 1082 (in some embodiments) or liquid chromatography media 1071 (in some other embodiments). In implementations that include both THC and alcohol detection capabilities, an alcohol measuring device 1069 may also be included; the flow diverter 1081 may divert some of breath flow 1004 to the alcohol measuring device 1069 in some such implementations. In other such implementations, the alcohol measuring device 1069 may be located in series with the THC-measurement portion; alternate locations of the alcohol measuring device are shown by alcohol measuring devices 1069'. In THC-only implementations, the alcohol measuring device 1069 and the flow diverter 1081 may both be omitted.

Figure 11:
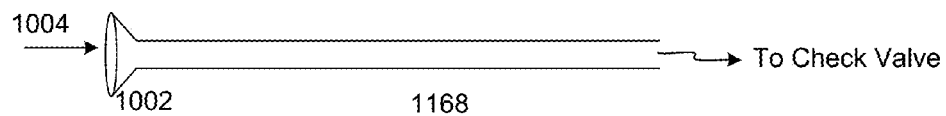
FIG. 11 is a schematic diagram of a long tube saliva knockout device.
Figure 12:
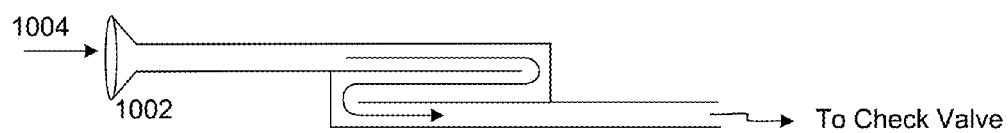
FIG. 12 is a schematic diagram of a long tube saliva knockout device and a flow reversal saliva knockout device.
Figure 13:
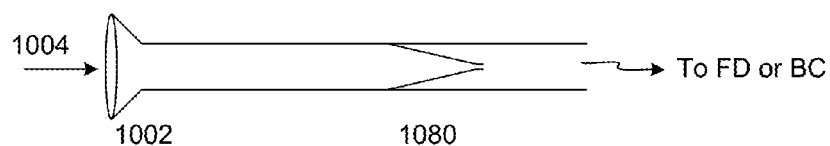
FIG. 13 is a schematic diagram of a mouthpiece having a reed check valve.
Figure 14:
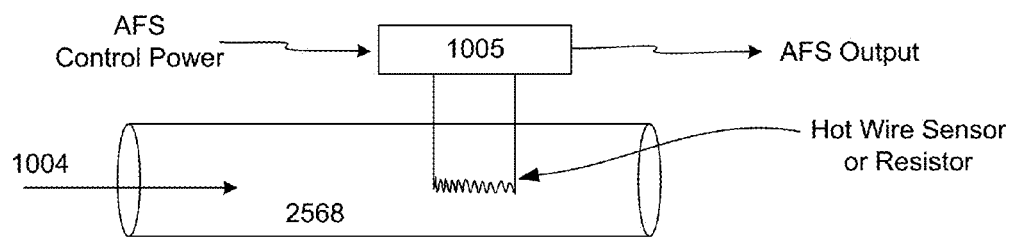
FIG. 14 is a schematic diagram of an air flow sensor in a flow inlet of a breath analysis device.
Figure 15:
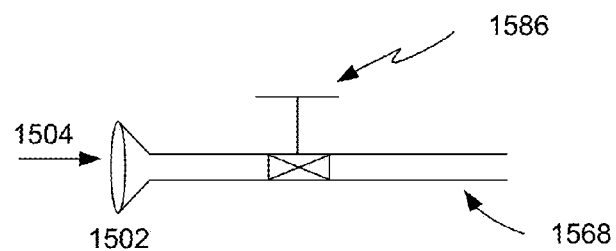
FIG. 15 illustrates an embodiment of a mouthpiece inlet flow disabling device having an electromechanical (solenoid) valve.
Figure 16:
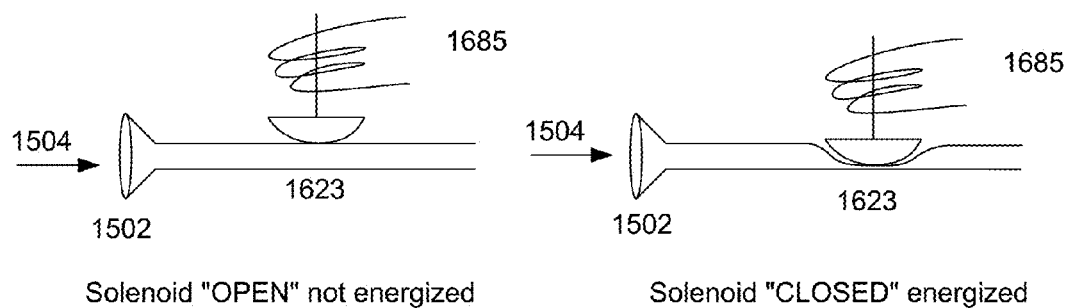
FIG. 16 illustrates an embodiment of a mouthpiece inlet flow disabling device having a tube pinching device.
Figure 17:
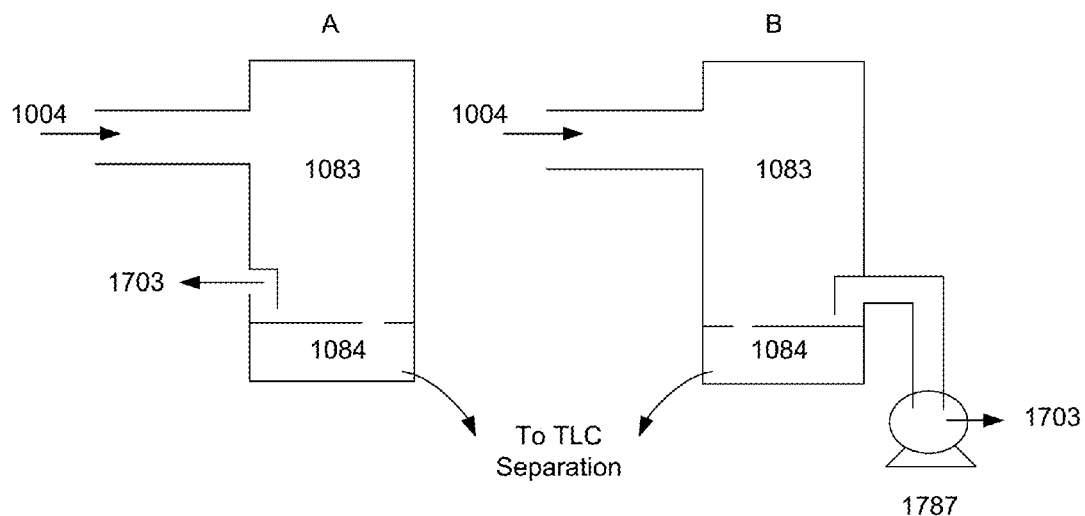
FIG. 17 illustrates various embodiments of catch media (breath collector) using breath pressure and vacuum pump assistance.
Figure 18:
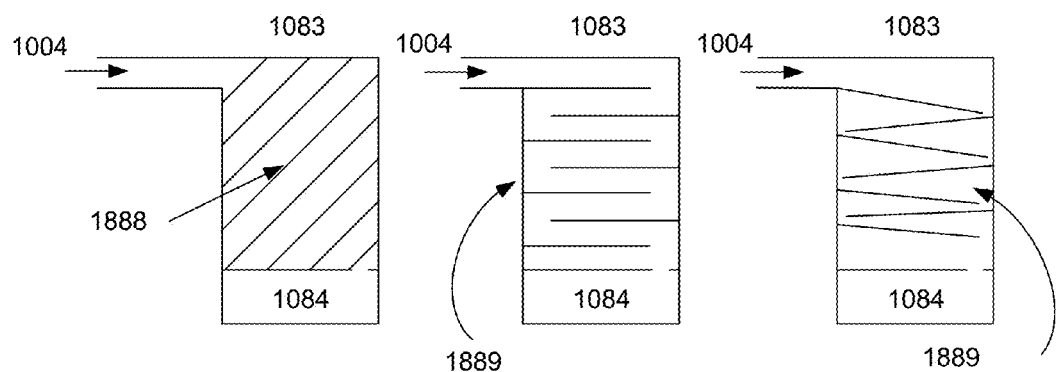
FIG. 18 illustrates various embodiments of catch media having filter media, baffles, and slanted baffles.
Figure 19:
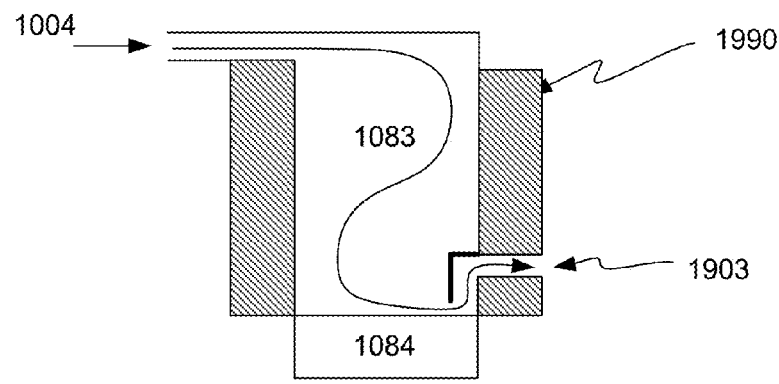
FIG. 19 is a schematic diagram of catch media having a Peltier element for cooling and/or heating.
Figure 20:
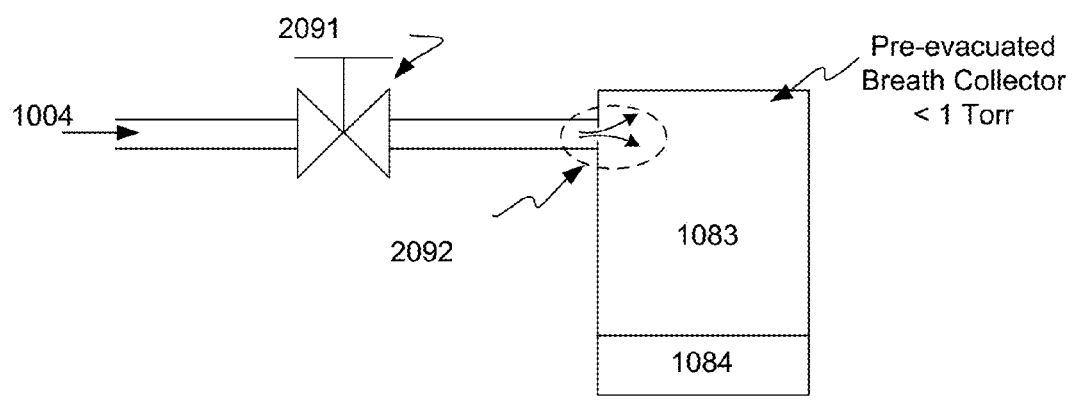
FIG. 20 is a schematic diagram of a breath collector having adiabatic expansion.
Figure 21:
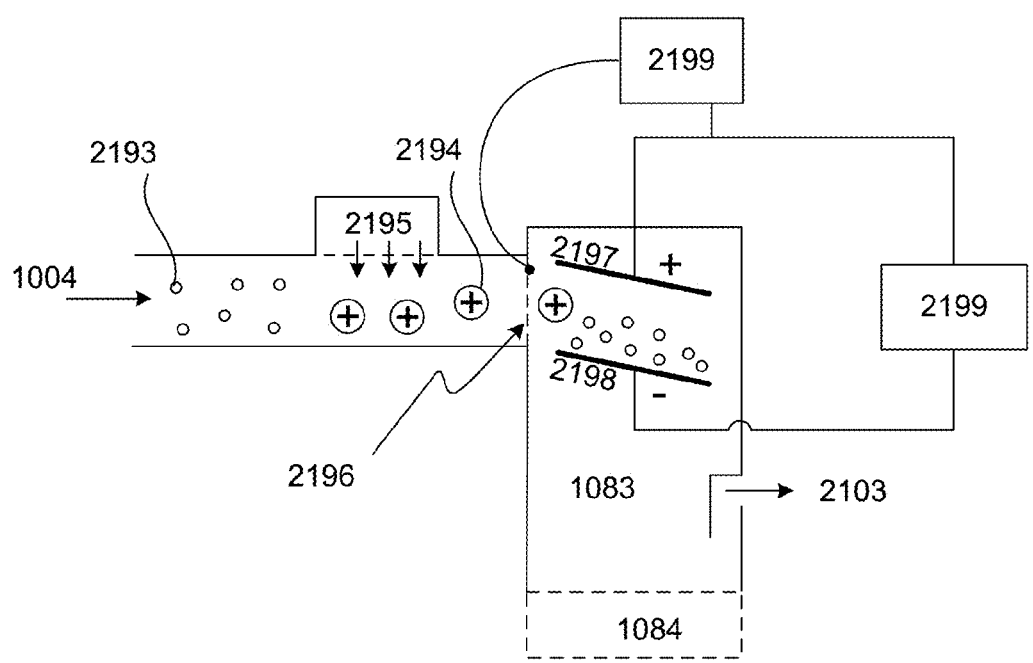
FIG. 21 is a schematic diagram of a breath collector having electrostatic aerosol collection.
Figure 22:
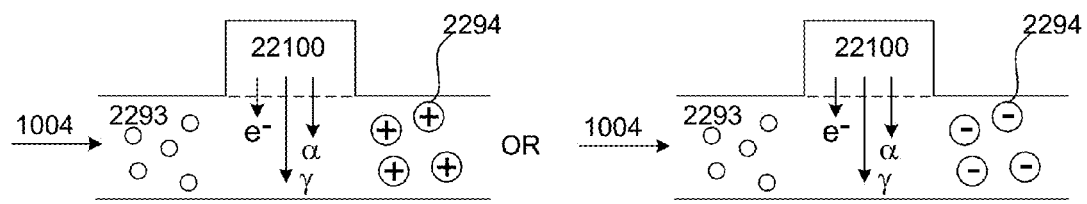
FIG. 22 illustrates an embodiment of an aerosol charger breath collector including a radioactive source.
Figure 23:
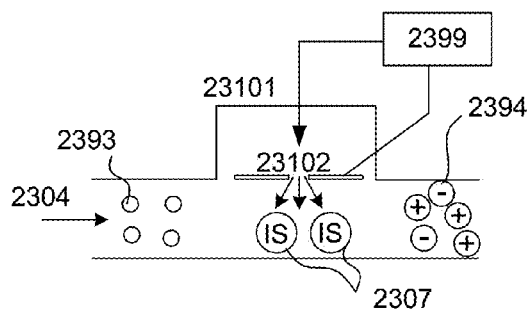
FIG. 23 illustrates an embodiment of an aerosol charger breath collector with a corona discharge.
Figure 24:
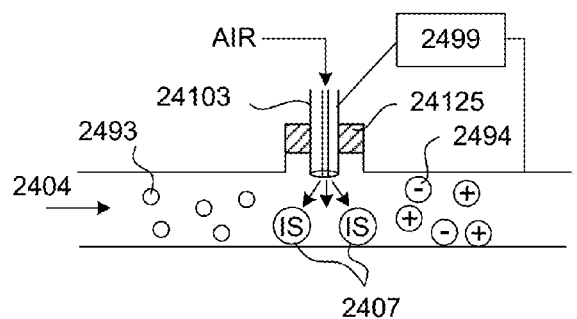
FIG. 24 illustrates an embodiment of an aerosol charger breath collector using atmospheric pressure plasma discharge.

Saliva may be removed from exhaled breath, henceforth referred to as the saliva knockout step (see FIGS. 11 through 13) using, for example, a long tube (FIG. 11) that provides long exposure to the interior surfaces of the transfer tube 1168 to allow the saliva constituents of the breath to condense onto or absorb into the tube walls, a single or multiple flow constriction(s) that act to increase the breath flow velocity through the constriction, thereby lowering the gas temperature and encouraging condensation of the saliva constituents onto the surfaces of the tube/constriction (see, for example, FIG. 13), or one or more flow reversals between the mouthpiece and catch media (multiple collisions of saliva aerosols with the tubing or inner surfaces of the tubing after the mouthpiece will lead to adsorption of saliva aerosols on the tubing surfaces) (See FIG. 12, for example). The saliva knockout 1079 may be implemented either before or after the flow diverter 1081 (and its associated mechanism) in the combined THC-alcohol device embodiments.

The mouthpiece or saliva knockout portion of the testing cartridge may be equipped with a reed-type check valve 1080 (see FIG. 13) to prevent backflow of the breath flow 1004, as well as prohibit the test subject from inhaling through the testing cartridge, which could potentially invalidate a test. In some embodiments, the reed-based check valve 1080 or other device providing similar functionality may also function as the saliva knockout 1079, e.g., as a flow restriction.

A breath flow totalizing sensor (see FIG. 14, denoted as air flow sensor (AFS) 1005 and/or 1005') may be present in a transfer tube 2568 after the backflow prevention check valve 1080 in the alcohol measuring device flow inlet, THC measuring portion flow inlet, or both to measure the instantaneous and total volume exhaled by the subject during the alcohol and/or THC test(s) or the instantaneous and total volume of breath flow that is delivered to the alcohol measuring device, the THC measuring portion, or both in combination. After the pre-determined breath volume needed for alcohol and/or THC quantification has been reached (e.g., 1.0-3.3 L, representing the average adult tidal lung volume and expiratory reserve lung volume from 2-3 exhaled breaths), the unit may signal (light, audible, etc.) that sampling for either or both tests has finished. After the sample finished signal has been generated, the mouthpiece inlet may be disabled (e.g., closed with an electromechanical (solenoid) valve, pinching the flexible transfer tubing with an electromechanical solenoid, taking the unit from the subject, etc.). FIG. 15 depicts an example closure mechanism for a transfer tube 1568 in which a solenoid valve 1586 may be controlled by a controller to shut off breath flow 1504 delivered via mouthpiece 1502 when the air flow sensor 1005 determines that a sufficient breath sample has been obtained. FIG. 16 depicts another example closure mechanism for a transfer tube that uses flexible tubing 1623; a solenoid 1685 may be configured to compress the flexible tubing 1623 in response to a control signal delivered by a controller in response to a measurement of a sufficient breath flow sample by the air flow sensor 1005.

Exhaled breath flow 1004 leaving the mouthpiece 1002/check valve 1080 may then traverse catch media (breath collector 1083) in the test cartridge where the breath constituents are captured (see FIG. 17); breath transfer from the mouthpiece 1002/check valve 1080 may be accomplished via the pressure driving force exerted by the subject under test (left embodiment of FIG. 17), or by using a vacuum pump 1787 to pull the exhaled breath through the filter/catch media (right embodiment of FIG. 17). In different embodiments, breath constituents may be captured on fibrous filter media (see FIG. 18), multi-finned (baffled) catch media (see FIG. 18) that can be cooled and/or heated using an externally-mounted Peltier element (see FIG. 19), or combinations of the two. Cooling of the filter/catch media may be used to encourage condensation of breath constituents during collection and heating may be used to encourage outgassing (removal) of breath constituents from the filter/catch media for subsequent analysis. The breath constituents may then be collected in a breath concentrator 1084 located at the bottom of the breath collector 1083. The remaining breath flow 1004 may then flow out of the breath collector 1083 by way of one or more vents 1703.

The catch media may be configured so the subject under test does not experience considerable pressure resistance during the exhalation process. In the former case, as shown in the left-most embodiment of FIG. 18, this may be accomplished using highly porous (overall porosity=void volume/total volume=0.5-0.9) or thin filter media (<3 mm thick) 1888 in the breath collector 1083 through which the breath flow 1004 is flowed. In the latter case (see, for example, the center and right-most embodiments of FIG. 18), the exhaled breath flow may experience multiple flow reversals through a tortuous catch medium due to flow blockage/diversion by baffles 1889, which may be parallel to one another or sloped, in the breath collector 1083 through which the breath flow 1004 is flowed, which may encourage condensation and/or adsorption of breath constituents (e.g., the more times a gas molecule hits a surfaces, because the flow is reversed by the baffles, the greater probability the gas molecule will stick to that surface).

In the filter media embodiment, adsorption of breath condensate and/or cannabinoids may be enhanced through the use of a chemically-functionalized stationary phase applied to the filter media itself. The stationary phase may include lipophilic molecules (C12-C18, etc., also referred to herein as C18 media) or polymers which show enhanced adsorption or solubility for cannabinoids, due to the chemical compatibility of the long hydrocarbon chain on the THC molecule and the long chain hydrocarbon functionality of the catch media. Breath may leave the catch filter media via a strategically-placed vent 1703 (see FIG. 17 that does not affect the solvent flush and collection process.

In the multi-finned or baffled catch media embodiments (see FIG. 18), an externally-mounted Peltier (thermoelectric) element (as shown by thermoelectric cooler 1990 in FIG. 19, positioned on the outside of the breath collector 1083) may be used to actively cool the catch media and fins below room temperature (e.g., −5 to +15° C., set by the current applied to the Peltier (thermoelectric) element) to encourage condensation of breath constituents during the collection phase. After collection, the Peltier element may be electrically reversed to then heat the catch media and fins to desorb breath constituents. Non-condensable components in breath (e.g., but not limited to $N_2$, $O_2$, and $CO_2$) will leave the catch filter media (because they are non-condensable gases, they will not stick to the media) via a strategically-placed vent 1903 that does not affect the solvent flush and collection process.

In another embodiment (see FIG. 20), the breath collector 1083 in the test cartridge may be an empty container of volume <1 L, configured so as to allow the breath collector 1083 to be hermetically sealed and pre-evacuated to a pressure <1 Torr. A flow restriction or expansion orifice 2092, with additional flow control valve 2091, may be placed between the mouthpiece/check valve and the pre-evacuated breath collector 1083 so as to regulate breath flow 1004 into the breath collector 1083 and encourage adiabatic expansion of the breath flow 1004, thereby cooling the breath flow 1004 and encouraging condensation of breath constituents (excluding $N_2$, $O_2$ and/or $CO_2$) on a filter or catch media in the breath collector 1083. Flow regulation may be accomplished using different size expansion orifices 1092 (e.g., the mass flow rate into the breath collector 1083 may be set by the orifice size and pressure drop across it).

In another embodiment (electrostatic aerosol collection), diagrammed schematically in FIG. 21, exhaled breath flow 1004 and its breath aerosols 2193 leaving the saliva knockout 1079 may pass through a breath collector 1083 having an aerosol charger 2195 and electrostatic precipitator, and a breath concentrator 1084 where breath aerosols 2193 containing THC will be given a net + or − charge using an aerosol charger 2195, e.g., a radioactive emitter (see FIG. 22) or electrical discharge source (see FIGS. 23 and 24). The charged breath aerosols 2194 may subsequently be removed from the exhaled breath flow 2104 via electrostatic deflection using a large electric field (i.e., a force, F=q*E, given by the Lorentz equation may be exerted on the charged aerosol), as may be applied by an aerosol extraction grid electrode 2196, an aerosol deflection electrode 2197, and/or an aerosol collection electrode 2198 powered by one or more high-voltage power supplies 2199. The emitter or electrical discharge source may give the aerosol particles a net + or − charge via electron capture, electron impact ionization, or soft ionization through collisions of the aerosol particle with excited background gas ions, where background gas ions are formed by electron capture or electron impact ionization). In this way, only breath aerosols will be collected; exhaled gases such as $N_2$, $O_2$, and $CO_2$, which represent the majority of the gas load to the analysis unit, will simply pass through the unit (e.g., out of a vent 2103) and not be captured.

The aerosol charger, a system which provides a net + or − charge to the aerosol via electron capture, electron impact ionization, or soft ionization, may be of various types, including, but not limited to a permanent $^{63}Ni$ or $^{241}Am$ source (producing beta, alpha, or gamma radiation) of small size (<<µCi), electrical corona discharge source, or atmospheric pressure plasma discharge.

The electric fields for aerosol defection and capture may be provided by high voltage DC-biasing of metal electrodes, wires, or meshes in or along the breath flow tube or channel, as well as in front of, near, or as part of the TLC separation assembly (see FIG. 21). In another embodiment, electrodes near to or imbedded in the TLC plate itself will attract charged aerosol particles directly to the TLC plate (see FIG. 33, e.g., an electric field will attract the charged aerosol to the TLC plate).

FIG. 22 depicts an aerosol charger that utilizes a radioactive source to charge the breath aerosols. In FIG. 22, breath aerosols 2293 entrained in a breath flow 1004 may be charged by exposure to radioactive source 22100, e.g., $^{63}Ni$, $^{241}Am$, etc., which may emit gamma (γ), beta (e−), and alpha (α) rays or particles that produce charged breath aerosols 2294 as the breath flow 1004 transits past the radioactive source 22100. Such charged breath aerosols 2294 may be either positively charged (left Figure) or negatively charged (right Figure).

FIG. 23 depicts another embodiment of an aerosol charger; this embodiment uses a corona discharge technique to charge the breath aerosols. Breath aerosols 2393 in breath flow 2304 may pass by a corona discharge source 23101, in which a corona discharge electrode 23102 may produce ionized species 2307 and, thus, charged breath aerosols 2394, when powered by a high-voltage power supply 2399.

FIG. 24 depicts yet another embodiment of an aerosol charger; this embodiment uses an atmospheric pressure plasma discharge technique. In FIG. 24, breath flow 2404 with breath aerosols 2493 may flow past a capillary tube 24103 that is supported by an insulator 24125; air may be introduced into the breath flow 2404 by way of the capillary tube 24103. The capillary tube 24103 may be connected to a high-voltage power supply 2499, which may charge the capillary tube 24103 in order to generate a localized plasma using the air in the region of the capillary tube 24103 exit, thereby creating ionized species 2407, which may create charged breath aerosols 2494.

Any of the above aerosol charger embodiments, or other embodiments providing similar functionality, may be used in embodiments that utilize charged aerosols.

In another embodiment, henceforth referred to as the "liquid-based capture method," the catch media may take the form of a solvent or solvent mixture into which the exhaled breath is directed. FIG. 25 depicts a schematic of a liquid-based capture system. All exhaled breath flow 2504 may be directed via the pressure driving force from the subject being tested from the mouthpiece 2502, through a check valve 2549, past an air flow sensor 2505, and into a transfer tube 2568 that extends to the bottom of a catch solvent reservoir 2566. In this way, exhaled breath gas (including breath aerosols and/or saliva) may pass from the transfer tube 2568, into a catch solvent 2565 in the catch solvent reservoir 2566, and rise as gas bubbles in the catch solvent 2565 where breath constituents may be extracted from the gas and into the catch solvent 2565 liquid. Breath constituents in the rising gas bubbles may diffuse across the gas-liquid catch solvent interface due to the concentration gradient that exists between the gas and liquid phases, i.e., breath constituents will dissolve in the liquid due to Fick's Law of diffusion and the chemical potential driving force.

The transfer tube 2568 and the catch solvent reservoir 2566 may be configured in such a way to maximize or increase the contact time between the gas and the liquid to encourage transfer of the breath constituents into the liquid phase. This may be accomplished, as shown in embodiments (1-4) in FIG. 26, using (1) a thin, but long, liquid annulus between the transfer tube 2568 and the catch solvent reservoir 2566, allowing gas bubbles 2611 to follow a generally direct, but long gas bubble path 2612 up to the surface of the catch solvent 2565, (2) an annulus with intermeshed radial baffles 2689 to redirect the gas bubble path 2612 multiple times, thereby increasing the time that gas bubbles 2611 spend in contact with the catch solvent 2565, (3) transfer tube 2568 or catch solvent reservoir 2566 with external (transfer tube) or internal (catch solvent reservoir) Archimedes-screw type baffles 2689' which require gas bubbles 2611 to rise slowly through a long effective gas bubble path 2612 in the catch solvent 2565, (4) a porous diffusing element 2613 at the bottom of the transfer tube 2568 which encourages the formation of fine (small) gas bubbles 2611 in the catch solvent 2565, or any combination of the above. In all these embodiments, smaller gas bubbles and a longer gas bubble-liquid contact time, which may occur when baffles are used to reverse the gas bubble path 2612 or otherwise lengthen the gas bubble path 2612, may lead to greater capture of breath constituents in the catch solvent 2565.

The catch solvent (e.g., 1-3 mL) may be any or a combination of the following components: water, C1-C6 alcohols, C1-C4 ketones or aldehydes, chlorinated hydrocarbons, aromatic hydrocarbons, DMSO, DMF, dioxane, furans, and pH adjusters including, but not limited to acetic, hydrochloric, nitric, sulfuric, and phosphoric acids, acetate salts, alkali metal or alkyl hydroxides, carbonates, or bicarbonates.

The catch solvent reservoir (referring again to FIG. 25) may be equipped with a Peltier-based thermoelectric cooling element 2590 outside to lower the temperature of the catch solvent 2565 (e.g., from 5 to 15° C., set by the current applied to the thermoelectric cooling element, thereby encouraging condensation and transfer of breath constituents into the catch solvent 2565.

The catch solvent reservoir (see FIG. 25) may be equipped with additional lipophilic (e.g., C18 phase loaded on silica or cellulose fibers) catch media 2570 at the bottom of the catch solvent reservoir 2566, followed by liquid chromatography media (functionalized silica resin or particles) for capture and separation of breath constituents, as discussed below. The catch media 2570 is also shown in the embodiments of FIG. 26. The catch media 2570 may be followed by liquid chromatography media 2571, through which the captured catch solvent may be eluted in order to separate out the breath constituents. The separated breath constituents may be diverted, by way of one or more diverter valves 2538, into either an alcohol reaction and detection cell 2569, a THC reaction and detection cell 2572, or a waste reservoir 2573, depending on which breath constituents are exiting the liquid chromatography media 2571. Various liquids, such as the catch solvent 2565 or flush solvent 2508 from a flush solvent reservoir 2509, may be forced through the catch solvent reservoir 2566 by gas pressure supplied from a pressurized gas source 2510, which may be provided by a pump or other mechanism. A check valve 2580 may prevent the pressurized gas that is applied directly to the catch solvent reservoir 2566 from back-driving into the flush solvent reservoir 2509; a three-way valve 2526 may allow such a gas flow to be diverted to the flush solvent reservoir 2509 to drive the flush solvent 2508 through the catch solvent reservoir 2566. An additional valve 2560 may be included to allow air flow from the breath flow 2504 to escape during sample collection to avoid generating a large back pressure in the analysis unit.

After the breath collection phase, an appropriate solvent mixture with minimal or reduced volume may be added to the filter/catch media to release, elute, and concentrate breath constituents. The release process may involve continuous or intermittent application of solvent to the catch media inlet, physical agitation (shaking), and/or be aided by resistive- or Peltier-based heating of the catch media to flush breath constituents into a catch media concentrator near the exit. The solvent mixture may include any combination of the following: water, alcohols (C1-C4 aliphatic or olefinic alcohols and diols, aromatic alcohols and diols), halocarbons (C1-C4 chloro-, fluoro-, or chlorofluorocarbons, both aliphatic and olefinic; aromatic chloro-, fluoro-, or chlorofluorocarbons), C1-C8 alkanes or alkenes, formamide, dimethylformamide, dimethylsulfoxide, ketones, or aldehydes, with pH adjustment using various acids (hydrochloric, sulfuric, acetic, phosphoric, nitric) or bases (NaOH, KOH, amines, ammonium hydroxide).

Figure 27:
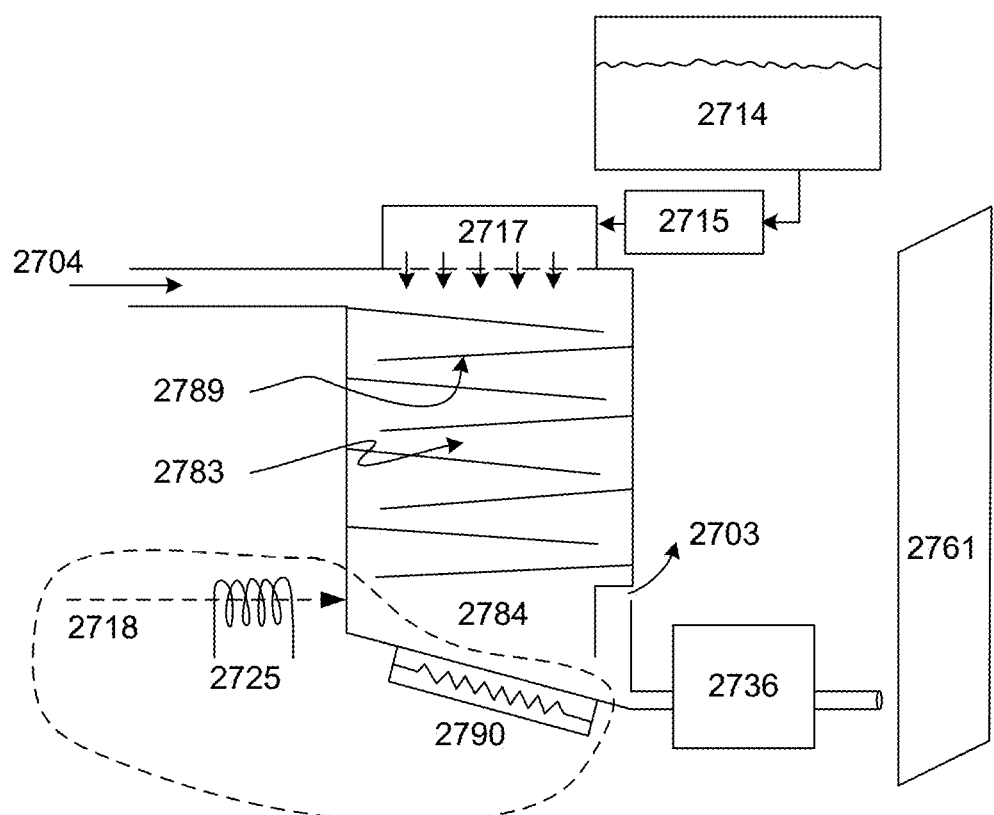
FIG. 27 is a schematic diagram of a device to evaporate solvent from a catch media solvent flush.

In non-liquid capture systems, once the catch media has been flushed via the methods described above, the breath constituent-solvent mixture may be concentrated by evaporating some of the solvent using forced gas flow 2718 and/or resistive or Peltier-based heating 2790, as illustrated in FIG. 27. FIG. 27 shows a breath collector 2783 having baffles 2789 that on which breath constituents from breath flow 2704 may adsorb as the breath flow 2704 transits the breath collector 2783 before exiting the breath collector 2783 via a vent 2703. It is to be understood that any of the breath collector embodiments discussed herein may be used in place of the depicted embodiment. After sufficient breath flow 2704 has been routed through the breath collector 2783, catch solvent from a catch solvent reservoir 2714 may be flowed into the breath collector 2783 via a solvent distributor 2717, which may act to distribute the catch solvent over a large area within the breath collector 2783. The flow of such catch solvent may be controlled by a solvent control system 2715, which may incorporate, for example, a controllable valve or similar fluid flow component. In the case of a liquid-capture system, it may be unnecessary to flush the breath collector with catch solvent as the breath constituents may already be captured within the existing catch solvent used in the liquid capture process; as such, in such embodiments, the solvent reservoir 2714 and related solvent distribution components may be optional. Regardless of the particular breath collection technology used, the breath constituents contained within the catch solvent may be collected in a breath concentrator 2784, which may act, for example, as a catch basin for the solvent.

Once contained in the breath concentrator 2784, the catch solvent may be subjected to an evaporating process, such as the forced gas flow or electrical heating approaches as discussed above. The forced gas flow 2718 (which may optionally be heated by heater 2725) may cause the volatile catch solvent 2565 to evaporate and be swept out of the "strategic vent," leaving behind the breath constituents in a more concentrated form. The heating element 2790 may do the same (i.e., higher temperature leads to solvent evaporation). The goal of this phase of the process is to concentrate breath constituents into a very small volume (~1-100 µL, henceforth referred to as breath condensate or concentrate, as well as the unknown), followed by controlled dosing of the breath condensate to a TLC plate 2761 using a breath concentrate dosing mechanism 2736.

In some embodiments (see FIG. 28, for example), the fluorescent tag or indicator may react with THC only, and, as such, breath concentrate will not need to be separated via liquid chromatography or TLC prior to adding the indicator. In this case, the optical detection methods described below may be applied directly to breath concentrate, because the fluorescent will only come from the fluorescent tag-THC adduct.

In various embodiments, THC calibration standards may be included in the testing cartridge in separate reaction and optical detection cells which are processed with indicator in similar fashion to the breath concentrate.

IV. Dosing of the Thin Layer Chromatography (TLC) Plate

In the liquid-based breath capture method and lipophilic media capture and chromatography separation for liquid-based breath capture embodiments of the device, dosing of the TLC plate, as described in this section, will not be required because these methods incorporate a separation step so separation by TLC is not required.

Figure 29:
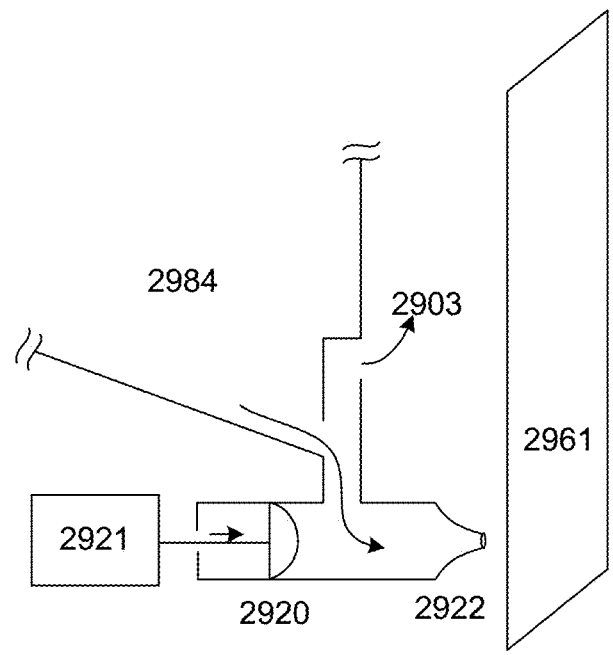
FIG. 29 is a schematic diagram of a breath condensate dosing device having a plunger.
Figure 30:
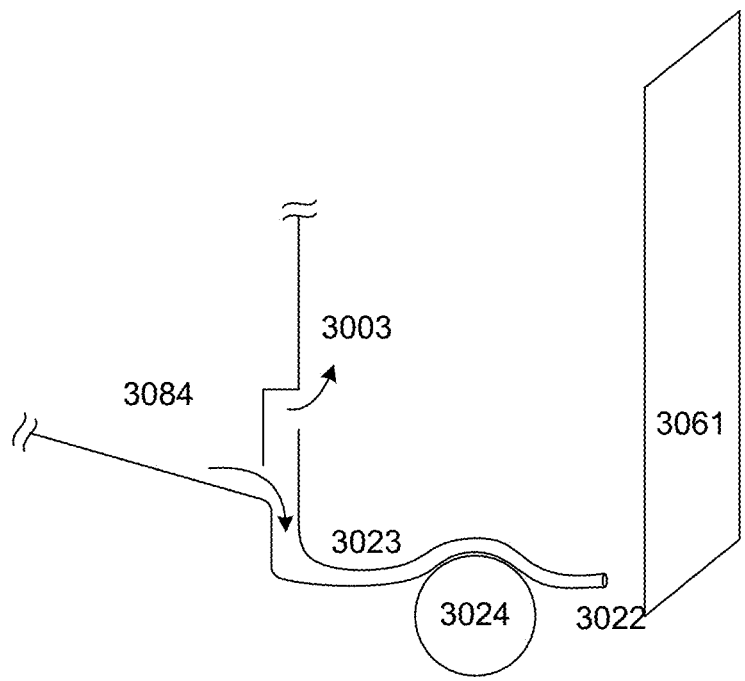
FIG. 30 is a schematic diagram of a breath condensate dosing device having a peristatic pump.

Dosing (application) of breath condensate (e.g., breath constituents dissolved in solvent) onto the TLC lane may be accomplished, as detailed in FIGS. 29 and 30, by forcing the concentrated breath condensate mixture from the breath concentrator through a transfer capillary (denoted as "TC") which connects the catch media condensate reservoir or concentrator to the TLC lane, or by some other mechanism. Several embodiments are envisioned to initiate and carry out the transfer process, some of which are described below.

In FIG. 29, an electromechanical, galvano-, or piezo-actuator 2921 may move a sealed plunger 2920 (e.g., similar to a syringe) located in the base of a breath concentrator 2984 to push and transfer the condensate mixture to and through a transfer capillary 2922, and onto a TLC lane 2961. The analysis system microcontroller may trigger the plunger movement after the breath concentration phase of the analysis has been completed.

Alternatively, as shown in FIG. 30, an electromechanical, galvano-, or piezo-actuator, such as a peristaltic pumping mechanism 3024, may compress (e.g., with a peristaltic motion, see FIG. 30 a flexible tube 3023 from the breath concentrator 3084, which in turn, pushes and transfers the condensate mixture to and through a transfer capillary 3022, and onto a TLC lane 3061. The analysis system microcontroller may trigger the peristaltic pumping action after the breath concentration phase of the analysis has been completed.

Figure 31:
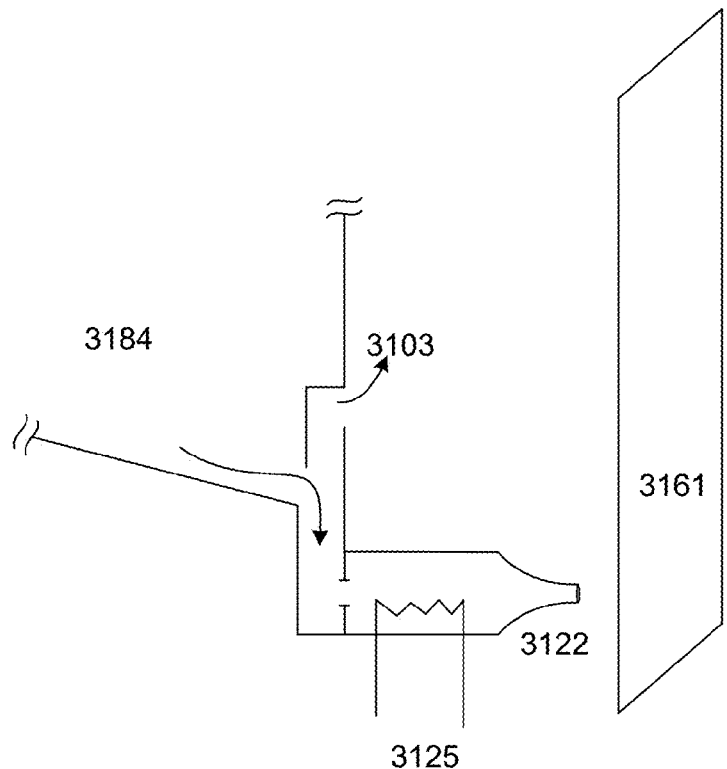
FIG. 31 is a schematic diagram of a breath condensate dosing device having a thermal jet.

Alternatively, as shown in FIG. 31, a heated microtip 3125 near an orifice 3192 may force breath condensate from a concentrator 3184 through the orifice 3192 on demand when the microtip 3125 is heated due to thermal expansion and/or partial vaporization of the catch solvent to create a pressure driving force. The orifice 3192 may be attached to, or be part of, a capillary transfer tube 3122, which may deliver the concentrated condensate to a TLC lane 3161. The analysis system microcontroller may trigger the microtip heater after the breath concentration phase of the analysis has been completed.

Figure 32:
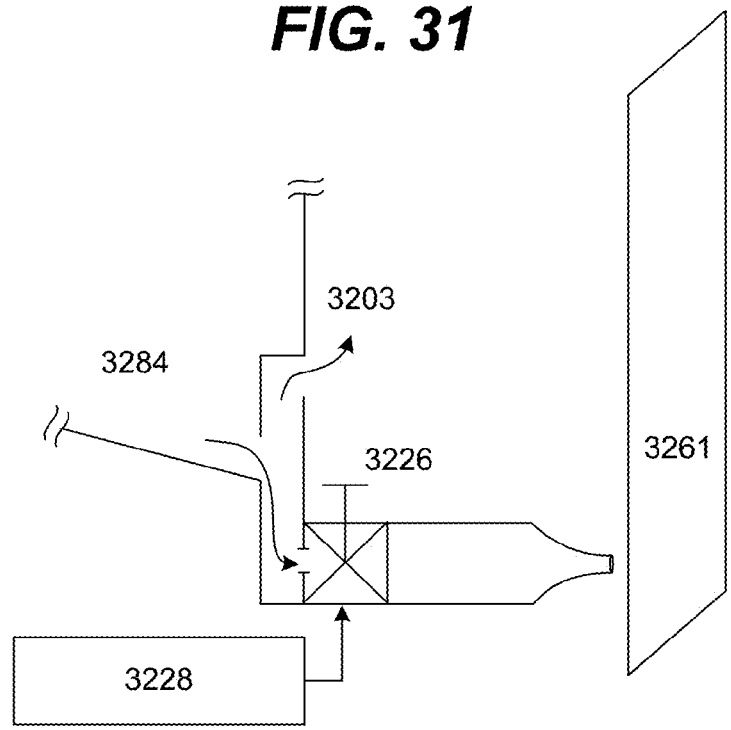
FIG. 32 is a schematic diagram of a breath condensate dosing device having a pressurized gas reservoir.

Alternatively, as shown in FIG. 32, introduction of pressurized gas to the capillary transfer tube may force breath condensate to and through the capillary transfer tube, as detailed in FIG. 32. The analysis system microcontroller may switch a 3-way valve 3226 connected to a pressurized gas reservoir 3228 after the breath concentration phase of the analysis has been completed, forcing the breath condensate from the breath concentrator 3284 onto the TLC lane 3261 via the capillary transfer tube 3222.

In each of the above cases, a vent 2903, 3003, 3103, or 3203 may be included to allow pressure within the concentrators 2984, 3084, 3184, or 3284 to be released.

Figure 33:
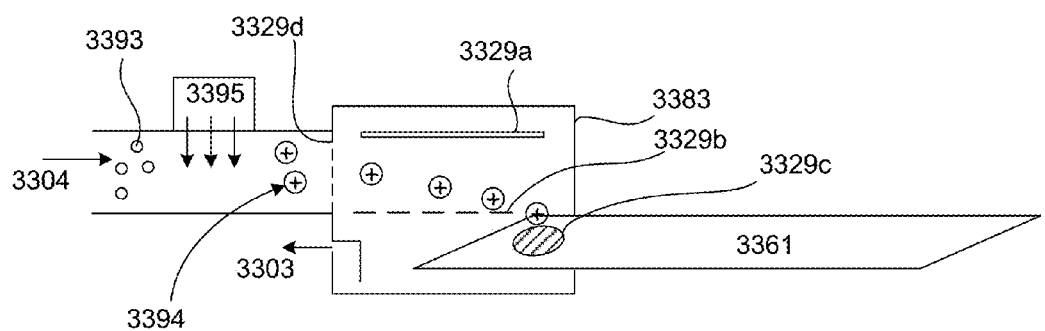
FIG. 33 is a schematic diagram of a breath condensate dosing device having biased electrodes.

In the electrostatic aerosol collection embodiment, the aforementioned concentration step and transfer capillary may not be present; breath aerosols may be transported and focused onto the TLC lane starting position using strategically placed DC-biased metal electrodes, wires, or meshes (see FIG. 33). Charged aerosols may drift to the biased electrode(s), and be deposited on the TLC lane.

In FIG. 33, a breath flow 3304 may be introduced into a breath collector 3383. As the breath flow 3304 passes into the breath collector 3383, breath aerosols 3393 in the breath flow 3304 may be electrically charged by aerosol charger 3395 to form charged breath aerosols 3394. A plurality of high-voltage bias electrodes 3329a-3329d may be arranged within the breath collector 3383 so as to deflect or attract the charged breath aerosols 3394 onto a TLC lane 3361. A vent 3303 may allow the de-aerosolized breath flow 3304 to exit the breath collector 3383.

The transfer capillary diameter and length may be chosen so as to inhibit unintentional filling or transfer of breath condensate to the TLC plate due to capillary forces or necking, e.g., the capillary may be 0.5-2 mm in internal diameter×5-20 mm long.

V. Lipophilic Media Capture and Chromatography Separation for Liquid-Based Breath Capture Referencing FIG. 34, in some liquid-based breath capture systems, the base of a catch solvent reservoir 3466 may be provided that is conical or has a conical base and that is loaded with lipophilic catch media 3470 (0.25-1 mL of C18-like, aliphatic or lipid-based, stationary phase pushed into the bottom of the catch solvent reservoir 3466). Given the chemical similarity of THC and the C18 catch media, e.g., both having long aliphatic carbon chains, THC may adsorb to the catch media 3470. Breath flow 3404 that is supplied via a mouthpiece 3402 may flow past a check valve 3480, such as a reed-type valve, and air flow sensor 3405 before flowing into the catch solvent reservoir 3466 through a transfer tube 3468.

The catch solvent reservoir 3466 may be equipped with a mechanism for pressurizing the catch solvent 3465 that may be contained within the catch solvent reservoir 3466 so as to force the catch solvent 3465, and any captured breath constituents in the catch solvent 3465, through the catch media 3470. Such a mechanism may be provided, for example, by a control valve 34108 (the control valve 34108 may operate in conjunction with one or more other valves V positioned upstream of each of the indicator and flush solvent reservoirs) and micropump 3432 or pressurized gas reservoir 3428, gas pressure regulator 3430, and seal-off valve 3431, as shown in pumping manifold 3410, which may supply pressurized gas above the catch solvent 3465 to push the catch solvent 3465 through the lipophilic catch media 3470, where lipophilic breath constituents in the catch solvent 3465 will be sequestered. The catch solvent 3465 pushed through the lipophilic catch media 3470 by the gas head pressure from the micropump 3432 or pressurized gas reservoir 3428 may also be forced through liquid chromatography media 3471, where the breath constituents may be separated from one another and then routed to the appropriate test cell for analysis (or diverted to waste). For example, a portion of the separated catch solvent 3465 may be supplied to an THC reaction and detection cell 3472 for the unknown and then be subsequently diverted to an alcohol detection cell 3469 for the unknown and/or a waste reservoir 3473. The system microcontroller (not shown) may trigger diverter valves 3438 to direct liquid flow to the alcohol detection cell 3469 or waste reservoir 3473 after a predetermined time (30 sec-2 min) of operation of the micropump or opening of the PGR metering valve 3431.

Figure 34:
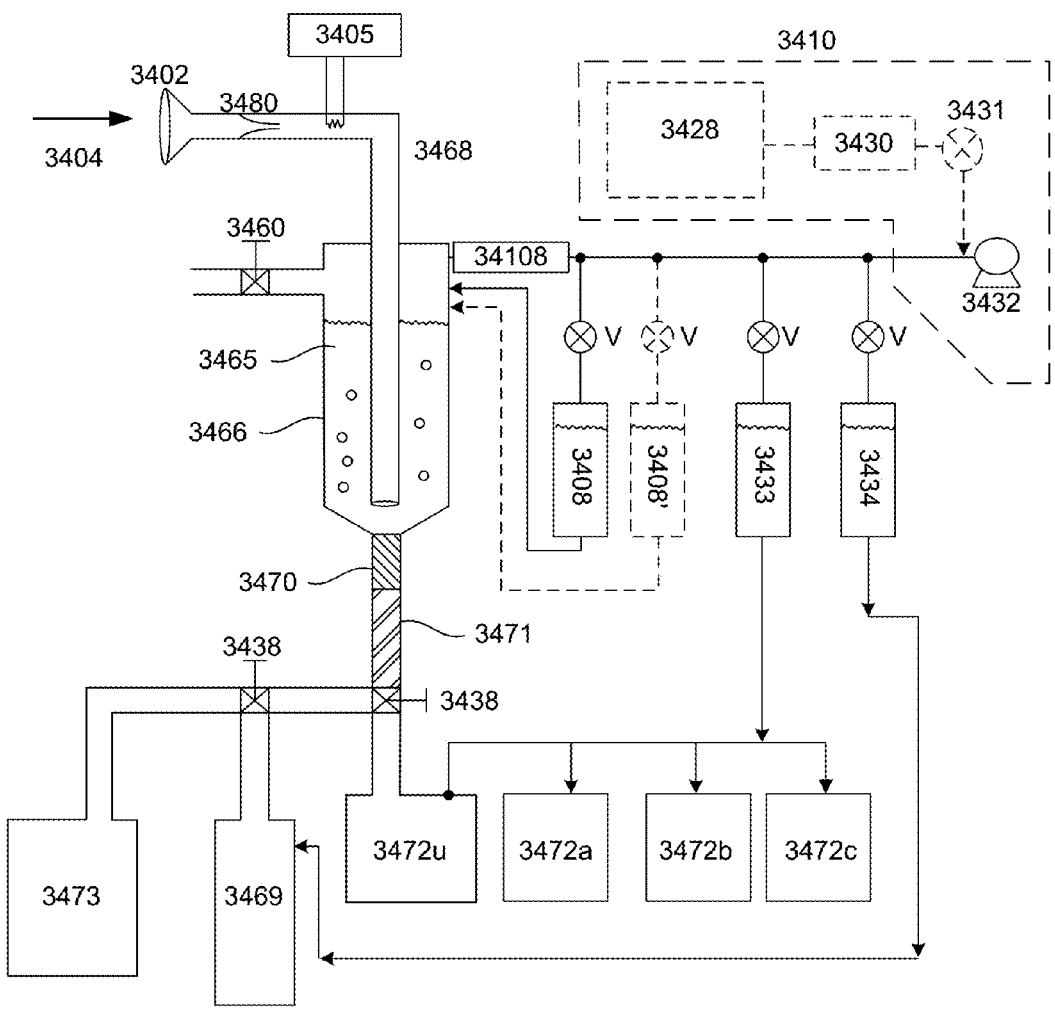
FIG. 34 is a schematic diagram of a breath analysis device having lipophilic media capture and chromatography separation.

Referencing FIG. 34, after the catch solvent 3465 has eluted, (e.g., dictated by the on-time of the micropump 3432 or opening of the metering valve 3431, which results in capture of lipophilic breath constituents on the C18-like media, another flush solvent mixture may be added to the catch solvent reservoir 3466 (e.g., by opening a valve 34107 on a flush solvent #1 reservoir 3408) to remove or desorb the aforementioned lipophilic breath constituents from the C18-like filter media. The micropump or pressurized gas reservoir, now connected to the flush solvent #1 reservoir 3408 by valve V, may force flush solvent #1 into the catch solvent reservoir 3466 due to gas pressure.

The flush solvent #1 may, for example, be any single solvent or mixture of the following solvents: water, C1-C6 alcohols, C1-C4 ketones or aldehydes, chlorinated hydrocarbons, aromatic hydrocarbons, DMSO, DMF, dioxane, furans, and pH adjuster including but not limited to acetic acid, formic acid, hydrochloric acid, nitric acid, sulfuric acid, phosphoric acid, acetate salts, alkali metal or alkyl hydroxides, carbonates, or bicarbonates. The flush solvent #1 may be selected based on higher solubility of THC (or other target compound) in the flush solvent than in the C18-like media. In various embodiments, the flush solvent may incorporate a mixture of water, methanol, and formic acid.

The solvent flush process may be a single step or multiple steps with different solvent mixtures, e.g., flush solvent 3408', which are designed to selectively remove (elute) specific lipophilic breath components from the catch media 3470. Examples include selectively eluting phenolic compounds before cannabinoids or cannabinoid-fluorescent tag adducts, or the reverse, as well as sequential separation of the unreacted fluorescent tag(s), cannabinoids, cannabinoid-fluorescent tag adducts, phenolic compounds, phenolic compound-fluorescent tag adducts, and contaminants from exhaled tobacco smoke and their fluorescent tag adducts, in any order.

Flush solvent may be pushed into the solvent catch reservoir using the aforementioned micropump 3432 or pressurized gas reservoir 3428 to create a gas pressure head (~5-20 psig) above the flush solvent in the flush solvent reservoir 3408. In the pressurized gas reservoir embodiment, the pressurized gas reservoir may be field replaceable, e.g., be a small pressurized gas cylinder, such as the small $CO_2$ cartridges used in wine bottle openers or emergency bicycle tire inflators, and equipped with a micro pressure regulator (GR) and gas metering valve (MV) to the control gas pressure being administered to the catch solvent and/or flush solvent reservoirs 3466 and 3408. The system microcontroller may trigger the metering valve (MV) and valve(s) V to apply pressure to the catch solvent and flush solvent reservoirs as needed in order to achieve the fluid pumping behaviors desired.

The C18-like lipophilic catch media (CM) may be followed by additional C18-like or functionalized silica liquid chromatography media 3471 that is designed to separate cannabinoids from other lipophilic breath constituents such as unreacted fluorescent tag(s), cannabinoid-fluorescent tag adducts, phenolic compounds, phenolic compound-fluorescent tag adducts, and contaminants from exhaled tobacco smoke and their fluorescent tag adducts, aromatic alcohols and/or pyridines which may affect THC quantification downstream.

Flush solvent may be administered to the lipophilic catch media 3470 at a controlled rate (for example, 1-5 mL/min) using the micropump 3432 (e.g., by adjusting the pumping speed using a variable applied voltage or pulse width modulation, supplied by the system microcontroller) or pressurized gas reservoir 3428 by way of the gas metering valve 3431. Administration of flush solvent may affect separation (liquid chromatographic separation) of the lipophilic breath constituents on the liquid chromatography media 3471 so that cannabinoids and contaminants will leave the liquid chromatography media 3471 (e.g., elute from the chromatography media or 'column') at different times.

Flush solvent leaving the liquid chromatography media 3471 may be collected at an appropriate retention time window (for example, less than 10 minutes; alternately when cannabinoids and/or their fluorescent tag adducts, elute from the chromatography media) into a reaction and optical detection cell 3472$u$ for the unknown. Flush solvent leaving the chromatography media before or after the cannabinoid or cannabinoid-fluorescent tag adduct retention time window may be diverted away from the reaction and optical detection cell 3472$u$ into the alcohol detection cell 3469 and/or the waste reservoir 3473 using electromechanical divert valves 3438 operated by the system microcontroller.

Figure 35:
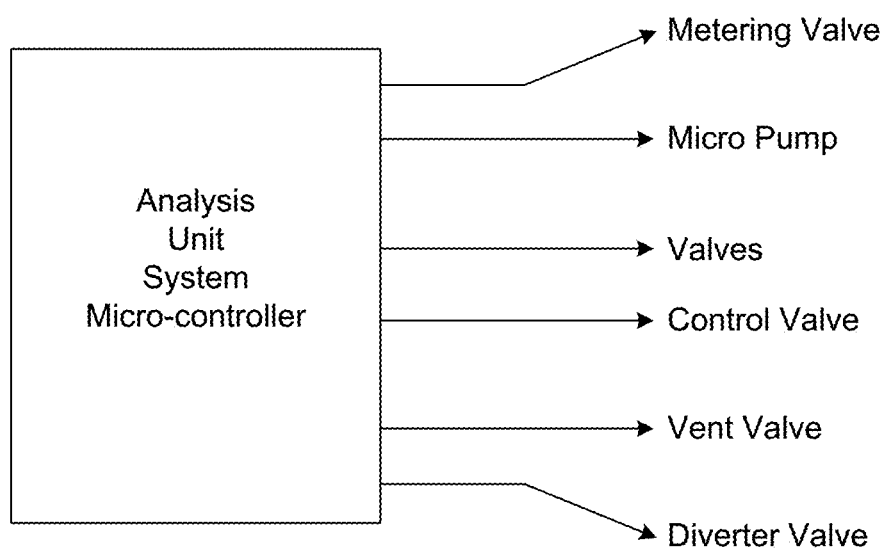
FIG. 35 is schematic diagram of a microcontroller.
Figure 36:
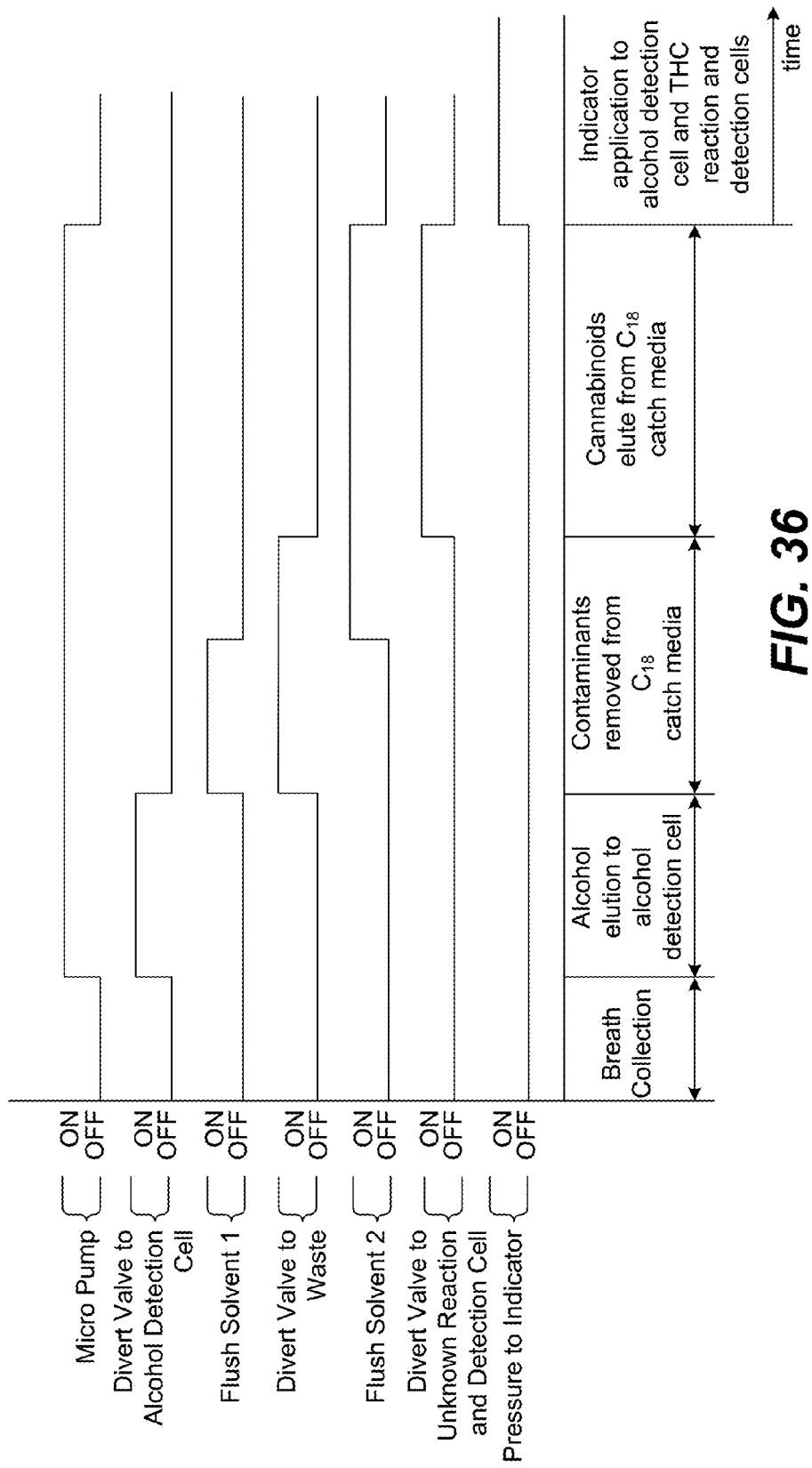
FIG. 36 is a diagram of an electrical control scheme for a breath analysis device.

In various embodiments of the device, such as embodiments illustrated in FIG. 34, any or all of the following components may be electrically coupled and controlled by the analysis unit system microcontroller 34109 (see FIG. 35): the metering valve 3431, the micropump 3432, the valves 34107, the control valve 34108, the vent valve 3460, and the diverter valves 3438, as shown in FIG. 35. An example of an electrical control scheme for the above used during analysis is provided in FIG. 36.

An example, non-limiting procedure for breath capture and chromatographic separation, referenced to FIG. 34 and the above discussion for various embodiments, is as follows:

(1) 0.25 mL fresh C18 catch media 3470 may be loaded into the bottom of the catch solvent reservoir 3466.

(2) C18 preparation, part #1: 2 mL $CH_2Cl_2$ may be loaded into the catch solvent reservoir 3466; liquid may then be pushed through the C18 catch media 3470 using the micropump 3432 or the pressurized gas reservoir 3428, which may pressurize the catch solvent reservoir 3466 through an inlet at the top of the catch solvent reservoir 3466; the micropump 3432 or the pressurized gas reservoir 3428 may be switched off after all of the liquid is eluted through the catch media 3470 (this may be visibly detected by eye or through the use of a sensor, not pictured); this solution is then discarded.

(3) C18 preparation, part #2: 2 mL $CH_3OH$ may then be loaded into the catch solvent reservoir 3466; this liquid may be pushed through the C18 catch media 3470 using the micropump 3432 or the pressurized gas reservoir 3428 in a similar fashion as in the previous operation. The micropump 3432 or the pressurized gas reservoir 3428 may be switched off after all of the liquid is eluted through the catch media 3470 (again, this may be visibly detected by eye or through the use of a sensor); this solution is also discarded.

(4) 1 mL water catch solvent 3465 may then be added to the catch solvent reservoir 3466; the mouthpiece 3402, reed-type check valve 3480, and the transfer tube 3468 may then be attached to CSR.

(5) The subject under test may then exhale approximately 2 deep breaths via the mouthpiece 3402 through the transfer tube 3468 and into the water catch solvent 3465 in the catch solvent reservoir 3466; breath constituents in the exhald breath may then transfer from gas bubbles into the water catch solvent 3465 as the gas bubbles rise in the catch solvent reservoir 3466.

(6) The catch solvent 3465 may then be pushed through the C18 catch media 3470 using the micropump 3432 or the pressurized gas reservoir 3428; the micropump 3432 or pressurized gas reservoir 3428 is switched off after all of the liquid is eluted through the catch media 3470 (again, as visibly detected by eye or using a sensor); cannabinoids and organics in the liquid are then captured on the C18 catch media 3470 during catch solvent 3465 elution; the eluted catch solvent 3465 is discarded.

(7) 1 mL of 2:1 methanol:water mixture may then be added to CSR (this mixture may be obtained from flush solvent reservoir 3408, for example); this mixture may then be pushed through the C18 catch media 3470 using the micropump 3432 or the pressurized gas reservoir 3428 and then discarded. This step may remove organic interferents from the C18 catch media 3470; cannabinoids may stay on the C18 media.

(8) 100 µL of diazo-functionalized Rhodamine-123 indicator (RhNN at 50 µg/mL in $H_2O$) may then be added to the catch solvent reservoir 3466 (the indicator may, for example, be supplied from an indicator reservoir 3433—if alcohol detection is being performed instead, alcohol indicator may be supplied to the alcohol reaction and detection cell 3469 from an alcohol indicator reservoir 3434) and pushed through the C18 catch media in a manner similar to that used in previous steps. This step forms the fluorescing THC adduct, which is retained on the C18 catch media 3470.

(9) 2 mL of $CH_2Cl_2$ elution solvent may then be added to the catch solvent reservoir 3466; this liquid may then be pushed through the C18 catch media 3470 using the micropump 3432 or the pressurized gas reservoir 3428 (this solvent may be supplied, for example, from the flush solvent reservoir 3408'); the fluorescing THC adduct may thereby be stripped off the C18 catch media 3470; the fluorescing THC adduct may fluoresce at 576 nm when pumped by 532 nm green light, such as may be provided to the flushed solution leaving the C18 catch media 3470; the fluorescence may be recorded in real time at the C18 catch media 3470 exit for 1 min during elution of the fluorescing THC adduct. The total signal, e.g., I(t), for 1 min may be integrated to give an overall THC optical "signal." Calibration plots for THC signal levels are presented in FIG. 56 and discussed below.

VI. Thin Layer Chromatography (TLC) Separation

In the liquid-based breath capture method illustrated in FIG. 25 and the lipophilic media capture and chromatography separation for liquid-based breath capture illustrated in FIG. 34, TLC separation, as described in this section, may be optional.

Figure 37:
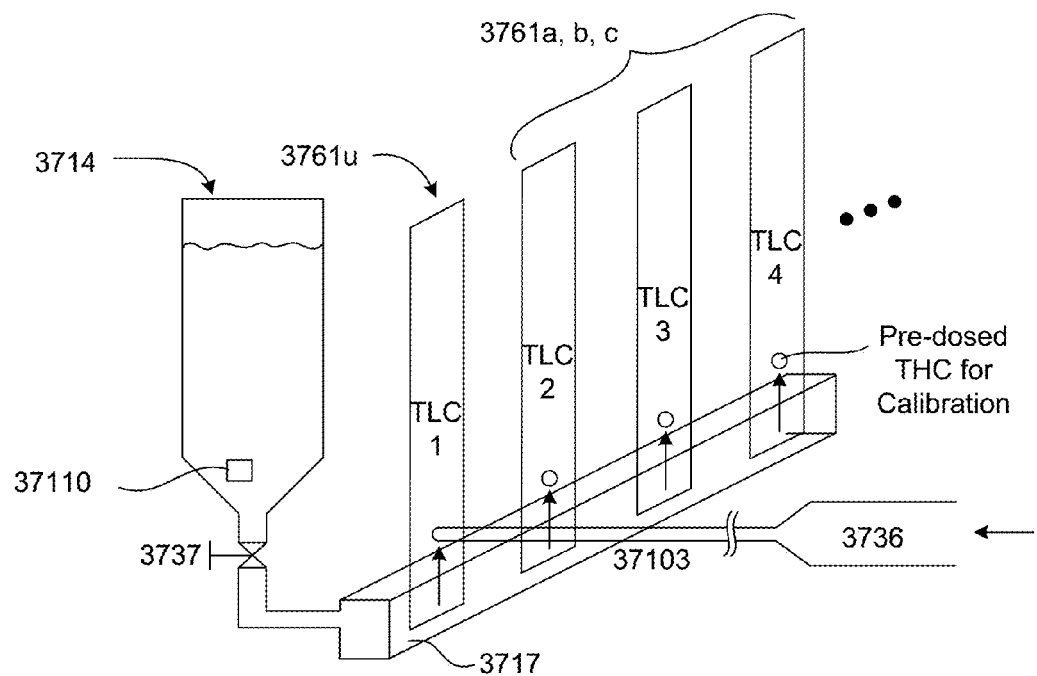
FIG. 37 is a schematic diagram of a thin layer chromatography separation device.

Referencing FIG. 37, after the breath condensate (the unknown) has been dosed onto the TLC plate through a transfer capillary 37103 using a breath concentrate dosing mechanism 3736 as described previously, e.g., such as any of those shown in FIGS. 29 through 33, a TLC solvent mixture (e.g., methanol, water, formic acid, acetone, or dichloromethane, or their mixtures) may be applied via capillary action to all of the TLC lanes 3761 simultaneously (unknown and calibration lanes) via a solvent delivery channel 3717. Solvent may be provided by gravity feed (or other feed mechanism) with a solvent control valve 3737 (which may be operated by the system microcontroller) from a solvent reservoir 3714 that is periodically refilled (e.g., as part of routine maintenance in the field, or at another location as needed by trained personnel). The solvent reservoir 3714 may have a level sensor 37110 that indicates to the system microcontroller when the solvent reservoir 3714 must be refilled.

In various embodiments of FIG. 37, the testing cartridge may include THC calibration lanes 3761a, 3761b, 3761c, etc. (at least one calibration lane, and perhaps as many as 5 or more) on the TLC separator in addition to the unknown THC lane 3761u. In another embodiment where the THC detection and quantification protocol provides an absolute THC signal (i.e., rather than the unknown being compared to and calibrated against several reference samples), the testing cartridge may not contain the TLC calibration lanes.

Solvent from the solvent delivery channel 3717 may be pulled by capillary action into the TLC stationary phases and effect separation (elution) of the unknown and calibration samples down the length of the TLC lanes.

After a pre-determined separation (elution) time (e.g., 10 s-5 min) which is adequate to spatially separate cannabinoids from other breath condensate constituents, the TLC lanes may be ready for indicator application.

VII. Indicator Application, Detection, and Quantification

Fluorescent indicator or indicators, or radio-labeled indicators (indicators containing a radioactive emitter), may be applied directly (e.g., by adding the radioactive indicator solution) to breath constituents in solution (various embodiments illustrated in FIGS. 25, 28, and 34 where the cannabinoid-fluorescent tag adduct may be formed before liquid chromatographic separation by adding the indicator to the solvent with breath constituents), breath condensate (various embodiments illustrated in FIG. 27 related to TLC separation), or the eluted cannabinoid fraction (i.e., the flush solvent leaving the C18 media which contains cannabinoids) from liquid chromatography separation (various embodiment illustrated in FIG. 34, where the fluorescent adduct is formed after separation), as discussed below.

Relating to various embodiments such as that illustrated in FIGS. 27 and 37, once TLC separation has been completed, a fluorescent indicator may be locally applied to all of the TLC lanes 3761 at THC elution locations 37111 using an indicator dosing mechanism. Several embodiments of an indicator dosing mechanism are described below.

Figure 38:
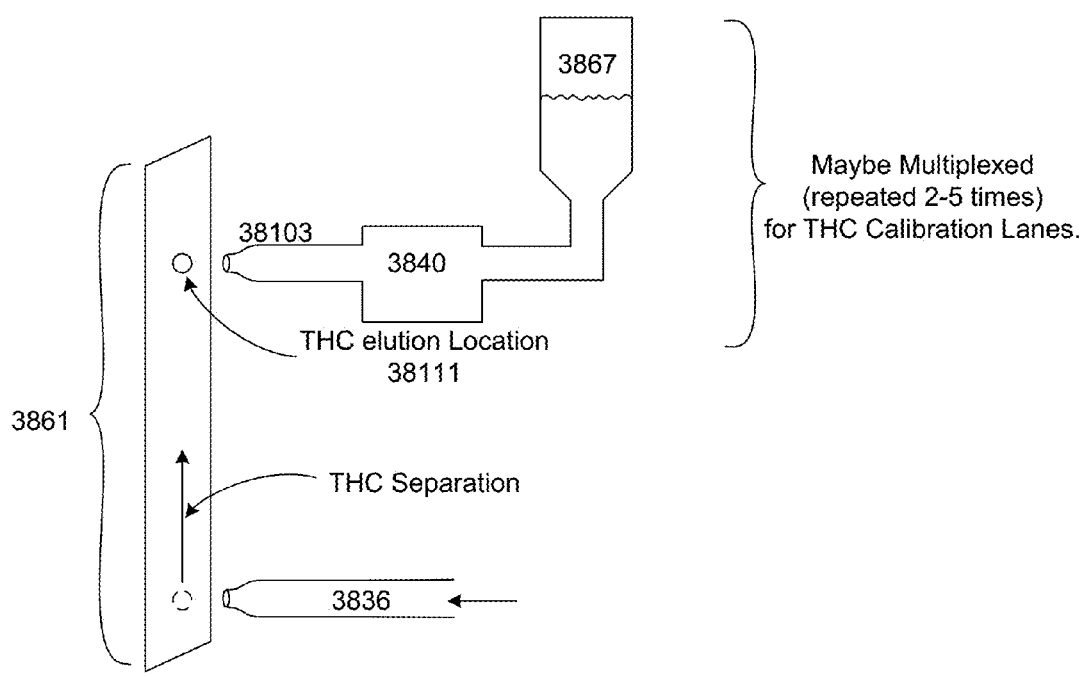
FIG. 38 is a schematic diagram of an indicator application device for a thin layer chromatography lane.

As shown in FIG. 38, the indicator may be pre-dissolved in solvent and delivered from an indicator reservoir 3867 by an indicator dosing mechanism 3840 via capillary delivery tube 38103 or hypodermic needle to a THC elution location 38111. An electromechanical, galvano, or piezo actuator may push a sealed plunger in the reservoir to force the indicator solution into the capillary delivery tube 38103 and onto the THC elution location 38111, in a manner similar to that discussed previously with respect to the dosing of breath concentrate as discussed with respect to FIG. 29.

Alternatively, a heated microtip or resistor (e.g., inside the indicator reservoir, flash heated to 80-150° C. by passing current through the tip or a resistor, also known as Joule heating) may force indicator solution through the transfer capillary 38103 and onto the TLC plate 3861 at the THC elution location 38111, similar to the breath concentrate dosing mechanism discussed previously with respect to FIG. 31. For reference, breath constituents/breath concentrate may be applied to the TLC plate 3861 via a breath concentrate dosing mechanism 3836, as discussed previously.

Alternatively, introduction of pressurized gas to the indicator reservoir may force indicator solution to and through the transfer capillary and onto the THC elution location, similar to the breath concentrate dosing mechanism discussed previously with respect to FIG. 32.

Alternatively, the indicator in solid form may be pre-applied at a level of 1-100 µg to the TLC lanes during manufacturing at the THC elution location. When the THC elutes to the specified location, the diazo-modified fluorophore reaction with THC may occur to form a fluorescing THC adduct.

Figure 28:
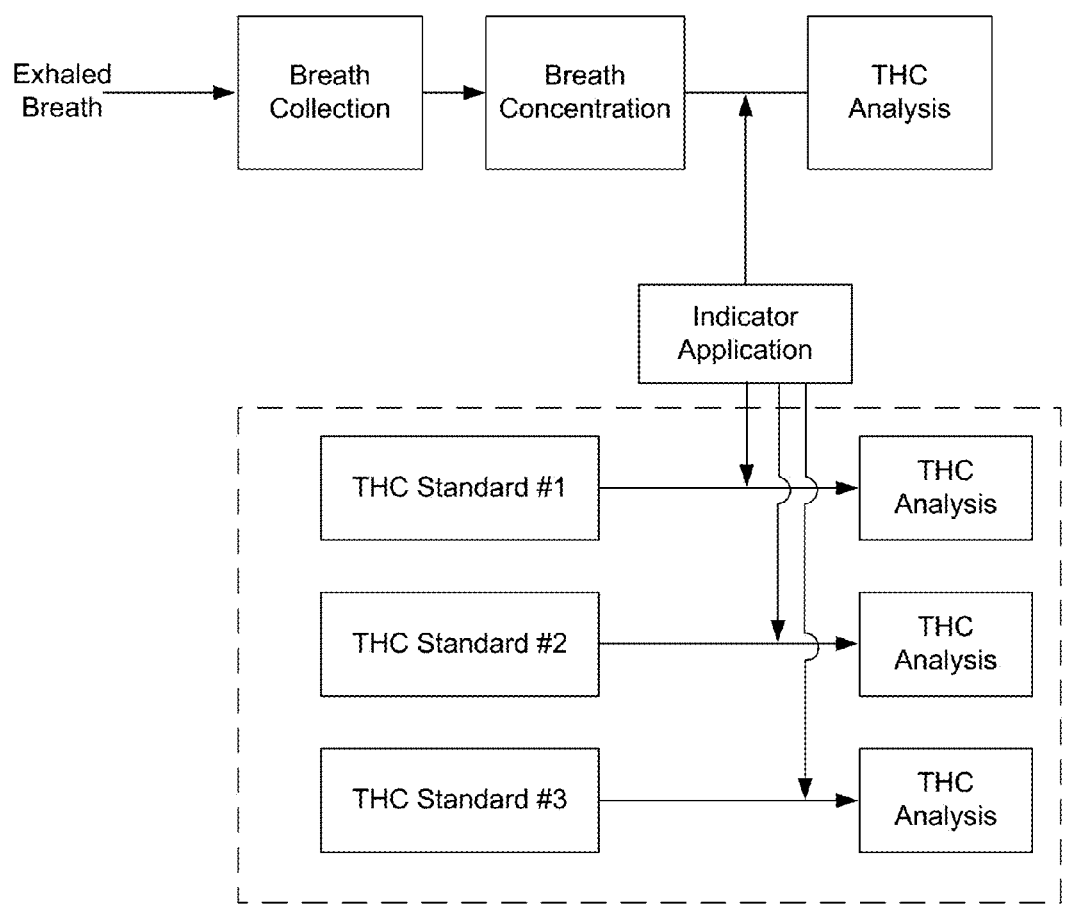
FIG. 28 is a flow chart of a THC analysis embodiment.
Figure 39:
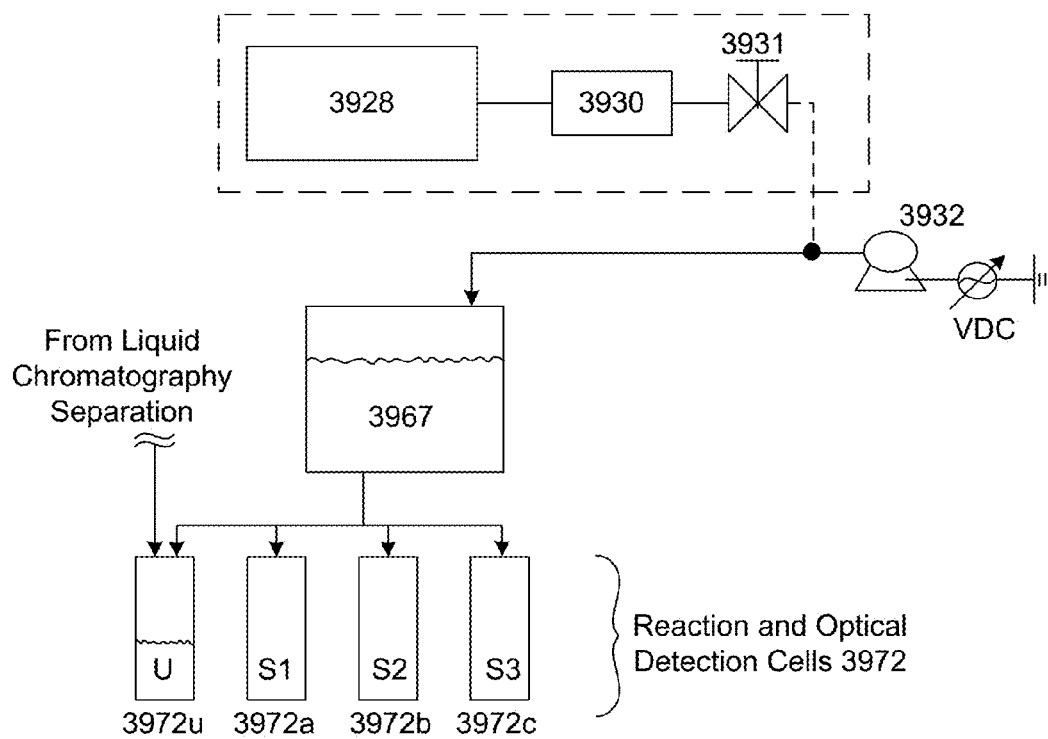
FIG. 39 is a schematic diagram of an indicator application device for liquid chromatography.

As detailed in FIG. 39 and relating to various embodiments illustrated in FIGS. 28,25, and 34, indicator(s), pre-dissolved in solvent, may be administered to breath constituents (FIG. 28) directly, or to the cannabinoid fraction eluted from the liquid chromatography separation (FIG. 34) at a controlled rate using the aforementioned micropump (similar to Figure #ZD, e.g., by adjusting the pumping speed using a variable applied voltage or pulse width modulation) or pressurized gas canister by way of a gas metering valve.

Indicator from indicator reservoir 3967 may also be applied simultaneously or sequentially to THC standards arranged in additional reaction and optical detection cells 3972 for calibration purposes, as detailed in FIG. 39 and denoted as S1-S3, for THC standards, as well as to a reaction and optical detection cell 3972u for the unknown. The indicator and/or indicator and breath constituents may be driven into reaction and optical detection cells 3972 by a micropump 3932 or a pressurized gas reservoir 3928 (which may be regulated by a regulator 3930 and metering valve 3931).

Figure 40:
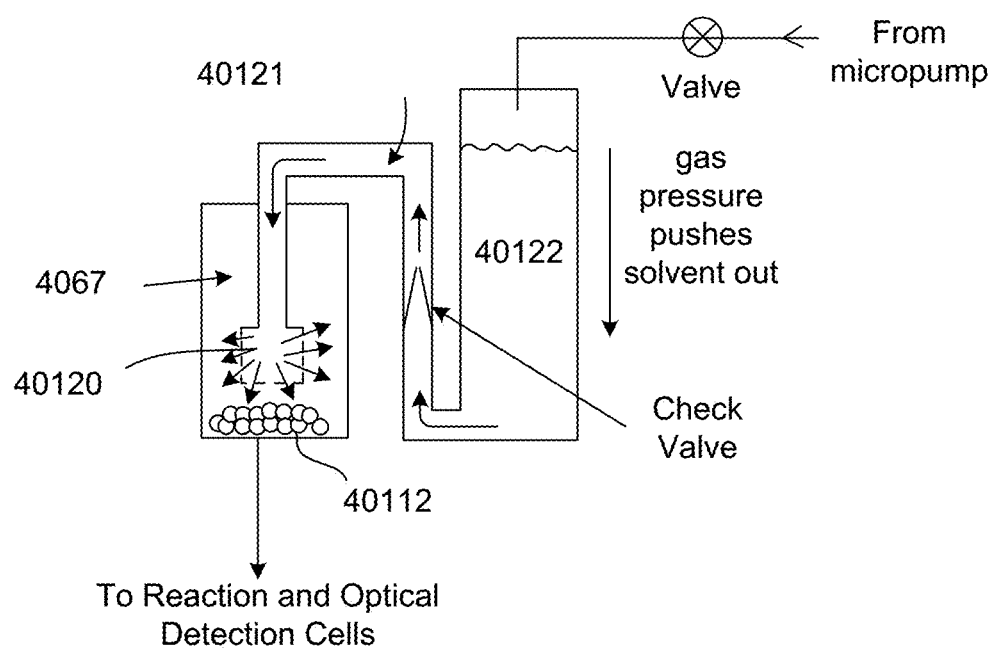
FIG. 40 is a schematic diagram of an indicator application device for an indicator in solid form.

In any of the THC and/or alcohol detection embodiments, such as that shown in FIG. 40, the THC and/or alcohol indicators may be present in solid form 40112 (e.g., powder or salt, in native, hydrated, or stabilized forms) in an indicator reservoir 4067, as presented in FIG. 40; in this case, the corresponding THC or alcohol solvent 40113 will be added to the solid indicator 40112 and mixed before application (e.g., pure solvent 40122 may be added to the solid indicator 40112 in the indicator reservoir 4067) of the indicator solution to the reaction and optical detection cells. A diffusing nozzle 40120 (e.g., porous plastic, glass, or fibers at the end of a tube, or small holes at the end of a tube) may also be present at the end of solvent application tubing 40121 to promote mixing of the solvent with the solid indicator.

After application of the indicator, the indicator may react with THC to form an adduct (chemically or electrostatically bound molecule containing THC and the indicator) which may, in different embodiments (for example see FIGS. 41, 42, 43, 44, 45) of the tagging mechanism, quench, enhance, or spectrally shift the fluorescence signal from the indicator, or 'reporter' indicator, as described below. These fluorescing mechanisms are discussed in more detail below.

Figure 41:
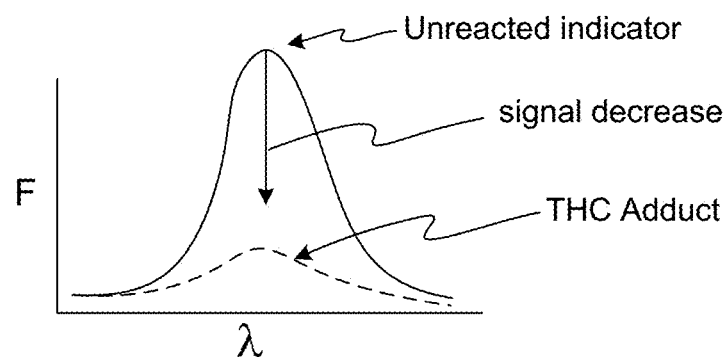
FIG. 41 is a graph of a fluorescent signal of an indicator and an adduct.

Referencing FIG. 41, in the quenching-based tagging embodiment a fluorophore which fluoresces in its free form may be reacted with THC to form a non- or partially-fluorescing adduct. THC concentration may then be assessed by measuring the decrease in fluorescence due to adduct formation as compared to one or more standards. In such embodiments, the amount of indicator present in the fluorescing sample may be tracked, e.g., via a metering device, so that the decrease in luminescence of the indicator due to adduct formation may be correlated with a THC concentration.

Figure 42:
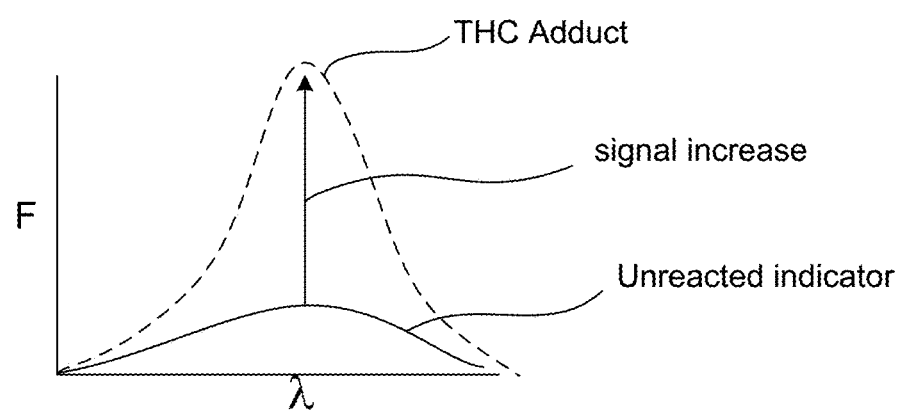
FIG. 42 is a graph of a fluorescent signal of an indicator and an adduct.

Alternatively, referencing FIG. 42, in the enhancement-based tagging embodiment a fluorophore which does not fluoresce in its free form may be reacted with THC to form a fluorescing adduct (e.g., when the indicator solution is mixed with the THC containing solution, the diazo-bond on the indicator molecule reacts with the aromatic alcohol group on THC; see discussion below for further details). THC concentration may then be assessed by measuring the increase in fluorescence due to adduct formation.

Figure 43:
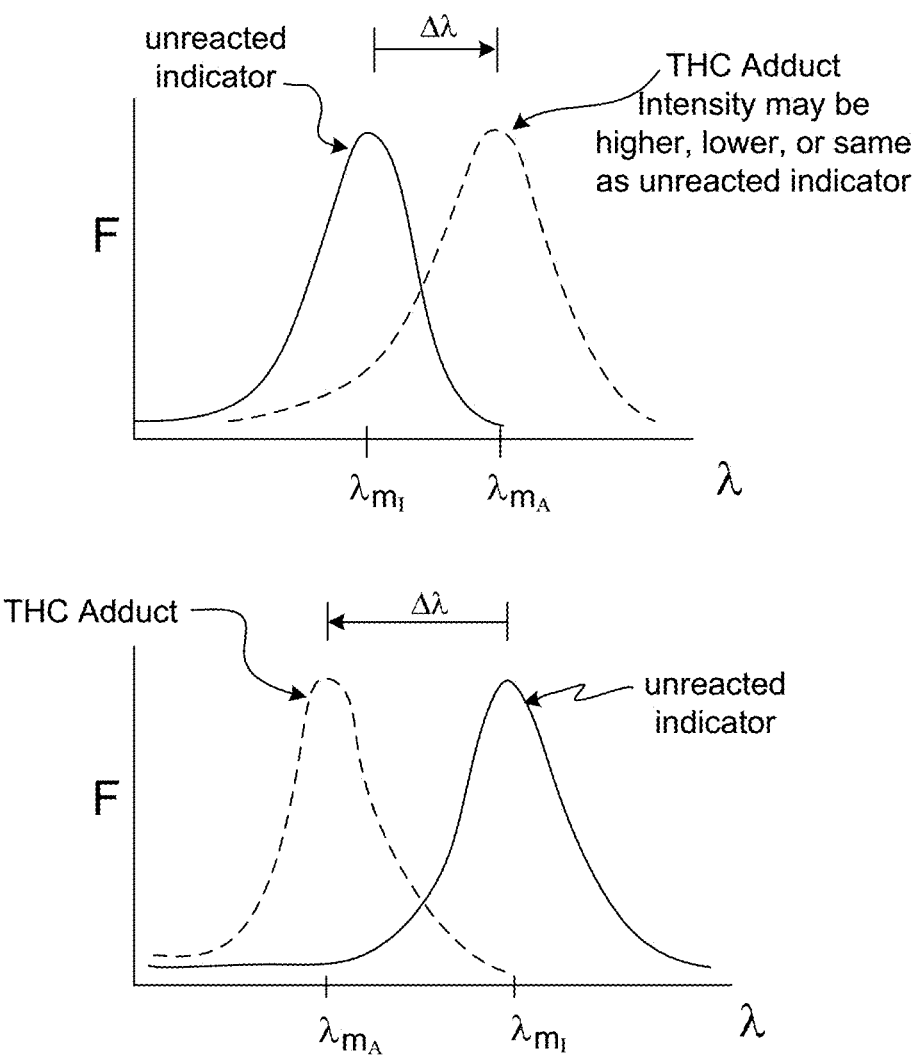
FIG. 43 is a graph of a fluorescent signal of an indicator and an adduct.
Figure 44:
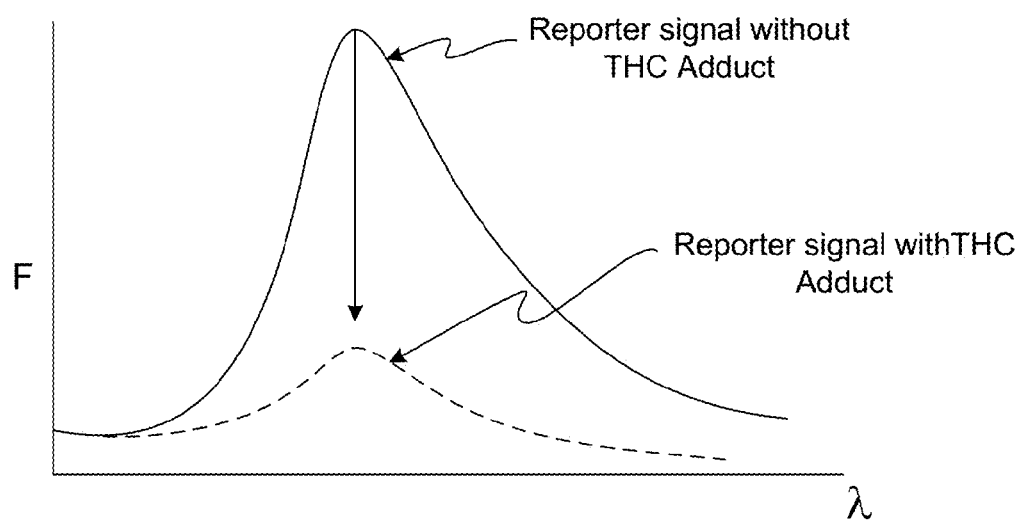
FIG. 44 is a graph of a fluorescent signal of an indicator and an adduct.

Alternatively, referencing FIG. 43, in the spectral shift-based tagging embodiment a fluorophore which fluoresces or is excited in a specific spectral range in its free form may be reacted with THC to form a fluorescing adduct which has spectrally shifted emission or excitation bands (such a shift may be to higher wavelengths, as shown in the upper diagram of FIG. 43, or to lower wavelengths, as shown in the lower diagram of FIG. 43). THC concentration is then assessed by measuring the change in excitation or fluorescence profile with respect to wavelength due to adduct formation. Change in fluorescence intensity at different wavelengths or ranges of wavelengths before and after adduct formation may also be used to assess the amount of adduct, and hence, THC. For example, picking any two different wavelengths to measure the intensity of fluorescence will give different signal levels if the reacted and unreacted spectra are shifted, as illustrated in FIG. 43. These intensities will be compared with the identical signals (e.g., at the same wavelengths) from the THC standards to establish the THC level in the unknown Alternatively, in a reporter indicator tagging embodiment, as shown in FIG. 44, one indicator may be mixed with THC to form an adduct that quenches or attenuates the fluorescence of another "reporter" indicator that does not react with THC directly. An example of this embodiment is a fast salt, such as fast blue B, reacting with THC to form an adduct that absorbs the fluorescence of the reporter indicator. In various embodiments, the fast salt may react quickly via a diazo bond to an aromatic alcohol. Pump light may be wavelength-matched to excite the reporter indicator, rather than to excite the THC-adduct-forming fast salt in its free or adduct form.

Figure 45:
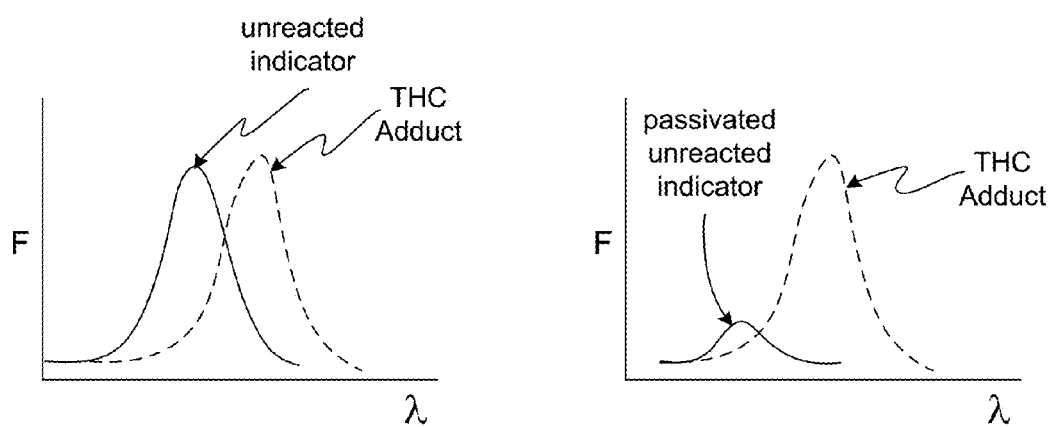
FIG. 45 is a graph of a fluorescent signal of an indicator and an adduct.

Alternatively, in any of the tagging embodiments an additional compound may be added at the THC elution location after THC adduct formation to "passivate" the unreacted indicator, as shown in FIG. 45. In this instance, "passivate" means that another compound reacts or electrostatically associates with the unreacted indicator so as to quench or spectrally shift the unreacted indicator fluorescence emission, or spectrally shift the optical absorbance band (wavelength range) of the unreacted indicator. In this way, optical signals from indicator that has not reacted with THC to form the THC adduct will be minimized or removed from the THC adduct quantification procedure, e.g., if the additional compound reacts with free indicator and kills its fluorescence, then indicator that did not react with THC will not generate any fluorescence.

Figure 46:
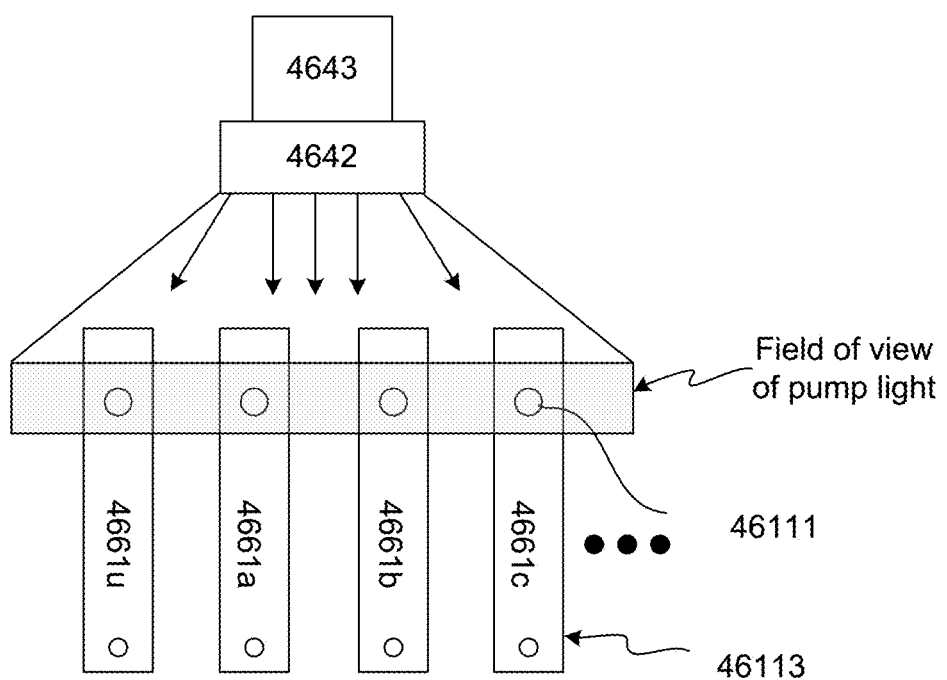
FIG. 46 is a schematic diagram of thin layer chromatography device having simultaneous illumination of multiple lanes.

In all the aforementioned tagging embodiments, excitation (optical pumping) of the adduct and unreacted indicator(s) may be accomplished with a diode/DPSS (diode-pumped solid state) laser (e.g., 532 nm green light, 1-50 mW; generally speaking, a laser with emission wavelength falling within the absorption band of the THC-fluorophore adduct, which depends on the specific fluorophore) or filtered lamp light (e.g., W filament; arc or hollow cathode Hg, Xe, Ar, or $D_2$, equipped with an optical band-pass filter with a transmission wavelength falling within the absorption band of the THC-fluorophore adduct; the light source will generally not be configured to emit light in the wavelength as the adduct fluoresces since this would make it difficult to determine if light of that wavelength originates from the light source or from the fluorescing adduct. In some embodiments, pump light may be applied to the THC elution regions of all of the TLC lanes simultaneously (e.g., from above or beneath the TLC lanes), such as is shown in FIG. 46. In FIG. 46, unknown and calibration standards are added to TLC lanes 4661 at sample delivery points 46113; after elution and indicator application, THC elution/adduct locations 46111 of TLC lanes 4661*u* (for the unknown) and 4661*a/b/c* (for THC standards) are illuminated simultaneously by pump light source 4643 via a simultaneous illumination mechanism 4642, which may, for example, be a cylindrical lens, a dispersing mirror, or a dispensing prism. Light from the pump light source 4643 may excite the THC adduct that is present in the THC elution/adduct locations 46111, causing the THC adduct to fluoresce, which may then be detected by a photodetector or other optical detector (not shown).

In another embodiment, such as is shown in FIG. 46C, the THC elution/adduct locations 46111 may be illuminated by raster scanning the light from the pump light source 4643 across the various TLC lanes 4661 individually using an electromechanical, galvano- or piezo-activated steering or rotating mirror 4644 or prism.

Figure 47:
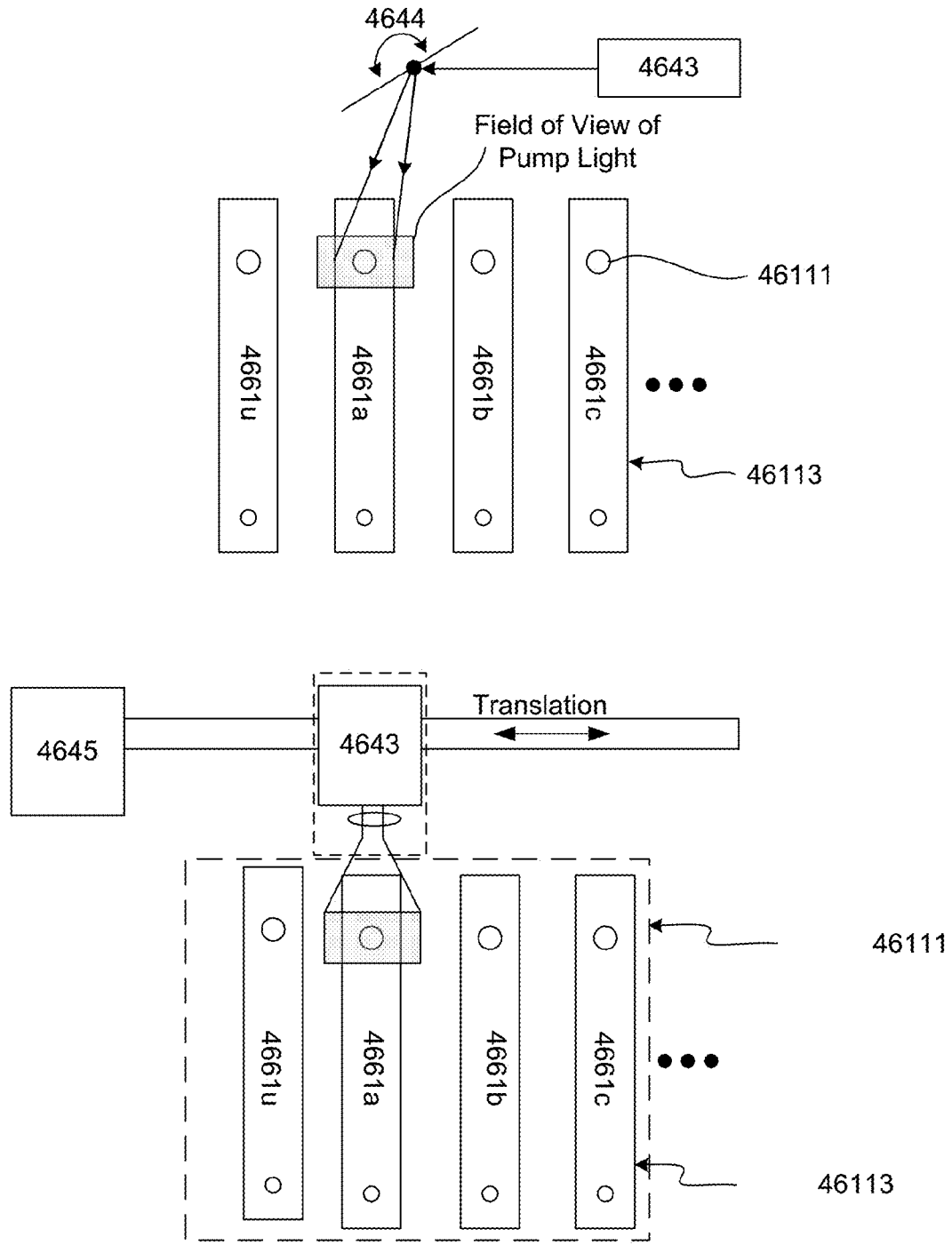
FIG. 47 is a schematic diagram of thin layer chromatography device having scanning and raster illumination of multiple lanes.

In yet another embodiment, such as is shown in FIG. 47, the pump light source 4643, i.e., excitation source, and/or fluorescence detector (not shown) may be raster scanned electromechanically from TLC lane 4661 to TLC lane 4661 by a translation mechanism 4645, or the entire TLC plate may be raster scanned electromechanically beneath a fixed excitation source and/or fluorescence detector. In embodiments requiring raster scanning of system components, movement of the light source, detector, and/or TLC substrate may be programmed into the analysis unit system controller; in this way, the optical signal from a single sample may be measured by only optically exciting one sample at a time.

Relating to various embodiments illustrated in FIGS. 28, 25, and 34, optical pumping of the unknown and THC calibration standards may be accomplished in a similar fashion to that illustrated in FIGS. 46 through 47, except that the pump light may excite the fluorophore-THC adduct in liquid solutions in each of the reaction and optical detection cells, as opposed to the TLC lanes 4661.

Figure 48:
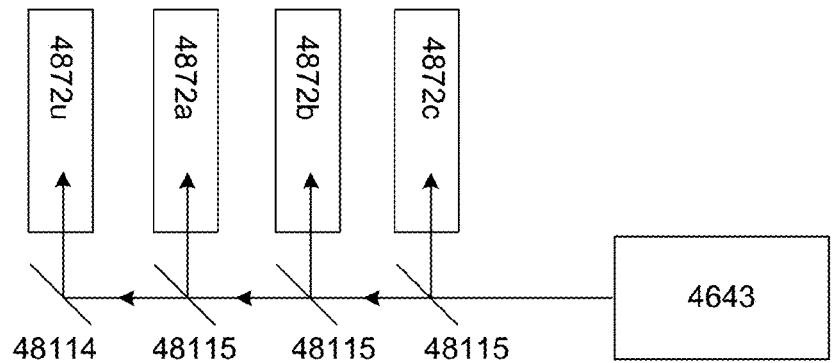
FIG. 48 is a schematic diagram of an optical pumping device having beam splitters.
Figure 49:
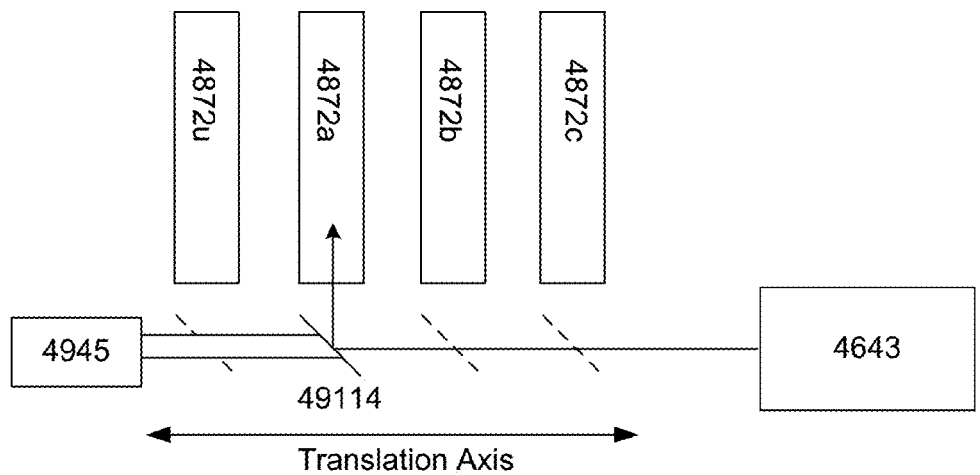
FIG. 49 is a schematic diagram of an optical pumping device having a translation mirror.
Figure 50:
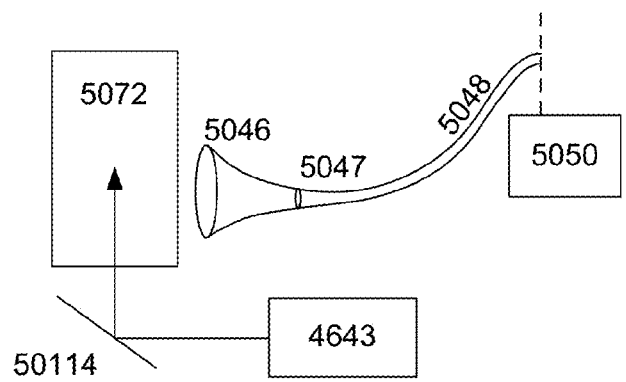
FIG. 50 is a schematic diagram of an optical pumping device having a mechanical shutter.

Optical pumping may also be arranged as shown in FIG. 48, such that light from a pump light source 4643 may be diverted by a series of beam splitters 48115 and/or a mirror 48114 into a series of reaction and detection cells 4872, or as shown in FIG. 49, such that light from a pump light source 4643 may be diverted into each of a series of reaction and detection cells 4872 by a translating mirror 49114 driven by a translation mechanism 4945. Spatially selective or gated optical detection (e.g., light from each cell or TLC lane may hit a different location on a position-sensitive photon detector, or the optical signal from each cell or TLC lane may be mechanically gated) may be used to individually assess the luminescence of the adduct in each reaction and detection cell. For example, as shown in FIG. 50, excitation energy may be supplied from a pump light source 4643 to a reaction and detection cell 5072 (in this case, a reaction and detection cell 5072 for testing the unknown) using a mirror 50114. Fluorescing light from the THC adduct in the reaction and detection cell 5072 may then be transmitted to an optical fiber 5048 by way of an aspheric lens 5046 coupled to the optical fiber 5048 by a fiber coupler 5047. The optical fiber 5048 may be interfaced with a mechanical shutter 5050 to control when light may be emitted from the end of the optical fiber 5048 onto a photodetector (not shown). Multiple such optical fibers may be used, each routing light from a different reaction and detection cell or THC lane, and individually controlled by a mechanical shutter 5050 in order to send the fluorescence light from each reaction and detection cell to the photodetector at different times.

In various embodiments of the arrangement illustrated in FIGS. 48, 49, and 50, as well as TLC lane embodiments, optical pumping of all detection cells may occur simultaneously or sequentially. Light emitted from each reaction and detection cell or TLC lane may either be (1) focused at different locations on a position-sensitive photon detector such that each sample gives a signal at a different location (for example, using a CMOS CCD array and having each signal hit a different range of pixels), or (2) focused onto a single non-position-sensitive photon detector with mechanical gating of light from each cell (e.g., light from only one cell is allowed to reach the detector at a time). In configurations of some of these embodiments, light leaving the detection cell may be collected using a single, high numerical aperture (NA) focusing lens or multiple lenses and/or transmitted to the detector using separate light pipes (e.g., structures which transmit light using total internal reflection) or optical fibers, as shown in FIG. 50.

Referencing FIG. 49, optical pumping of each detection cell may also occur sequentially using a sliding or rotating mirror, beam splitter, or lens, for example provided by a stepper motor with screw drive, denoted as a "translation mechanism", to direct the pump light source beam into each detection cell. In this way, the optical signal from each reaction and detection cell can be detected separately in time with one photon detector. In another embodiment, pump light source light may be delivered via separate optical fibers that are mechanically gated in time to allow selective excitation of one reaction and detection cell at a time. It is to be understood that the term "reaction and detection cell," as used herein, may also refer to a cell in which detection is performed but where the reaction between the unknown and the indicator occurs elsewhere, e.g., as discussed in earlier embodiments herein. In such cases, there may be little or no actual chemical reaction occurring in the reaction and detection cells, despite the name—there will, however, be the product of any reactions (the adduct) within each reaction and detection cell.

In embodiments of FIGS. 48, 49 and 50, light emitted from the liquid solutions in each reaction and detection cell may be collected using high numerical aperture focusing lenses or mirrors, and may be coupled to optical fibers or light pipes with a fiber coupler to deliver the emitted light to the photon detector, as shown in FIG. 50.

Regarding various embodiments encompassed in FIGS. 48, 49 and 50, the photon detector, detection mechanism, and associated filters, optics, etc. may include any combination of the hardware components or methods discussed below.

Fluorescence, or lack thereof, from the adduct and unreacted indicator at the THC location on the unknown and calibration TLC lanes may be measured using a photomultiplier tube (PMT), photodiode (PD), avalanche photodiode (APD), CMOS-based CCD array detector, or other device capable of measuring photonic emissions and may utilize optical filters in different embodiments to reject pump light and unwanted emissions from contaminants. In single detector embodiments (PMT, PD, APD), the fluorescence signal, or lack thereof, e.g., intensity of photons, may be measured in analog (e.g., measurement of a continuous electron current proportional to light intensity) or pulse counting (e.g., measuring a pulsed electron current with period <10 ns, with each electron pulse representing a single photon) modes. In the CCD embodiment, the photon signal may be measured in analog or pulse count mode, with different areas on the CCD array being used to detect the signal from different TLC lanes simultaneously.

Figure 51:
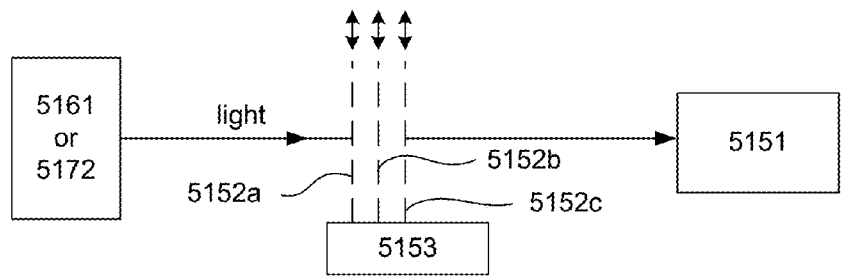
FIG. 51 is a schematic diagram of a spectral shift-based tagging device.

Referencing FIG. 51, if the spectral shift-based tagging embodiment is used, multiple optical filters 5152*a/b/c*/etc. with different pass-band wavelength ranges may be used to selectively filter out the optical signals of the unreacted indicator and the THC adduct emitted from a reaction and detection cell 5172 or a TLC lane 5161 before the emitted optical signals reach a photon detector 5151. These optical filters 5152*a/b/c*/etc. may be exchanged electromechanically by a filter exchange mechanism 5153 (e.g., rotated, linearly shifted, or flipped in/out of the optical path using a stepper motor under the control of the system microcontroller; the microcontroller would cycle through the optical filters 5152*a/b/c*/etc. and measure fluorescence in each wavelength range) to allow optical signals from the unreacted indicator or the THC adduct to be detected and quantified individually. The latter is made possible by matching the optical transmission bands (e.g., wavelength range of high transmittance) of at least two different filters to the spectral range of maximum or distinct emissions of the unreacted indicator and THC adduct; the fluorescence signal from the unreacted indicator may be measured with one filter which rejects the THC adduct emission, and vice versa. As such, optical signals from the unreacted indicator and THC adduct can be measured separately.

Figure 52:
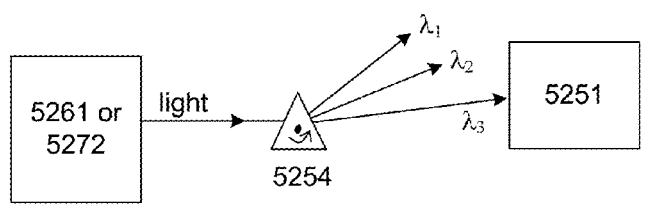
FIG. 52 is a schematic diagram of a spectral shift-based tagging device for simultaneously monitoring multiple wavelengths.

Another embodiment suitable for use with tagging and detection embodiments that require monitoring light intensity at multiple wavelengths simultaneously (spectral shift) is shown in FIG. 52. In the embodiment of FIG. 52, a photon detector 5251, e.g., a CMOS-based CCD detector, may be preceded by a wavelength dispersive element 5254, such as a prism or diffraction grating, that directs light from a reaction and detection cell 5272 or TLC lane 5261 of different wavelengths along different angular directions. In this way, multiple wavelengths may be spatially separated on the photon detector 5251, e.g., CCD array detector, to obtain an emission measurement for the fluorescence spectrum (e.g., intensity vs. wavelength) (only the measurement signal from portions of the photo detector 5251 illuminated by the wavelength(s) of interest may be considered for this measurement).

Figure 53:
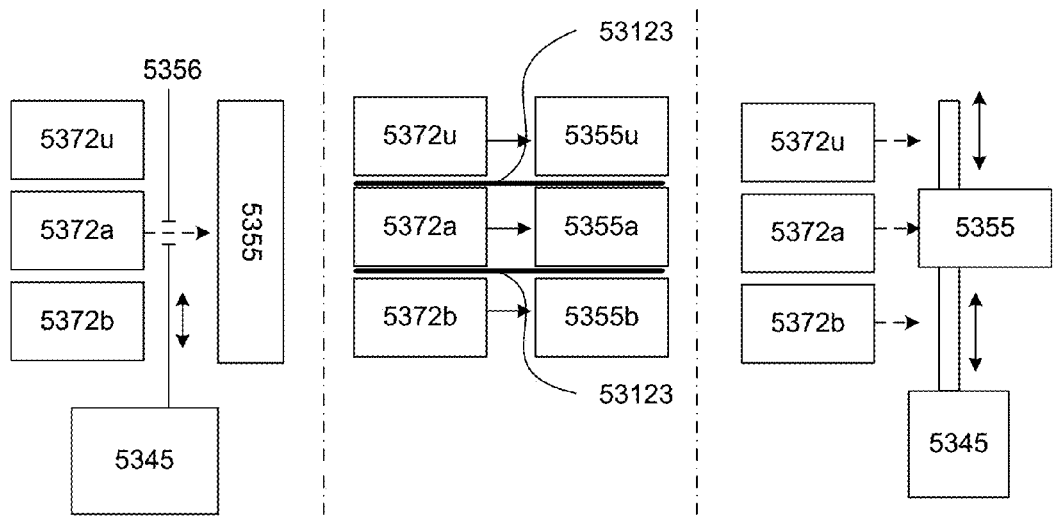
FIG. 53 is a schematic diagram of a radio-labeled tagging device.

Referencing FIG. 53, in radio-label tagging embodiments, decay products (e.g., alpha or beta emission) from the radionuclide tags in reaction and detection cells 5372 or TLC lanes (not shown) may be detected using one or more radiation detectors 5355, e.g., Geiger-type detection tubes, solid state detectors, or scintillators attached to a photomultiplier tube or tubes. Signals from each reaction and detection cell 5372 may be sequentially sampled by (1) mechanically gating the signal from each reaction and detection cell so that decay products from each reaction and detection cell are measured sequentially and individually using a single radiation detector 5355 that may be screened off from the other reaction and detection cells using a moving slit shutter 5356 driven by a translation mechanism 5345 (leftmost embodiment of FIG. 53), (2) using a separate, dedicated radiation detector for each reaction and detection cell, where each reaction and detection cell 5372/radiation detector 5355 pair is isolated from neighboring reaction and detection cell 5372/radiation detector 5355 pairs by radiation-opaque walls 53123 (middle embodiment of FIG. 53), or (3) translating the radiation detector 5355 from reaction and detection cell 5372 to reaction and detection cell 5372 using a translation mechanism 5345.

Figure 54:
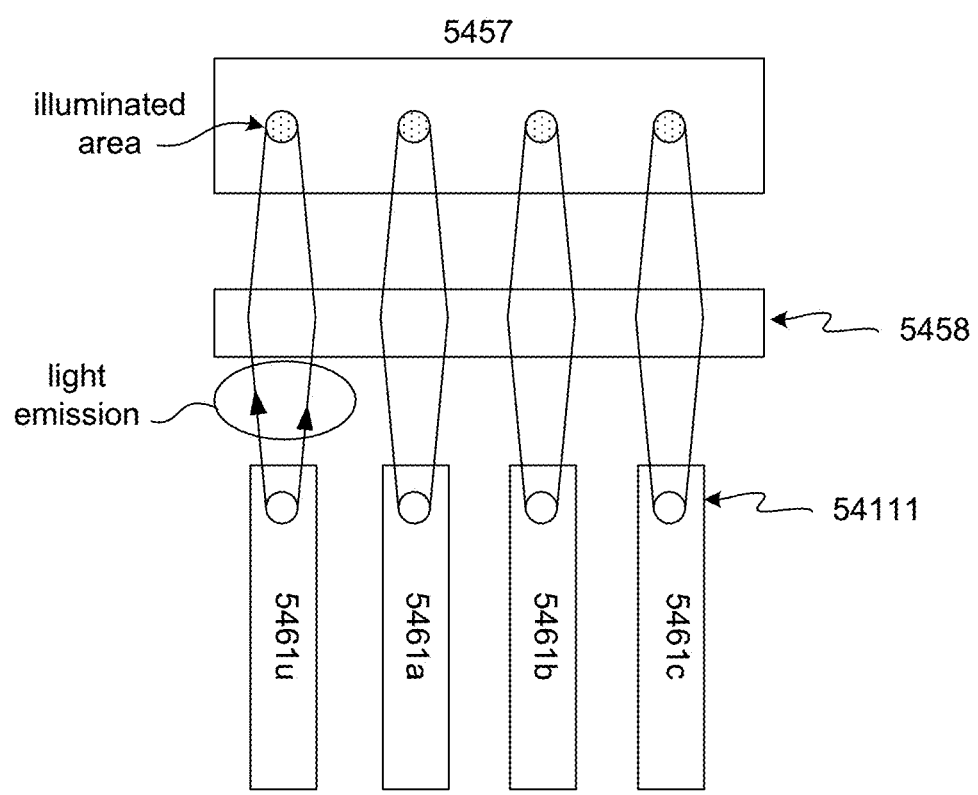
FIG. 54 is a schematic diagram of photon collection device.

Adduct and unreacted indicator emission from a single TLC lane may be assessed by (1) optically pumping all TLC lanes simultaneously (e.g., exposing all of the TLC lanes to the laser pump light) with local detection from a single TLC lane through the use of a moving collection/focusing element which directs light into the photon detector, (2) pumping individual TLC lanes using a moving excitation source or focusing optic with the light being emitted by all of the TLC lanes being collected simultaneously using a photon detector (either position-sensitive or non-position-sensitive), or (3) using a position-sensitive detectors, such as a CMOS-based CCD array detector, or a position-sensitive photomultiplier tube or diode array, to detect fluorescence from all of the TLC lanes simultaneously by stigmatically focusing (i.e., focusing the emissions from different THC lanes onto distinct, non-overlapping spatial regions) or imaging the light from different TLC lanes onto different positions on the detector; the latter embodiment may involve a focusing element (e.g., lens or curved mirror) to image the TLC lane light emissions onto the position-sensitive or array detector). This last embodiment is depicted in FIG. 54, in which TLC lanes 5461 are all illuminated simultaneously, and light emissions from fluorescence in each THC elution location 54111 is directed towards different, non-overlapping areas of a position-sensitive photon detector 5457. An optional transfer lens (focusing element) 5458 may be used to focus the fluorescing light onto the different regions of the position-sensitive photon detector 5457.

Pump light intensity may also be systematically varied to establish the linearity of photoluminescence emission signals, so as to not operate the analysis unit in a regime where the ground state fluorophore or adduct population is too low (e.g., due to optical over-pumping of ground electronic states) for quantification. If the fluorescing adduct is optically excited too fast, for example by using too much pump light, the fluorescence signal from the adduct may not be proportional to concentration of the unknown or standard because there are too many molecules in the excited state; this situation is well known in optical excitation of molecules, and is referred to as over-populating the excited state (which is the state that gives the fluorescence).

Figure 55:
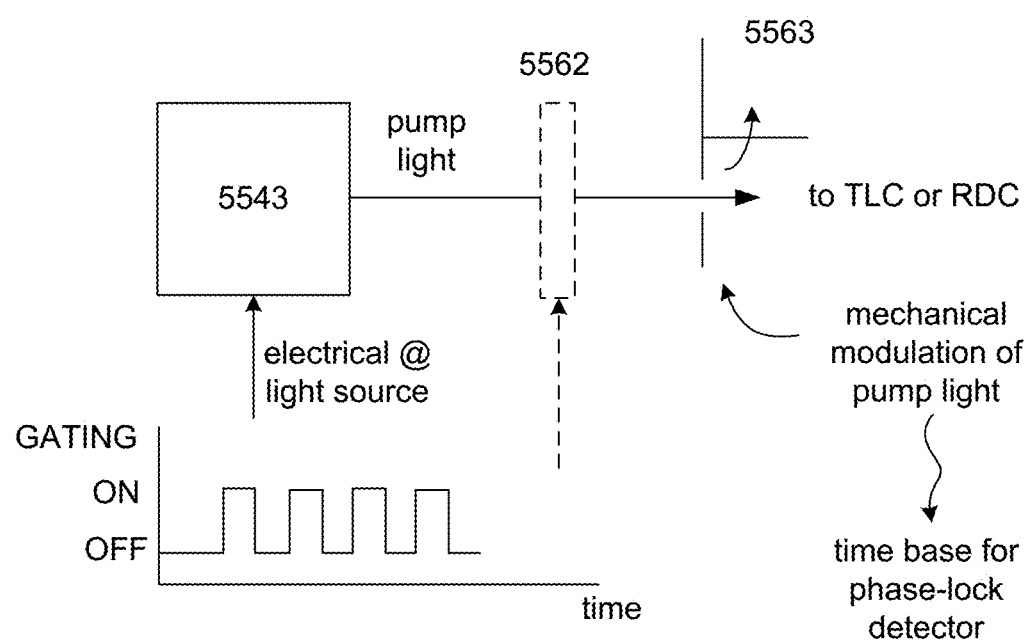
FIG. 55 is a schematic diagram of a device for phase-lock detection.

Referencing FIG. 55, the excitation light source may be mechanically (e.g., using an optical chopper MCW which may be an opaque disk with slit opening rotated by a motor, or oscillating tuning fork) or electrically modulated (e.g., by electrically modulating the excitation current to the laser diode, or using an acoustic optical modulator) to minimize photo-bleaching (over exciting the molecular ground state such that its population is small, and emission from the excited state is not proportional to concentration) of the indicator and adduct, as well as to permit phase-lock detection (modulating the optical pumping of system at frequency f and amplifying the detector response with high gain over a narrow frequency band about f) of emission signals for active background subtraction, noise filtering, and high-sensitivity photon detection. The modulation frequency (typically 100-1000 Hz) may be chosen at the factory and programmed into the system microcontroller. An example of an embodiment with a light modulation mechanism is depicted in FIG. 55. In FIG. 55, the light from a pump light source 5543 may be modulated using any of a variety of different modulation mechanisms. In some such embodiments, the power provided to the pump light source 5543 itself may be electrically modulated so as to cause the pump light source 5543 to turn off and on at a desired frequency. In some other embodiments, an electrical light modulator 5562, such as an LCD shutter or similar mechanism, may be turned on and off at a desired frequency in order to modulate the light from the pump light source 5543 that passes through the electrical light modulator 5562. In yet some other embodiments, a mechanical chopper wheel 5563 with one or more apertures in it may be placed in the optical path taken by the light from the pump light source 5543; the mechanical chopper wheel 5563 may be rotated so that the light from the pump light source 5543 is allowed through the aperture(s) or blocked by the mechanical chopper wheel 5563 at the desired frequency. After passing through whatever modulation mechanism is used, the light from the pump light source 5543 may be directed into a reaction and detection cell (RDC) or TLC lane. The timing of such modulation mechanisms may serve as the basis for a phase-lock detector.

Emission from the adduct and unreacted indicator may be measured using a photomultiplier tube operating in analog or pulse count mode, photodiode or avalanche photodiode, CMOS-based CCD array detector, or other position-sensitive detector, with phase locking to the pump source modulation. Light collection and focusing optics may be used to gather the light emitted by the THC region of the TLC lanes. The optical collection system may have a larger numerical aperture (NA=0.2-0.95) and sampling spot size than needed to collect all the light associated with the THC "spot" and indicator dosed to the TLC lane. In this way, the total integrated signal from only the adduct and only the unreacted indication can be measured and quantified for THC in each lane.

If present, the THC calibration lanes, given their pre-dosed, known THC concentrations, may be used to establish the relationship between the fluorescence signal and the THC concentration (e.g., optical signals are measured for the standards, a smooth curve is fit to signal vs. concentration using the best correlation coefficient, $r^2$, and the resulting equation then used to get the unknown concentration from the unknown's fluorescence signal), as well as to evaluate the overall system efficiency (e.g., TLC separation efficiency, adduct formation yield, fluorescence yield, optical pumping and detection system gain and sensitivity) to detect if the overall breath test, testing cartridge, and/or analysis unit is flawed or out of calibration. If the on-the-fly calibration is within specifications, the optical signal from the breath sample may be compared with the calibration relationship to quantify the THC level in the sampled breath.

In all previously discussed THC tagging and detection embodiments, THC calibration standards, in the form of pre-dosed TLC lanes or reaction and optical detection cells, may be analyzed concurrently or sequentially before or after analysis of the unknown sample from the subject under test. For example, THC standards at different levels may be dosed with indicator solution and subjected to identical detection protocols as the unknown in an effort to (1) calibrate the analysis unit on-the-fly (see below), (2) confirm correct operation of the analysis unit (e.g., if optical signals are outside factory set points), (3) validate that the testing cartridge was inserted properly (e.g., based on FIG. 8, (4) confirm that the THC test was valid and within operational specifications (e.g., if optical signals are outside factory set points), and (5) calibrate the analysis system and detection protocol for environmental conditions and variability in test cartridges (e.g., whatever affects the standards will also affect the unknown, so the calibration (below) will remove sources of variation that cannot be controlled).

Figure 56:
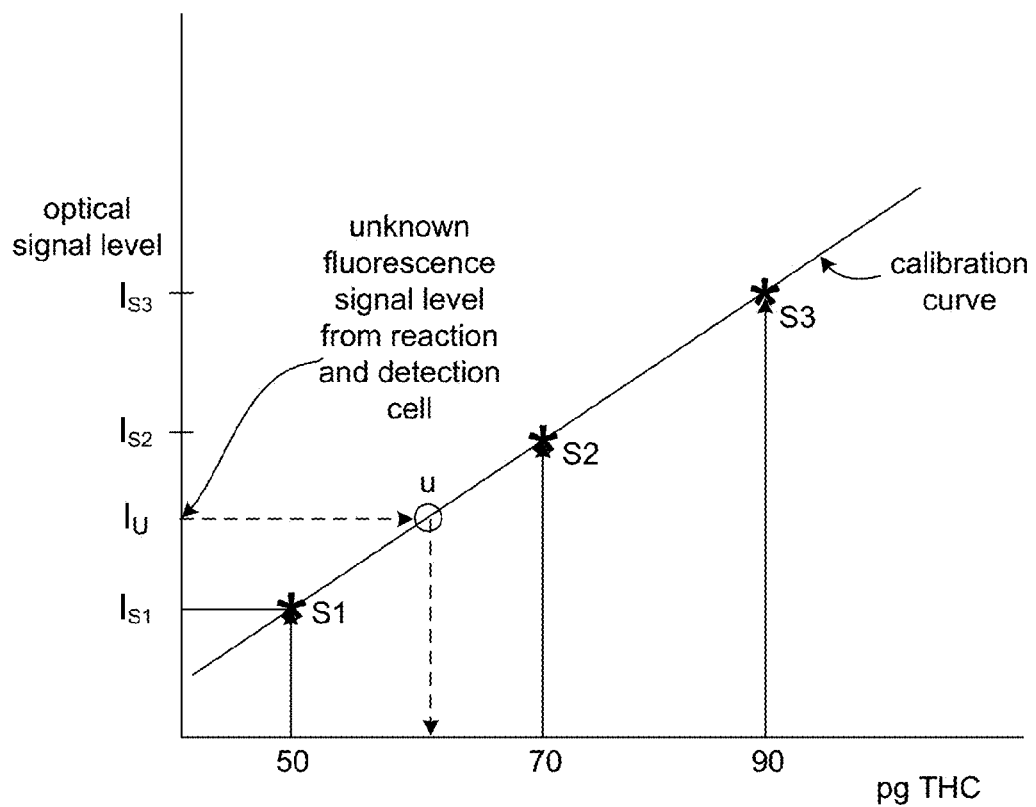
FIG. 56 is a THC calibration plot.

Referring to FIG. 56, an example calibration procedure may include the following steps:

(1) A fluorescence signal from each standard may be measured: I(S1), I(S2), etc.

(2) A microcontroller may fit a smooth curve to the data in (1); this may involve fitting a line (as in the depicted example), polynomials of degrees 2 or 3, or exponential curves to the data; the best fit curve, selected based on the highest correlation coefficient, $r^2$, may be chosen.

(3) A fluorescence signal from the unknown may be measured; this value is plugged into the best calibration equation determined in (2), and the equation is numerically solved to give the unknown concentration.

VIII. Chemical Details of Fluorescence Indicators and THC Adduct Formation

A. $N^+\!\equiv\!N$ Diazo Functionalized Indicators

Various embodiments employ indicators containing stabilized $N^+\!\equiv\!N$ diazo functional groups that have been synthesized to rapidly (e.g., <2 min) and selectively bind to THC and/or derivatives thereof at para and/or ortho positions of the phenol ring forming an N=N azo bond, hereafter referred to as the diazo-aromatic alcohol reaction. The act of binding (1) produces a chemically bonded THC-indicator adduct and (2) activates, deactivates, alters, or sustains the fluorescence properties of the initial indicator prior to binding. The indicator is generally of the form:

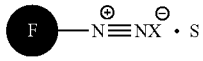

where:
F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium seleninde sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;

$N^+\!\equiv\!N$ is a diazo-functional group that is chemically bonded/grafted/functionalized/conjugated to F;

$X^-$ is a negatively charged ion that charge balances the positively charged diazo functional group $N^+\!\equiv\!N$, examples of which may include fluoride, sulfide, chloride, nitride, bromide, iodide, arsenate, phosphate, arsenite, hydrogen phosphate, dihydrogen phosphate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof;

S is a $N^+\!\equiv\!N$ stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid, thiocyanate, thione, thial, sulfonyl chloride, carbonyl chloride, phosphine, phosphonic acid, phosphate, phosphodiester, boronic acid, boronic ester, boronic acid, borinic ester, or any combination thereof.

Indicators including stabilized $N^+\!\equiv\!N$ diazo functional groups can be synthesized, for example, by a process including the combination of a primary amine ($-NH_2$) functionalized fluorophore, F (listed above), in an acidic solution ($H^+X^-$) with sodium nitrite ($NaNO_2$) and stabilizers, S (listed above), at 0-10° C., with or without stirring:

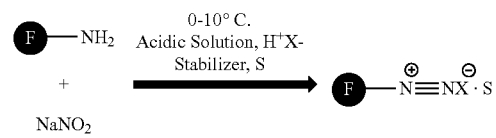

Acidic solutions may include any negatively charged ion $X^-$ (such as those listed above) charge balanced with a positively charged hydrogen ion $H^+$, in a solvent that has been chosen for suitable or optimal reaction conditions, examples of which include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

In various embodiments of the indicator, a heretofore unknown indicator Rhodamine-$N^+\equiv N$ $Cl^-.ZnCl_2$ may be synthesized as follows (the amounts and times provided are for exemplary purposes only; other amounts and time as would be apparent to one skilled in the art are considered within the scope of this disclosure):

Rhodamine 123 (1 mg) is dissolved in acetonitrile (1 mL) and dichloromethane (4 mL) containing trifluoroacetic acid (0.1 mL), and then cooled to 0-10° C. while stirring for 20 min. Sodium nitrite (20 mg) is then added to the solution at 0-10° C. with continued stirring for 10 min. Sulfamic acid (20 mg solid acid) is then added to the solution at 0-10° C. with continued stirring for 10 min. Zinc chloride (200 mg) is then added to the solution at 0-10° C. with continued stirring for 10 min. The resulting mixture is diluted with $H_2O$ (20 mL) and extracted using dichloromethane (10 mL) to produce a Rhodamine-$N^+\equiv N$ $Cl^-.ZnCl_2$ indicator. The indicator can be used as is, or can be filtered out as a powder (using #5 filter paper) that can be redissolved in another solvent (e.g., water with $ZnCl_2$; 200 mg $ZnCl_2$ in 20 mL water) optimized for $N^+\equiv N$ stabilization.

Prior to formation of the THC-indicator adduct, the indicator is dissolved in a solvent, for example one that has been optimized for $N^+\equiv N$ stabilization, examples of which may include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

In various embodiments of the indicator, the $N^+\equiv N$ diazo functional group may serve as a reactive chemical linker that will rapidly (e.g., <2 min) and selectively bind to THC and/or derivatives thereof at para and/or ortho positions of the phenol ring forming an $N=N$ azo bond:

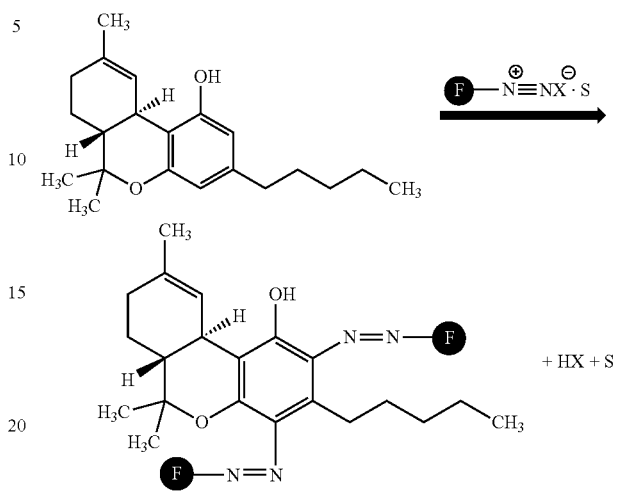

The act of binding (1) produces a chemically bonded THC-indicator adduct and (2) activates, deactivates, shifts, or sustains the fluorescence properties of the initial indicator prior to binding. Activating fluorescence properties indicates an increase in fluorescence emission intensity. Deactivating fluorescence properties indicates a decrease in fluorescence emission intensity. Shifting fluorescence properties indicates a spectral shift and/or broadening of fluorescence emission wavelengths. Sustaining fluorescence properties indicates no change in fluorescence emission intensity or wavelengths.

B. $SO_2Cl$ Sulfonyl Chloride Functionalized Indicators

In an alternate embodiment, novel indicators containing stabilized $SO_2Cl$ sulfonyl chloride functional groups may be synthesized to rapidly (e.g., <2 min) and selectively bind to THC and/or derivatives thereof at the hydroxyl group of the phenol ring forming a $SO_2O$ sulfonate ester bond. The act of binding (1) produces a chemically bonded THC-indicator adduct and (2) activates, deactivates, shifts, or sustains the fluorescence properties of the initial indicator prior to binding. The indicator is generally of the form:

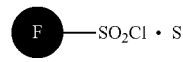

where:
F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;

$SO_2Cl$ is a sulfonyl chloride functional group that is chemically bonded/grafted/functionalized/conjugated to F;

S is a SO₂Cl stabilizer, examples of which may include phenylhydroquinone, p-tert-butylcatechol, nitrobenzene, anthraquinone, dinitrocresol, dinitromesitylene, Rose Bengal, sodium sulfite, or any combination thereof.

Novel indicators containing stabilized SO₂Cl sulfonyl chloride functional groups can be synthesized, for example, by a process including the combination of an aryl (—H$_{Ar}$), diazo (—N⁺≡N), or alkyl (—H$_{Alk}$) functionalized fluorophore, F (listed above) in acidic (H⁺X⁻) solution with either chlorosulfuric acid (HOSO₂Cl), sulfur dioxide (SO₂), chlorine (Cl₂), thionyl chloride (SOCl₂), phosphorous trichloride (PCl₃), phosphorous pentachloride (PCl₅), or oxalyl chloride (ClCOCOCl), or any combination thereof, and stabilizers, S (listed above), with or without stirring:

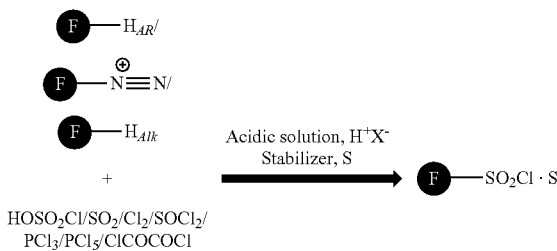

Acidic solutions include any negatively charged ion X⁻ (such as those listed above) charge balanced with a positively charged hydrogen ion H⁺, in a solvent that has been chosen for suitable or optimal reaction conditions, examples of which may include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

Prior to formation of the THC-indicator adduct, the indicator is dissolved in a solvent that has been optimized for SO₂Cl stabilization, examples of which may include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

In various embodiments of the indicator, the SO₂Cl sulfonyl chloride functional group may serve as a reactive chemical linker that will rapidly (e.g., <2 min) and selectively bind to THC and/or derivatives thereof at the hydroxyl group of the phenol ring forming a SO₂O sulfonate ester bond:

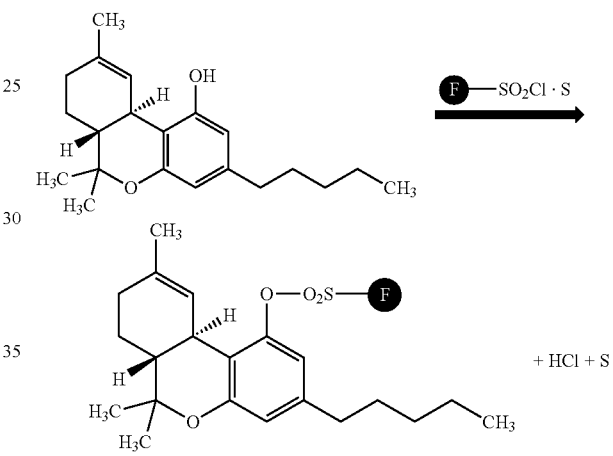

The act of binding (1) produces a chemically bonded THC-indicator adduct and (2) activates, deactivates, shifts, or sustains the fluorescence properties of the initial indicator prior to binding. Activating fluorescence properties indicates an increase in fluorescence emission intensity. Deactivating fluorescence properties indicates a decrease in fluorescence emission intensity. Shifting fluorescence properties indicates a spectral shift and/or broadening of fluorescence emission wavelengths. Sustaining fluorescence properties indicates no change in fluorescence emission intensity or wavelengths.

C. COCl Carbonyl Chloride Functionalized Indicators

In an alternate embodiment, novel indicators containing stabilized COCl carbonyl chloride functional groups may be synthesized to rapidly (e.g., <2 min) and selectively bind to THC and/or derivatives thereof at the hydroxyl group of the phenol ring forming a COO ester bond. The act of binding (1) produces a chemically bonded THC-indicator adduct and (2) activates, deactivates, shifts, or sustains the fluorescence properties of the initial indicator prior to binding. The indicator is generally of the form:

where:
F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;

COCl is a carbonyl chloride functional group that is chemically bonded/grafted/functionalized to F;

S is a COCl stabilizer, examples of which may include phenylhydroquinone, p-tert-butylcatechol, nitrobenzene, anthraquinone, dinitrocresol, dinitromesitylene, Rose Bengal, sodium sulfite, thiourea, or any combination thereof.

Novel indicators containing stabilized COCl carbonyl chloride functional groups can be synthesized, for example, by a process including the combination of a carboxylic acid (—COOH) functionalized fluorophore, F (such as those listed above) in dimethylformamide (DMF) solution with either thionyl chloride ($SOCl_2$), phosphorous trichloride ($PCl_3$), phosphorous pentachloride ($PCl_5$), or oxalyl chloride (ClCOCOCl), or any combination thereof, and stabilizers, S (listed above), with or without stirring:

DMF solutions may include combinations of dimethylformamide and another solvent that has been chosen for suitable or optimal reaction conditions, examples of which may include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethyl-phosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

Prior to formation of the THC-indicator adduct, the indicator is dissolved with varied amounts of quinuclidine in a solvent that has been optimized for COCl stabilization, examples of which may include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxylethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

In various embodiments of the indicator, the COCl carbonyl chloride functional group serves as a reactive chemical linker that will rapidly (<2 min) and selectively bind to THC and/or derivatives thereof at the hydroxyl group of the phenol ring forming a COO ester bond:

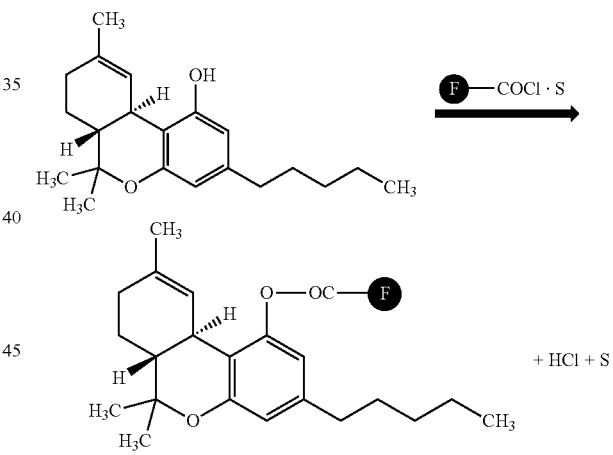

The act of binding (1) produces a chemically bonded THC-indicator adduct and (2) activates, deactivates, shifts, or sustains the fluorescence properties of the initial indicator prior to binding. Activating fluorescence properties indicates an increase in fluorescence emission intensity. Deactivating fluorescence properties indicates a decrease in fluorescence emission intensity. Shifting fluorescence properties indicates a spectral shift and/or broadening of fluorescence emission wavelengths. Sustaining fluorescence properties indicates no change in fluorescence emission intensity or wavelengths.

D. Radionuclide-Labeled Indicators

In another tagging embodiment, any of the aforementioned chemical routes to tag the THC molecule, e.g., involving $N^+{\equiv}EN$ diazo, $SO_2Cl$ sulfonyl chloride, or COCl carbonyl chloride functionalized indicators and their associated chemistry, may include a radionuclide label (e.g., an alpha or beta emitter) such as $^{32}$P, $^{33}$P, $^{89}$Sr, $^{14}$C, or $^{35}$S. The radionuclide indicator solution may be added to the unknown and THC standards, as discussed previously. The intensity of radioactive decay products may be detected as described previously and illustrated in FIG. 53.

Decay products from the radionuclide tag may be collected and used, along with calibration signal levels from the THC standards, to quantify the THC level in the unknown. This calibration procedure and unknown determination may be carried out as previously described, except that the radionuclide decay signal from the radionuclide detector may be used instead of fluorescence.

E. Metal Oxide Semiconductor

In other embodiments, a metal oxide semiconductor (MOS) based gas detection system, optimized for the detection of THC in breath samples, may be used. MOS sensors function by measuring a change electrical properties of the sensing material when an analyte of interest is absorbed onto the surface of the MOS. Numerous metal-oxide surfaces exists. They can be separated into two groups: those that are made up of transition metal-oxides, where the metal components of the surface have valence electronic configurations consisting of d0 to d10 configurations, and non-transition metal oxides, which consist of pre-transition metals and post-transition metals that do not have valence d-orbitals in their electronic configurations. Some suitable transition metal-oxide surfaces include NiO, CuO, Fe2O3, Mn2O3, TiO2, Co3O4, Cr2O3, WO3, V2O3, Nb2O5, MoO3 and Ta2O5. Some suitable pre-transition metal-oxide surfaces include Al2O3, MgO, La2O3, CeO2, Nd2O3 and SrO while some post-transition metal-oxide surfaces include SnO2, ZnO, In2O3 and GeO2.

As previously mentioned, sensors based on MOSs function to detect targeted gas-phase analytes via redox reactions that occur between the analyte and the metal-oxide surface. The reactions lead to variations in the electronic properties of the surface material. This variation can be observed by measuring a change in the capacitance, resistivity, work function or optical characteristics of the sensing material. Accordingly, several factors can affect the redox reactions that occur on the surface of the MOS, which in turn determines the sensitivity and selectivity of the MOS to the analyte of interest. These factors include the characteristics and the structure of the sensing layer, the percent composition of the various metal-oxides used to make up the surface (if multiple metal-oxides are combined to form a composite surface) and the temperature of the MOS surface. Thus, the working temperature will be variable parameter for each MOS surface for suitable or optimal sensitivity and selectivity towards the detection of THC in breath. The suitable temperature range may vary from room temperature (e.g., about 25° C.) to about 500° C.

In some embodiments, a MOS sensor can be modified to improve its responsiveness to a targeted gas-phase analyte by incorporating a specific quantity of a dopant material to metal-oxide surface. A dopant is a trace-level elemental impurity that is inserted into a substrate for the purpose of altering or tuning the electrical properties of the sensing material. Therefore, adding a known concentration of a dopant to the metal-oxide surface will be explored as part of this effort to potentially improve the sensitivity and selectivity of MOS to THC in breath. Dopants that will be deposited on the various MOS surfaces will include, but will not be limited to, Au, Ag, Cu, Pt and Pd. These metals have been shown to be highly reactive in the presence of delocalized electron density, such as is found in conjugated Pi bonding systems. Pi bonds of this type are found in some of the functional groups of the THC molecule. Other suitable dopant species include, but are not be limited to, V, W, Fe, Ir, Ta, Ni, Mo, Co, Al, Ga and Ti. Suitable concentrations of the dopants range anywhere between one part-per-billion (ppb) up to 0.1% of the metal-oxide substrate. Given the description herein, these concentrations can be tuned to optimize the performance of the sensor for the detection of THC and the determination of it concentration level in breath analysis.

There are two distinct ways that the dopant can be incorporated into the sensing material. 1) The dopant can be deposited onto the substrate and form metallic nanoparticles. Here, the dopant decorates the surface and forms small islands that are distributed about the surface layer. The high chemical activity of the small particles facilitates the responsiveness of the sensor. 2) The dopant can insert into the lattice of the MOS, essentially substituting itself in place of the metal constituent of the metal-oxide material. In this scenario, the dopant modifies the electronic properties of the substrate by generating active sites for the absorption of gas-phase analytes. The formation of regions on the sensing material that are either rich with electron density (regions of localized negative charge) or with electron holes (regions of localized positive charge) enhance the response of the MOS sensor.

F. Alternative and/or Complementary Sensor Technology

Polymer-based gas sensors can also be used. Similar to MOS sensors, when polymer layers are exposed to gas-phase analytes, the physical properties of the surface layer of the polymer are altered by absorption of the analyte. Unlike MOS sensors, the interactions that occur in polymers usually involve London dispersion forces such as induced dipole/induced dipole interactions, dipole/dipole interactions, dipole/induced dipole interactions, and hydrogen-bond interactions.

Two types of polymer gas sensors exist, conducting polymers (CP) and non-conducting polymers (NCP). Some suitable CPs for targeted analyte (TA) sensors include, but are not limited to, polyaniline, polythiophene, poly(acetylene), poly(p-phenylene vinylene), poly(pyrrole), poly(3,4-ethylenedioxythiophene) and poly(p-phenylene sulfide). Typically, NCPs are coated onto other sensing devices and used to enhance absorption of a targeted analyte. NCPs can also be used to cause changes in resonance frequency, enthalpy of absorption/desorption and dielectric constants, depending upon what type of sensor is used. NCPs have been coatings for surface acoustic wave (SAW) sensors, surface transverse wave (STW) sensors, microcantilevers, calorimetric and capacitive sensor devices. These types of devices may also be adapted for the detection of THC in breath samples. A NCP can also be coated onto the surface of a MOS sensor to potentially enhance sensitivity and selectivity for the detection of TA in breath samples.

Carbon nanotubes (CNTs) can also be used for detecting THC in breath samples. CNTs function similarly to MOS sensor by measuring a change in electrical properties when an analyte of interest is absorbed onto the surface of the CNT. CNTs are highly sensitive to very low concentrations of gases at room temperature due to their large surface area to volume ratio. Two types of CNTs exist, single-walled (SW) and multi-walled (MW). CNTs can also be incorporated into other materials, such as MOS, to improve sensitivity, if needed.

A gas chromatography (GC) column is a device that separates a mixture of gas-phase analytes into its individual molecular components. A GC column consists of a mobile phase, which is usually an inert gas, and a stationary phase that is either a layer of liquid or a polymer that is supported on the inside of the glass or metal tubing. The gas-phase analytes interact with the walls of the column and each analyte has a unique level of interaction with the stationary phase of the column. The level of interaction determines how much time is required for an analyte to exit, or elute, from the column. This is known as the "retention time" of the column. Experimental parameters such as the flow rate of the mobile phase or the temperature/temperature ramp applied to the column can be tuned in order to alter the retention time of the column for a targeted analyte. The relative abundance of each compound can also be determined with the GC column.

In recent years, advances have been made that have significantly reduced the size of GC columns, making them more suitable for use in portable, handheld sensor devices. Here, a miniaturized GC column can be incorporated into the design of a sensing device for the detection of THC in breath samples. The GC column can be used as a complementary analytical technique for THC detection. The GC column can be combined with a previously mentioned gas sensor such as MOSs, CPs, SW-CNTs or MW-CNTs that can function as the detection method. A combination of both the time required for the analyte to elute from the GC column with the characteristic response of the gas sensing element can provide compelling evidence for the detection and quantification of the concentration level of THC in breath samples.

Similarly to GC columns, a number of other gas sensing techniques can be combined to generate a device for the detection of THC in breath samples. These combined sensors can provide complementary data from two or more of any of the previously mentioned gas sensing technologies that would generate a "fingerprint" for the targeted analyte. This approach can increase selectivity by exploiting different properties of the combined sensing elements to yield a multi-dimensional signature. This can result in a "sensor array" for the detection of THC in breath samples.

If the limit of detection (LOD) required the detection of THC in breath samples (approximately 1 ppb) is not readily achieved by the uses of the aforementioned gas sensing methods or combinations of methods, a preconcentration device can be incorporated to the front end of a THC sensing system based on any of the technologies listed above to improve sensitivity of the device to low concentrations of the target analytes if needed. For example, a suitable preconcentrator functions by first absorbing the targeted analyte while other gas-phase species (such as those present in normal air) are allowed to pass over the concentrating material unaffected. The preconcentrator is then heated to a predetermined temperature to release the absorbed analyte into the sensor/sensor array. Lastly, the preconcentrator is cooled back to the ambient temperature in preparation for the next cycle. Methods to determine the optimal preconcentrating time, leading to efficient absorption of THC in breath samples are contemplated. These methods can also be used to calibrate the preconcentration time with the response of the detection method/methods, so that quantification of the concentration levels of THC in the breath samples can still be obtained. For this purpose, a preconcentrating material having a known "preconcentration factor" can be used. A preconcentration factor is the ratio between the concentration of input and output of the gas that is to be absorbed by the device. A higher value results in greater absorption of the targeted gas-phase analyte. Solid-phase microextraction and sorbent traps can be used as preconcentrators and have been employed previously for breath analysis to search for biomarker as evidence for various diseases. For sorbent traps, the use of several preconcentrating materials can be used to determine the effectiveness for the absorption of THC in breath samples. These materials include, but are not limited to, organic polymers, carbon-based molecular sieves and graphitized carbon.

IX. Data Analysis, Human Interface, and Ancillary Technological Art

Figure 57:
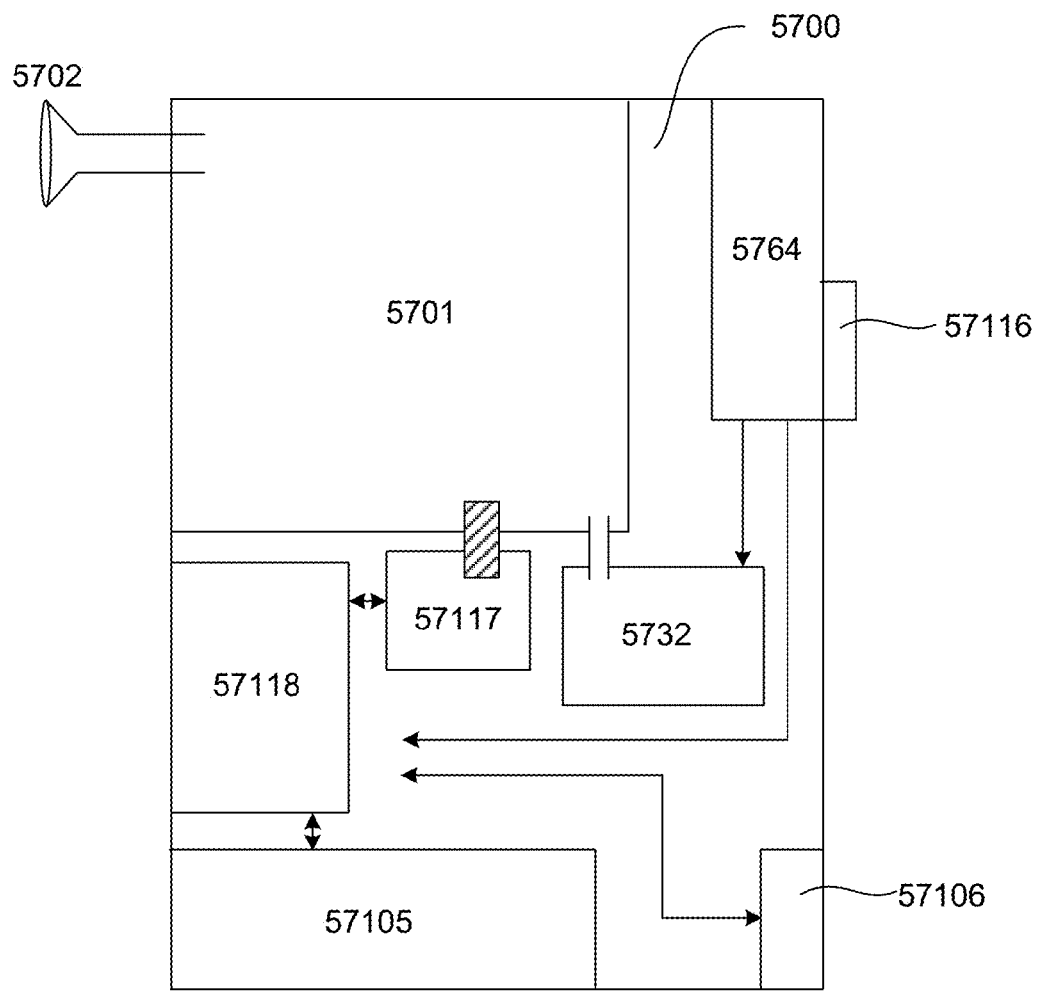
FIG. 57 is a schematic diagram of a breath analysis device.

Various embodiments may include one or more of the components illustrated in FIG. 57, as described in this section.

The analysis unit 5700 may include a human interface and readout #YZ105 with indicator readouts and/or alarms (e.g., light, LED, optical display, audible, or any combination thereof) that may provide information on analysis unit readiness, a test in progress, adequate breath volume sampled, quantification progress, test completion, THC level detected (e.g., over/under a factory set level and pg of THC detected), alcohol level (in embodiments configured to test for both drugs and alcohol), a failed test, the unit being out of calibration, a need to replace a sampling and quantification cartridge, the battery charge level (% remaining), a low battery, or any other functionality, or any combinations of the information listed above. The human interface and readout 57105 may also have buttons or other controls to initiate and stop a test.

Optical data from each test, including the unknown and calibration standards, as well as individual test results, date, time, and location (for embodiments equipped with GPS capability) may be cumulatively stored in the analysis unit's non-volatile RAM, or other storage device or medium operably connected with a microcontroller 57118. The data may be downloadable and/or extractable from the analysis unit through a communications interface 57106 using a USB, WiFi, or Ethernet interface, or any other data transfer device or technique. In some embodiments, the data may be retained permanently in the unit's non-volatile RAM, which may only be erasable or resettable at the factory, although in other embodiments, such a limitation may not be present.

In various embodiments, system status and data related to system readiness, system ID, testing and maintenance history, testing cartridge ID (barcode), and test results may be communicated intermittently or in real time by cable, WiFi, Bluetooth, or any other wireless or wired communication module to communicate data, unidirectionally from the analysis unit, or bidirectionally, with one or more other devices, computers, data networks, servers, network clouds, or computers and/or data networks located at one or more police departments, and the like, for archival and evidentiary purposes. Examples of a communication module integrated in the testing cartridge housing and/or analysis unit include a Wi-Fi module, a Bluetooth module, an radio frequency (RF) communication module, a transceiver, a transmitter, a Zigbee module, a USB module, or an RS-232 module. In certain embodiments, each cartridge includes a unique identifier such as a bar code, an identification number or serial number and the like which is recognized and authenticated by the analysis unit upon mechanical engagement with the analysis unit housing. Thereafter, the unique identifier information may be stored, transmitted or otherwise associated with the resulting THC and alcohol level determined from the obtained breath sample.

The hand-held analysis unit 5700 may be battery powered using a battery 5764 and rechargeable via a battery recharge interface 57116 using, for example, 12 VDC from a vehicle or 120 VAC from a wall-powered docking station.

In various embodiments, allowances in the design may be made for field-replaceable modules or cartridges including any or a combination of the following: the overall test cartridge 5701, mouthpiece 5702, catch solvent, flush solvent, indicator solutions, pressurized gas cartridges, and/or waste capture reservoirs. In different embodiments, the replaceable test cartridge 5701 may include any combination of these components. In some embodiments, some other components may be part of the analysis unit 5700 as opposed to the testing cartridge 5701. For example, the analysis unit 5700 may include a micropump 5732, as well as optical elements 57117, which may include one or both of the pump light source(s) and the photon detector(s).

X. Example of the THC/Alcohol Testing Device

Figure 58:
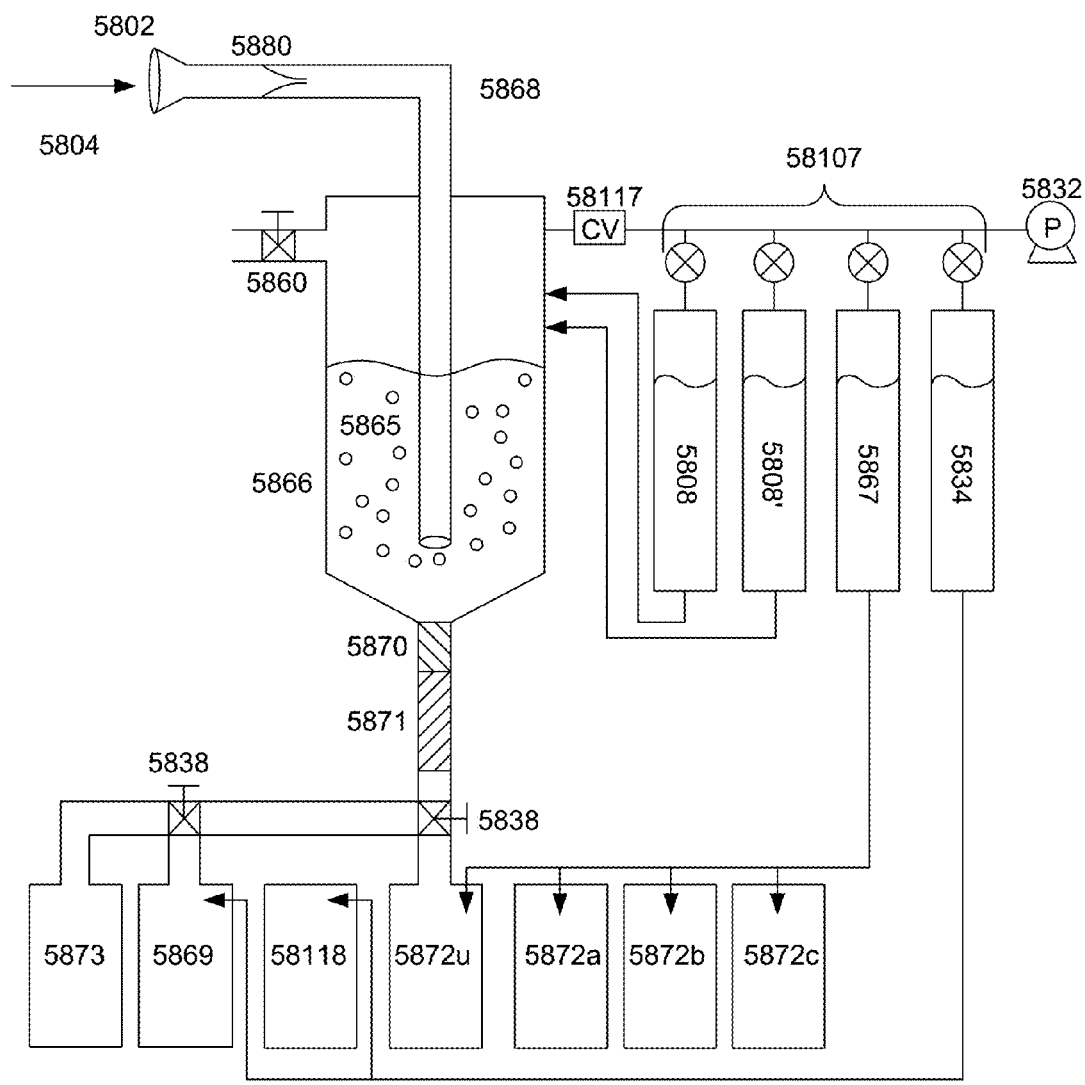
FIG. 58 is a schematic diagram of a breath analysis device.
Figure 59A:
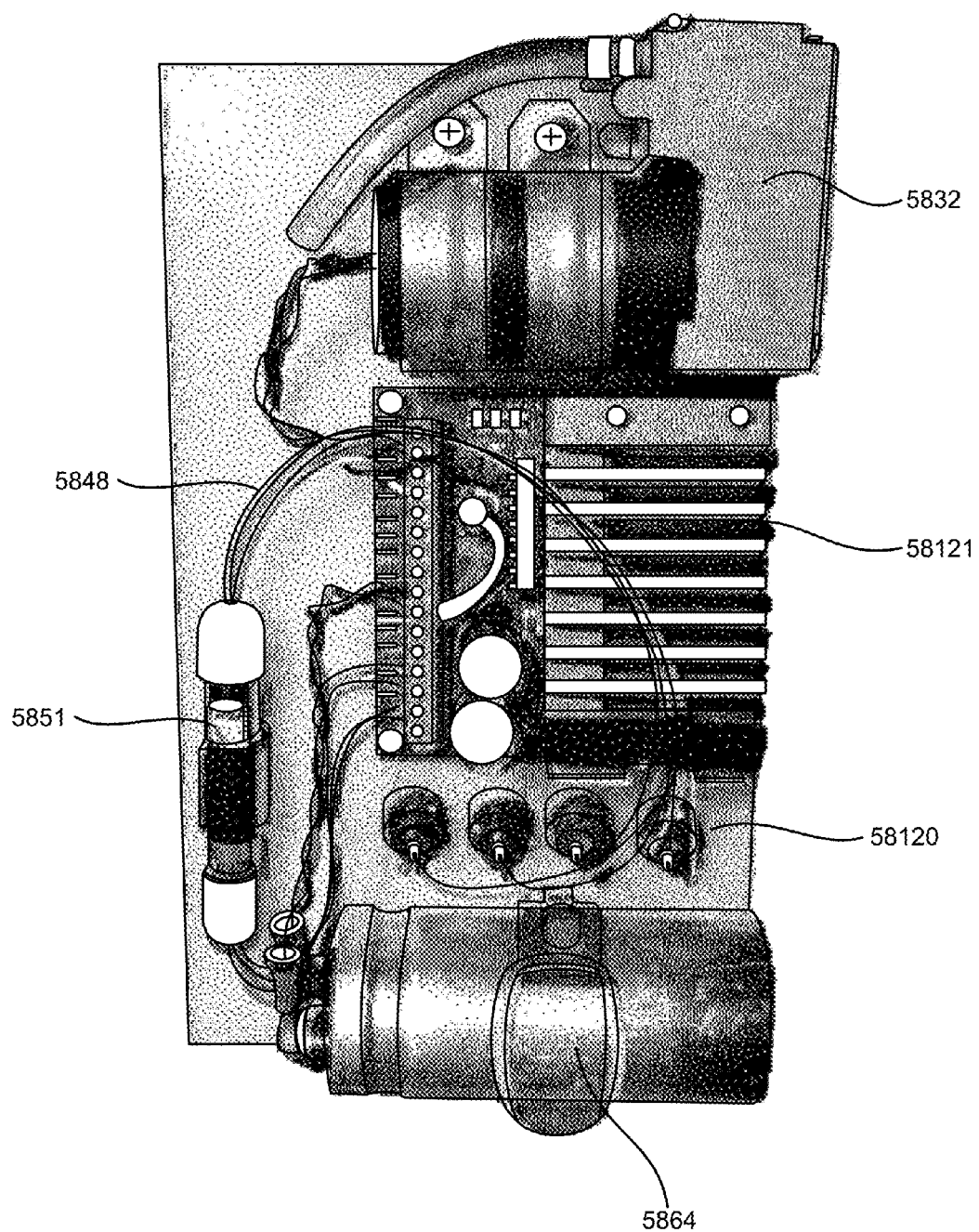
FIGS. 59A and 59B show drawings based on photographs of a front and back view of a prototype breath analysis device.
Figure 59B:
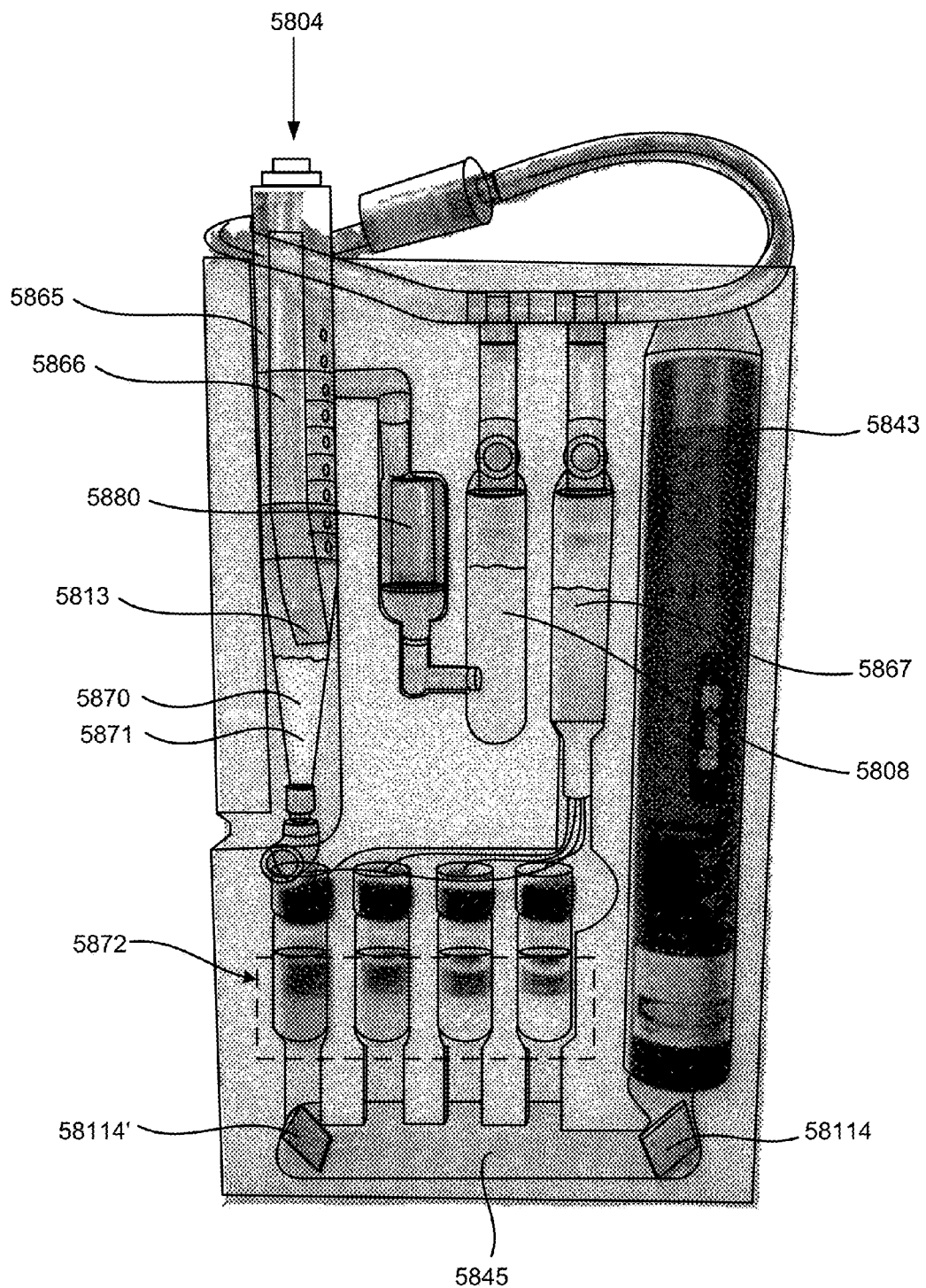

A schematic of various embodiments of a THC/alcohol analyzer is illustrated in FIG. 58, and an actual model of one embodiment of a THC-only analyzer is shown in FIG. 59. The front side of the device (picture on the left side of FIG. 59) shows a breath tube with check valve, catch solvent reservoir with catch solvent, lipophilic catch and chromatography media, flush solvent reservoir with check valve, indicator reservoir, reaction and optical detection cells (4×½ dram vials), pump laser and deflection mirrors, and various flow valves. The rear side of the device (picture on the right side of FIG. 59) shows a micropump, system controller (pump controller, power supplies, detector electronics), aspheric fiber coupled light collectors connected to each reaction and optical detection cell, optical fibers, photomultiplier detector, and replaceable/rechargeable battery. Many of these components are also shown schematically in FIG. 58.

Components of the device illustrated in FIGS. 58 and 59 and their function are summarized below (not all components are shown in both Figures):

- A mouthpiece 5802: the subject exhales into the mouthpiece to provide a breath sample through a transfer tube 5868;
- A reed-type check valve 5880 (or device providing similar functionality): stops backflow of gas or liquid catch solvent if subject inhales through mouthpiece 5802; may also serve as a saliva knockout;
- A catch solvent reservoir 5866: reservoir used to hold catch solvent and remove organic constituents from exhaled breath; in this example, contains C18 catch medium at bottom in catch media 5870 for cannabinoid sequestration and later chromatographic separation;
- Catch solvent 5865: in this case, water solvent used to collect exhaled breath constituents;
- Catch media 5870: catch media on which breath constituents may be adsorbed; in this example, the catch media 5870 is C18 phase catch media used to sequester and filter organic breath constituents, including cannabinoids;
- Liquid chromatography media 5871: liquid chromatography column configured to separate breath constituents from one another; in this example, the liquid chromatography media 5871 is additional C18 phase that is used to separate cannabinoids from chemical interferents;
- A micropump or pump 5832: creates gas pressure to pressurize and move solvent and/or indicator into/from catch solvent reservoir 5866 and elute solvents across the catch media 5870 and liquid chromatography media 5871;
- A control valve: may be used to pressurize catch solvent reservoir and drive fluids therein through catch media, and may be sealed off when pressure from pump is applied prevents backflow of catch solvent and flush solvent
- Flush solvent reservoir(s) 5808: one or more solvent reservoirs that may store flush solvent for eventual delivery to the catch solvent reservoir, such solvents may be used to elute organic interferents and cannabinoids off of C18 catch media, for example;
- THC indicator reservoir 5867: contains indicator that produces adduct with altered fluorescence properties when combined with THC; in this example, the indicator solution contains a diazo-Rhodamine-123 fluorophore tag which reacts with THC;
- Alcohol indicator reservoir 5834: contains indicator that produces an adduct with altered fluorescence properties when combined with alcohol (may operate in manner similar to THC adduct); in this example, the alcohol indicator solution contains an alcohol indicator that reacts with ethanol to form a colored or fluorescent product;
- A vent valve 5860: a valve that may be opened to allow exhaled breath gases to exit the catch solvent reservoir 5866 during subject exhale; the vent valve 5860 may be shut after the breath collection step;
- A control valve 58117: a valve that may be opened or closed to allow gas pressure from micropump 5832 to flow to the catch solvent reservoir 5866 directly or to re-route such gas pressure through one or more of the flush solvent reservoirs 5808/08' or indicator reservoirs 5867 or 5834 via one of valves 58107;
- One or more valves 58107: the valves may be used to direct gas pressure from the micropump or pump 5832 to top of solvent reservoirs to push solvent from solvent reservoirs into the CSR;
- One or more diverter valves 5838: diverter valves may be used to direct catch solvent reservoir effluent to a waste reservoir, alcohol reaction and detection cell, or THC reaction and detection cell;
- A waste reservoir 5873: a reservoir to collect catch solvent and flush solvent not used in the quantification of alcohol or THC;
- An alcohol detection cell 5869: a reaction and detection cell where a colored or fluorescent adduct with ethanol may be formed and optically detected;
- An alcohol standard cell 58118: a reaction and detection cell where a colored or fluorescent tag adduct with ethanol may be formed and optically detected; this cell may contain a known amount of ethanol (25-50 µg dissolved in water) for calibration of fluorescence-based optical signals;
- A reaction and optical detection cell 5872: a reaction cell where the fluorescent adduct with THC may be formed and/or optically detected; the suffix "u" is used to indicate a reaction and detection cell 5872 for the unknown, and the suffixes S1, S2, S3, etc. are used to indicate a reaction and detection cell 5872 for reference standards, i.e., calibrated, known amounts of THC;
- A battery 5864: a battery or other power source to provide power to the analysis unit; may be rechargeable, single-use, or replaced by external, e.g., wall, power; and
- A microcontroller 58121: one or more processors operably connected with one or more memories as well as various electrical components of analysis unit; may control pump, valves, pump light source, translation mechanism(s) (if used), etc. to obtain measurement of unknown using techniques outlined herein;

An example collection and detection methodology for various embodiments is summarized below, with reference to FIGS. 58 and 59. The sequence of events involved in the collection, concentration, separation, reactive conversion, and detection of THC in exhaled human breath using this depicted embodiment are:

(1) Subject exhales 2-3 breaths into a water-based catch solvent; saliva removal and anti-suck back is provided by an integral check valve on the breathing tube before the catch solvent reservoir. Breath flow 5804 is then passed through a porous airflow diffuser/sparger 5813 which produces fine bubbles with maximum solvent contact to facilitate mass transfer of breath constituents into the catch solvent 5865.

(2) A micropump 5832 provides gas pressure above the catch solvent and pushes the catch solvent through lipophilic absorption material/catch media 5870 and LC chromatography media 5871; organics and cannabinoids are retained within the lipophilic filter catch media 5870/LC chromatography media 5871.

(3) Flush solvent one from flush solvent reservoir 5808 is then applied to the lipophilic catch media 5870 using the aforementioned micropump 5832 to selectively elute undesirable contaminants (organics, phenols, etc. from "smoke") into the waste container.

(4) Flush solvent two (reservoir not shown in FIG. 59, but noted as flush solvent reservoir 5808' in FIG. 58) is then applied to the lipophilic catch media 5870 using the micropump to selectively elute cannabinoids from the catch media through the LC chromatography media 5871 and into the "unknown" reaction and optical detection cell 58u.

(5) After cannabinoid elution, a diazo-modified Rhodamine-based fluorophore indicator solution from indicator reservoir 5867 is applied to the unknown and THC standards. Alternatively, the diazo-modified Rhodamine-based fluorophore can first be applied to the lipophilic catch media and THC standards to react with THC, followed by application of flush solvent two.

(6) Reaction between the indicator and THC occurs, which creates a fluorescing adduct.

(7) The pump light source 5843, which is a laser in this example, is turned on and each reaction and detection cell is sequentially exposed to the laser using a stationary mirror 58114 and a translating mirror 58114' to direct the beam onto each cell. The translating mirror 58114' in this example slides in a recess that acts as a translation mechanism 5845 (although motive input to the sliding mirror 58114 is provided by a person's hand). The fluorescence signal from each reaction and optical detection cell for THC is then collected using a high-numerical-aperture (NA) aspheric optic/fiber launch 58120 and transported via optical fibers 5848 to a photon detector 5851, which is the photocathode of a high gain photomultiplier in this example. Fluorescence is then measured via photon counting for a prescribed integration time at one or two wavelengths for each cell.

(8) Fluorescence signal from the "unknown" is then compared against the three THC calibration cell signals to establish the presence and quantitative level of THC in the unknown as well as assess test validity and proper device function. The unknown THC level is then displayed in "pg THC collected" on the device readout. Also, the device indicates whether or not an internal check was passed and that the test was valid. A device fail-safe/interlock may also be included so the device cannot be used without a fresh (unused) testing cartridge (the example device is a prototype and does not include a cartridge feature).

(9) Results of the overall test (e.g., time, date, THC level, alcohol level, unique ID, calibration levels, etc.) are then written to the device's nonvolatile RAM and/or transmitted wirelessly (such as by WiFi/GSM) to a remote receiver.

(10) The testing cartridge, having been marked as used (e.g., an irreversible fracture tab with photo-eye detector is broken off when the cartridge is inserted into the analysis unit), is removed from the device and bagged as evidence.

XI. Proof of Concept Demonstration of Measurement Methodology

Figure 60:
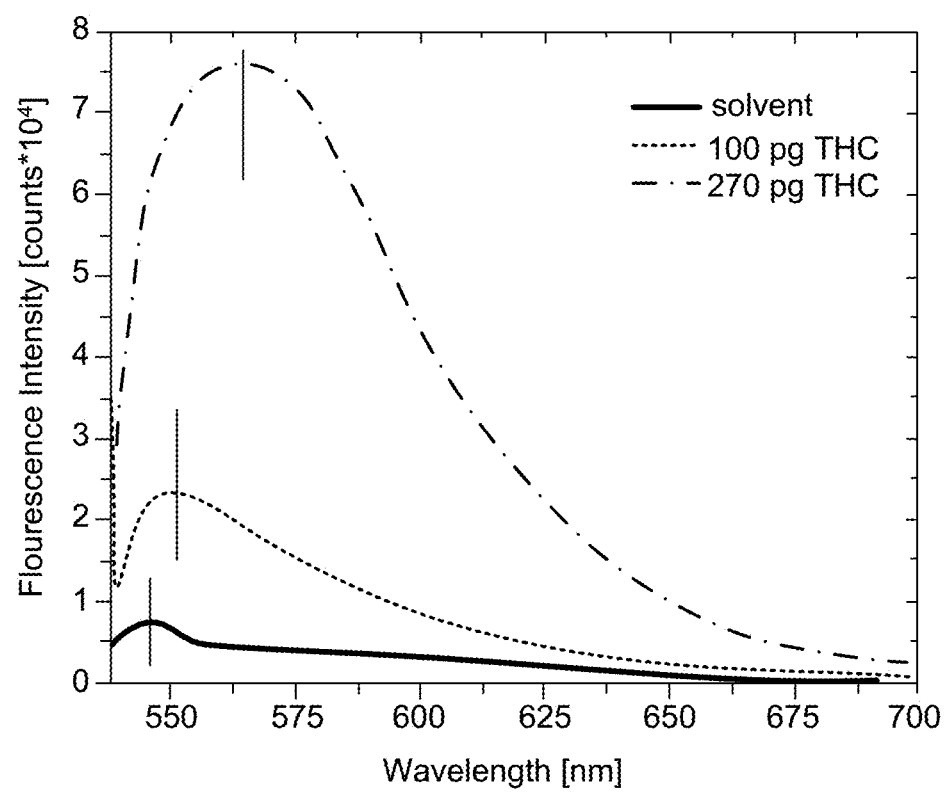
FIG. 60 is a fluorescence calibration graph for THC over a range of wavelengths.
Figure 61:
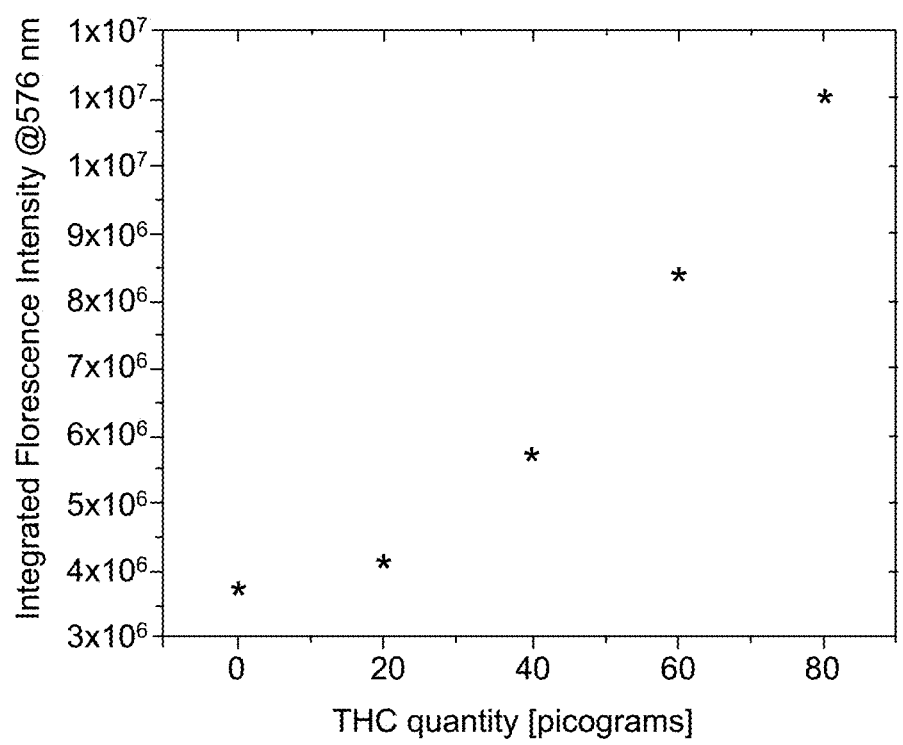
FIG. 61 is a fluorescence calibration graph for THC over a range of concentrations.

Lab results based on the aforementioned methodology showed that reaction of diazo-Rhodamine-123 with THC to form a fluorescing adduct was extremely fast (<1 min) and that emission spectra of the Rhodamine derivative, diazo-modified Rhodamine derivative, and diazo-THC adduct were spectrally distinct. The fluorescence assay developed herein demonstrated a limit of detection for THC of approximately 20 pg, as shown in FIGS. 60 and 61.

Selective Detection of THC in Exhaled Breath.

While the fluorescence assay described above is very specific to THC, a fluorescent adduct between the diazo-Rhodamine-123 fluorophore and other aromatic alcohols, such as phenol, can occur. Since phenol is found in exhaled tobacco smoke, false positives could occur if fluorescence alone is used for detection of THC. To circumvent the potential for detection of compounds other than THC, the two-stage solvent extraction and liquid chromatography procedure discussed earlier involving formic acid/methanol solutions was used to selectively and sequentially elute phenols followed by cannabinoids from the lipophilic catch and chromatography media at the base of the catch solvent reservoir.

The collection, detection and quantification methodologies for THC in exhaled human breath, as outlined above, were implemented for proof-of-concept demonstrations that THC could indeed be detected in exhaled breath after smoking *cannabis*, and that the THC quantification protocol was not sensitive to exhaled tobacco smoke. The following protocols were used for testing and data analysis.

Procedure to Establish THC Calibration Curve (Each THC Data Point was Generated Via the Following Protocol Using Fresh C18 Media and Solvents)

(1) 0.25 mL fresh C18 catch media was loaded into catch solvent reservoir (CSR).

(2) 2 mL $CH_2Cl_2$ was added to CSR and pushed through C18 media to condition the media.

(3) 2 mL $CH_3OH$ was added to CSR and pushed through C18 media to condition the media.

(4) 20, 40, 60, or 80 pg THC were added to 200 μL $H_2O$; mixture was added to CSR and pushed through C18 media to capture THC on media.

(5) 100 μL of diazo-Rhodamine-123 (RhNN at 50 μg/mL) in $H_2O$ was added to CSR and pushed through media to form the fluorescing THC adduct, which was retained on the media.

(6) 2 mL $CH_2Cl_2$ elution solvent was added to CSR and pushed through media to strip off fluorescing THC adduct; fluorescence at 576 nm was recorded in real time at the C18 media exit for 1 min during elution of fluorescing THC adduct, using ~10 mW of 532 nm green laser light. Total signal, i.e., I(t) for 1 min was integrated to give overall THC "signal" for calibration plot, see FIG. 62.

Breath Capture Protocol

Two deep exhaled breaths from the subject were sparged through 1 mL water (catch solvent) at post-smoking times of t=0, 15, 30, and 60 minutes, given the following cases:
- (a) Clean breath was used as-is, or
- (b) 5 consecutive drags were taken from a menthol cigarette over 2 min, or
- (c) 2 hits were taken via water pipe from ~100-200 mg of cannabis (THC content >10%) over 1 min.

Figure 62:
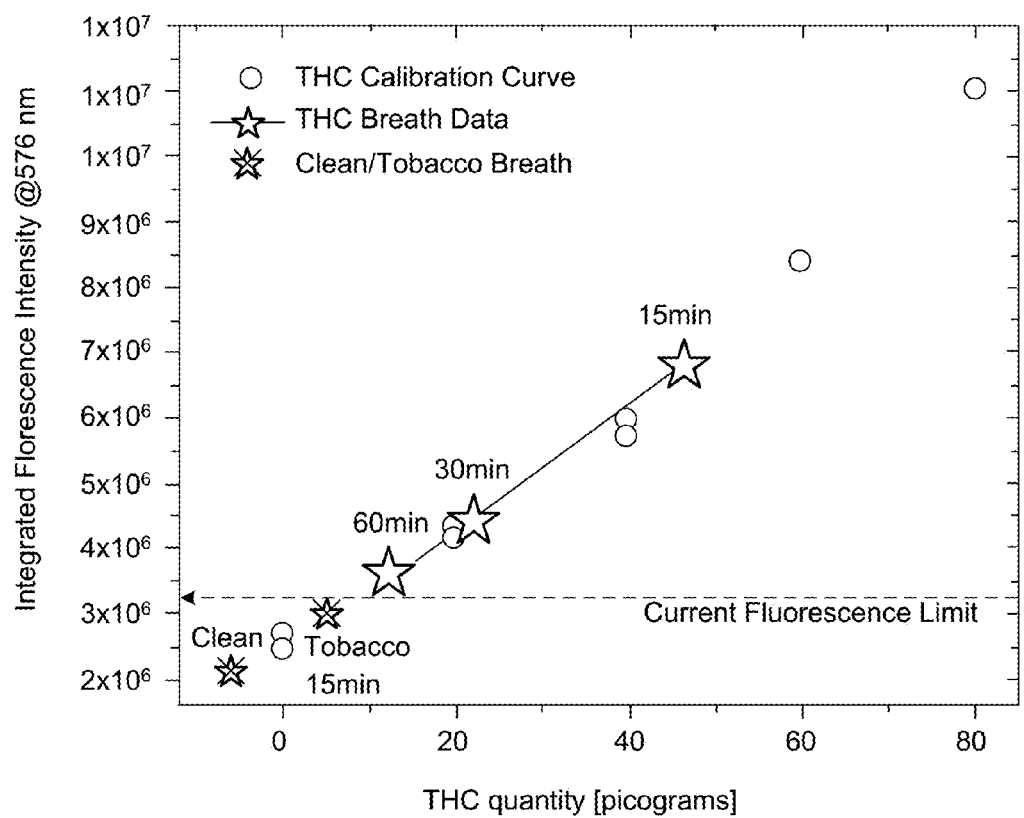
FIG. 62 is a fluorescence calibration plot for THC and detection of THC in a breath sample.

THC Quantification in Exhaled Breath Protocol
- (1) 0.25 mL fresh C18 catch media was loaded into catch solvent reservoir (CSR).
- (2) 2 mL $CH_2Cl_2$ was added to CSR and pushed through C18 media to condition the media.
- (3) 2 mL $CH_3OH$ was added to CSR and pushed through C18 media to condition the media.
- (4) The 1 mL water catch solvent from an exhalation test was added to the CSR and pushed through the C18 media to capture THC on media.
- (5) 1 mL of 2:1 methanol:water mixture was added to CSR and pushed through C18 media to remove organic interferents.
- (6) 100 μL of diazo-Rhodamine-123 (RhNN at 50 μg/mL) in $H_2O$ was added to CSR and pushed through media to form the fluorescing THC adduct, which was retained on the media.
- (7) 2 mL $CH_2Cl_2$ elution solvent was added to CSR and pushed through media to strip off fluorescing THC adduct; fluorescence at 576 nm was recorded in real time at the C18 media exit for 1 min during elution of fluorescing THC adduct, using ~10 mW of 532 nm green laser light. Total signal, i.e., I(t) for 1 min was integrated to give overall THC "signal", see FIG. 62. FIG. 62 illustrates THC fluorescence assay calibration plot (circles) and detection of THC from captured breath samples after smoking cannabis (stars). Fluorescence signals for clean breath and exhaled breath after smoking tobacco (stars with X's through them) or cannabis (stars without X's through them) at various times are shown. A polynomial fit to the THC Calibration Curve (circles) was used to calculate picograms of THC for breath samples captured after smoking cannabis.

REFERENCES

[1] *Cannabinoids in Exhaled Breath following Controlled Administration of Smoked Cannabis*, Sarah K. Himes, Karl B. Scheidweiler, Olof Beck, David A. Gorelick, Nathalie A. Desrosiers, Marilyn A. A Huestis, Clinical Chem. 59, 1780 (2013).

[2] "Detection of $\Delta^9$-Tetrahydrocannabinol in Exhaled Breath Collected from Cannabis Users," Olof Beck, Sören Sandqvist, Ilse Dubbelboer, and Johan Franck, *J. Anal. Toxic.* 35, 541 (2011).

[3] "The Detection of Δ9-Tetrahydrocannabinol in the Breath of Human Subjects," Antony Manolis, Linda J. McBurney, and Brian A. Bobbie, *Clinical Biochem.* 16, 229 (1983).

[4] "$\Delta^9$-Tetrahydrocannabinol (THC), 11-Hydroxy-THC, and 11-Nor-9-carboxy-THC Plasma Pharmacokinetics during and after Continuous High-Dose Oral THC," Eugene W. Schwilke, David M. Schwope, Erin L. Karschner, Ross H. Lowe, William D. Darwin, Deanna L. Kelly, Robert S. Goodwin, David A. Gorelick, and Marilyn A. Huestis, *Clinical Chemistry* 55, 2180-2189 (2009).

[5] L. Kadehjian, "Cannabinoid Issues: Passive Inhalation, Excretion Patterns, and Retention Times", Siemens Healthcare Diagnostics (2009), and references therein.

[6] Health Canada, "Information for Health Care Professionals: *Cannabis* (marihuana, marijuana) and the cannabinoids" (2013).

[7] "Human Cannabinoid Pharmacokinetics," Marilyn A. Huestis, *Chem. Biodivers.* 4, 1770 (2007), and references therein.

[8] S A Rahim and S G Geeso, *Talanta* 39, 1489 (1992).

[9] US Patent #20070077660-A1.

[10] "Development of Azo-Based Fluorescent Probes to Detect Different Levels of Hypoxia," Wen Piao, Satoru Tsuda, Yuji Tanaka, Satoshi Maeda, Fengyi Liu, Shodai Takahashi, Yu Kushida, Toru Komatsu, Tasuku Ueno, Takuya Terai, Toru Nakazawa, Masanobu Uchiyama, Keiji Morokuma, Tetsuo Nagano, and Kenjiro Hanoka, Angew. Chem. Int. Ed. 2013, 52 13028-13032.

[11] Die Angew. Makro. Chem. 1995, 224, 133-144

[12] US Patent App US 2012/0302907 A1

[13] Journal of Analytical Toxicology, Vol. 35, October 2011

[14] Journal of Analytical Toxicology, Vol. 34, May 2010

[15] "Cannabis Smoke Condensate I: The Effect of Different Preparation Methods on Tetrahydrocannabinol Levels," F. Van der Kooy, B. Pomahacova, R. Verpoorte, Inhalation Toxic. 2008, 20 801-804.

[16] Inhalation Toxic. 2008, xx 1-4.

[17] Thesis: "Cannabis; extracting the medicine," Arno Hazekamp, Renee Ruhaak, 2007.

[18] Book: Chemistry of Phenols

[19] Serban C. Moldoveanul and F. Kelley St. Charles, *Contributions to Tobacco Research* 22(4), 290 (2007).

[20] Ganong, William. FIG. 34-7. *Review of Medical Physiology* (21st ed.).

What is claimed is:

1. A solution of a composition of formula:

$$F—N+=NX^-.S$$

wherein:
- F is a xanthene fluorophore;
- $N+=N$ is a diazo functional group;
- $X^-$ is a negatively charged ion balancing the charge on the diazo functional group; and
- S is a diazo functional group stabilizer;

dissolved in a solvent selected for $N^+=N$ stabilization.

2. The solution of claim 1, wherein the fluorophore is a rhodamine.

3. The solution of claim 2, wherein the fluorophore is Rhodamine 123.

4. The solution of claim 1, wherein $F—N+=N$ is selected to bind to a cannabinoid.

5. The solution of claim 4, wherein the solution further comprises a cannabinoid.

6. The solution of claim 5, wherein the cannabinoid is tetrahydrocannabinol.

7. The solution of claim 6, wherein the $F—N+=N$ binds to para and/or ortho positions of a phenol ring of tetrahydrocannabinol forming an $N=N$ azo bond.

8. The solution of claim 7, wherein the $F—N+=N$ binds only to the para position of the phenol ring of tetrahydrocannabinol forming an $N=N$ azo bond.

9. The solution of claim 7, wherein the $F—N+=N$ binds only to the ortho position of the phenol ring of tetrahydrocannabinol forming an $N=N$ azo bond.

10. The solution of claim 1, wherein $X^-$ is $Cl^-$.

11. The solution of claim 10, wherein S is $ZnCl_2$.

12. The solution of claim 2, wherein $X^-$ is $Cl^-$.

13. The solution of claim 12, wherein S is $ZnCl_2$.

14. The solution of claim 3, wherein $X^-$ is $Cl^-$.

15. The solution of claim 14, wherein S is $ZnCl_2$.

16. The solution of claim 8, wherein $X^-$ is $Cl^-$.

17. The solution of claim 16, wherein S is $ZnCl_2$.

18. A composition of formula:

$$F\text{—}N{+}{=}NCl^-\cdot ZnCl_2$$

wherein:
- F is a xanthene fluorophore; and
- N+=N is a diazo functional group.

19. The composition of claim 18 wherein the fluorophore is a rhodamine.

20. The composition of claim 19, wherein the rhodamine is Rhodamine 123.

* * * * *